United States Patent [19]

Reading

[11] Patent Number: 5,474,385
[45] Date of Patent: Dec. 12, 1995

[54] METHOD AND APPARATUS FOR PARSED DYNAMIC DIFFERENTIAL ANALYSIS

[75] Inventor: Michael Reading, London, England

[73] Assignee: TA Instruments, Inc., New Castle, Del.

[21] Appl. No.: 295,515

[22] Filed: Aug. 24, 1994

Related U.S. Application Data

[63] Continuation-in-part of Ser. No. 60,214, May 7, 1993, Pat. No. 5,346,306, which is a continuation of Ser. No. 844,448, Mar. 2, 1992, Pat. No. 5,224,775.

[51] Int. Cl.$^6$ .................................................. G01N 25/00
[52] U.S. Cl. ................................. 374/11; 374/33; 374/43
[58] Field of Search ........................................ 374/1, 10, 11, 374/12, 13, 14, 16, 31, 33, 43, 110, 124, 166; 364/557, 732, 238

[56] References Cited

U.S. PATENT DOCUMENTS

| | | |
|---|---|---|
| 2,975,629 | 3/1961 | Herbert . |
| 3,263,484 | 8/1966 | Watson et al. . |
| 3,271,996 | 9/1966 | Paulik et al. . |
| 3,339,398 | 9/1967 | Barrall, II et al. . |
| 3,360,993 | 1/1968 | MacMillan . |
| 3,417,604 | 12/1968 | Bean et al. . |
| 3,527,081 | 9/1970 | Hill . |
| 3,732,722 | 5/1973 | Norem et al. . |
| 3,789,662 | 2/1974 | Zettler et al. . |
| 4,095,453 | 6/1978 | Woo . |
| 4,255,961 | 3/1981 | Biltonen et al. . |
| 4,350,446 | 9/1982 | Johnson . |
| 4,690,569 | 9/1987 | Veitch . |
| 4,783,174 | 1/1988 | Gmelin et al. . |
| 4,787,698 | 5/1988 | Wickramasinghe et al. . |
| 4,812,051 | 3/1989 | Paulik et al. . |
| 4,838,706 | 6/1989 | Coey et al. . |
| 4,840,496 | 6/1989 | Elleman et al. . |
| 4,848,921 | 7/1989 | Kunze . |
| 4,928,254 | 5/1990 | Knudsen et al. . |
| 5,046,858 | 10/1991 | Tucker . |
| 5,098,196 | 3/1992 | O'Neill . |
| 5,152,607 | 10/1992 | Ibar . |
| 5,211,477 | 5/1993 | Li . |
| 5,224,775 | 7/1993 | Reading et al. . |
| 5,248,199 | 9/1993 | Reading . |

FOREIGN PATENT DOCUMENTS

| | | |
|---|---|---|
| 0051266 | 5/1982 | European Pat. Off. . |
| 0380414 | 8/1990 | European Pat. Off. . |

OTHER PUBLICATIONS

N. Birge and S. Nagel, "Specific–Heat Spectroscopy of the Glass Transition," Physical Review Letters, vol. 54, No. 25, Jun. 24, 1985, pp. 2674–2677.

N. Birge, "Specific–heat spectroscopy of glycerol and propylene glycol near the glass transition," Physical Review B. vol. 34, No. 3, Aug. 1, 1986, pp. 1631–1642.

N. Birge and S. Nagel, "Wide–frequency specific heat spectrometer," Rev. Sci. Instrum., vol. 58, Aug. 1987, pp. 1464–1470.

S. G. Black and G. S. Dixon, "AC Calorimetry of Dimyristoylphosphatidylcholine Multilayers: Hysteresis and Annealing near the Gel to Liquid–Crystal Transition," Biochemistry, vol. 20, 1991, pp. 6740–6744.

G. S. Dixon, S. G. Black, C. T. Butler and A. K. Jain, "A Differential AC Calorimeter for Biophysical Studies," Ana (List continued on next page.)

Primary Examiner—William A. Cuchlinski, Jr.
Assistant Examiner—G. Bradley Bennett
Attorney, Agent, or Firm—Crowell & Moring

[57] ABSTRACT

The interpretation of dynamic differential calorimetry ("DDSC") data is enhanced by parsing the data according to whether it is obtained while the sample is being heated, cooled, or re-heated. Each DDSC scan is split up into three separate components, depending upon whether the sample is undergoing heating, cooling or reheating. Each component can then be analyzed separately to investigate the sample response to temperature change as the sample is being heated, cooled, or re-heated. Each file is deconvoluted separately, using a deconvolution routine that first removes the effect of the phase lag due to the instrument's finite response time.

69 Claims, 36 Drawing Sheets

OTHER PUBLICATIONS lytical Biochemistry, 121, 1982, pp. 55–61.

K. Drong, I. Lamprecht and Th. Plesser, "Calorimetric Measurements of an Intermittency Phenomenon in Oscillating Glycolysis in Cell–Free Extracts from Yeast," Thermochimica Acta, vol. 151, 1989, pp. 69–81.

V. V. Filimonov, S. A. Potekhin, S. V. Matveev and P. L. Privalov, "Thermodynamic Analysis of Scanning Microcalorimetric Data," Biophysical Chemistry, vol. 87, 1987, pp. 87–96.

E. Freire and R. L. Biltonen, "Statistical Mehanical Deconvolution of Thermal Transitions in Macromolecules. I. Theory and Application to Homogeneous Systems," Biopolymers, vol. 17, pp. 463–479 (1978).

E. Freire, W. W. van Osdol, O. L. Mayorga and J. M. Sanchez–Ruiz, "Calorimetry Determined Dynamics of Complex Unfolding Transitions in Proteins," Annu. Rev. Biophys. Biophys. Chem. 1990. 19:159–88.

R. Garcia, "Scanning Tunneling Microscopy in Biology; Changing the Pace," Microscopy and Analysis, Jul. 1991, pp. 27–29.

J. E. Graebner, "Modulated–bath calorimetry," Review of Scientific Instruments, Jun. 1989, pp. 1123–1128.

I. Hatta and A. Ikushima, "Studies on Phase Transitions by AC Calorimetry," Japanese Journal of Applied Physics, vol. 20, No. 11, Nov. 1981, pp. 1995–2011.

M. Hietschold, P. K. Hansma, A. L. Weisenhorn, "Scanning–Probe–Microscopy and Spectroscopy in Materials Science," Microscopy and Analysis, Sep. 1991, pp. 25–27.

S. Ikeda and Y. Ishikawa, "Improvement of AC Calorimetry," Japanese Journal of Applied Physics, vol. 18, No. 7, Jul. 1979, pp. 1367–1372.

S. Imaizumi, T. Matsuda and I. Hatta, "Measurement of Dynamic Specific Heat Capacity of Lysozyme Crystals," Journal of the Physical Society of Japan, vol. 47, No. 5, Nov. 1979, pp. 1643–1646.

D. H. Jung, T. W. Kwon, D. J. Bae, I. K. Moon and Y. H. Jeong, "Fully automated dynamic calorimeter," Meas. Sci. Technol., vol. 3, 1992, pp. 475–484.

S. MacPherson, "Atomic Resolution," Laboratory News, Mar. 19, 1990.

O. L. Mayorga, W. V. van Osdol, J. L. Lacomba and E. Freire, "Frequency spectrum of enthalpy fluctuations associated with macromolecular transitions," Proc. Natl. Acad. Sci. U.S.A., vol. 85, Dec. 1988, pp. 9514–9518.

O. L. Mayorga and E. Freire, "Dynamic analysis of differential scanning calorimetry data," Biophysical Chemistry, vol. 87, 1987, pp. 87–96.

M. J. Miles, "The Application of STM/AFM TO Biological Molecules,"Microscopy and Analysis, Jul. 1990, pp. 7–9.

J. Mitchell, "DSC: A new design for evaluating the thermal behavior of materials," International Laboratory, Feb. 28, 1991, pp. 44–48.

R. Point, J. L. Petit and P. C. Gravelle, "Reconstruction of Thermokinetics from Calorimetric Data by Means of Numerical Inverse Filters," Journal of Thermal Analysis, vol. 17, 1979, pp. 383–393.

H. S. Rade, "Wechselstromkalometrie–ein empfindliches und kontinuierlich registrierendes Verfahren zur Messung spezifischer Warmen kleiner Proben," Feinwerktechnik & Messtechnik, Jul. 1977, pp. 223–226.

A. Rosencwaig, "Photoacoustic microscopy," International Laboratory, Sep./Oct. 1979, pp. 37–43.

P. Sullivan and G. Seidel, "Steady–state, ac–Temperature Calorimetry," Physical Review, vol. 173, No. 3, Sep. 15, 1968, pp. 679–685.

N. F. van Hulst and F. B. Segerink, "Optical Microscopy Beyond the Diffraction Limit," Microscopy and Analysis, Jan. 1992, pp. 21–23.

W. W. van Osdol, O. L. Mayorga and E. Freire, "Multifrequency calorimetry of the folding/unfolding transition of cytochrome c," Biophysical Journal, vol. 59, 1991, pp. 48–54.

W. W. Wendlandt, "Thermal Methods of Analysis," Dept. of Chemistry, University of Houston, Houston, Texas, Second Edition, 1974, pp. 193–212.

C. C. Williams and H. K. Wickramasinghe, "Photothermal Imaging with Sub–100–nm Spatial Resolution," Photoacoustic and Photothermal Phenomena Proceedings, pp. 364–368.

H. Yao and I. Hatta, "An ac Microcalorimetric Method for Precise Heat Capacity Measurement in a Small Amount of Liquid," Japanese Journal of Applied Physics, Jan. 1988, pp. 121–122.

A. Maesono and R. Kato, "Recently Developed Instruments Relevant to AC Calorimetry," Netsu Sokutei no Shimpo, vol. 5, pp. 71–78 (1978) (With English Translation).

Ulvac Sinku–Riko, Inc. product brochure ACC–1, "AC Calorimeter," publication date unknown, Catalog No. 8909–A13E/90.71000.

Ulvac Sinku–Riko, Inc., product brochure, "Thermal Constants Analyzer by AC Calorimeter Method," publication date unknown, Catalog No. 9010–P1TR1/90.10.3000.

Ulvac Sinku–Riko, Inc., product brochure AC–VL1, "AC Calorimeter," publication date unknown, Catalog No. 9102–A24E.

Microscopy and Analysis, "Aris Scanning Tunneling Microscope," Jan. 1992.

Di product brochure, "Nanoscope II, Scanning Tunneling Microscope," publication date unknown.

Struers product brochure, "Welcome to the World of Atoms", Tunnelscope 2400, publication date unknown.

Struers product brochure, "Welcome to the World of Atoms, Tunnelscope 2400, Software Version 2.0," publication date unknown.

METHOD AND APPARATUS FOR PARSED DYNAMIC DIFFERENTIAL ANALYSIS

This application is a continuation-in-part of application Ser. No. 08/060,214, filed on May 7, 1993, issued as U.S. Pat. No. 5,346,306 which is a continuation of application Ser. No. 07/844,448 (the "parent application"), filed Mar. 2, 1992, issued as U.S. Pat. No. 5,224,775. Both applications are incorporated by reference herein.

The appendices to this application contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

1. Field of the Invention

The present invention relates to differential analytical techniques for determining the composition, phase, structure, or other properties of a sample of material.

2. Background of the Invention

Dynamic differential scanning calorimetry ("DDSC"), introduced by TA Instruments as modulated differential scanning calorimetry™ ("MDSC™"), and described in U.S. Pat. No. 5,224,775 (the "'775 patent"), has proved to be a major advance in Differential Scanning Calorimetry ("DSC"). It improves the accuracy of DSC and significantly increases the amount of information that can be deduced from DSC data.

DYNAMIC DSC

In DDSC, a rapid heating rate oscillation is added to a conventional linear temperature ramp. If the heating rate oscillation has a low amplitude but a high frequency, then it is possible to obtain a relatively high instantaneous heating rate even though the underlying heating rate is comparatively low. The heat flow to and from the sample is recorded, and then deconvoluted into rapidly reversible and non-rapidly reversible components.

FIG. 1 is a schematic diagram of TA Instruments' DDSC (or MDSC™) apparatus which is described in more detail in U.S. Pat. No. 5,224,775. Apparatus 111 comprises a sample pan 112; reference pan 113; sample temperature thermocouple 114; reference temperature thermocouple 115; thermoelectric disc 116; purge gas inlet 117; purge gas outlet 118; electric furnace 119 comprising silver block heater 120, silver ring 121, silver lid 122, and heater thermocouple 123; furnace chamber 124; heater controller 125; analog-to-digital converter 126; and microcomputer 127. It also comprises a personal computer 110 and digital plotter 109.

The differential scanning calorimeter measures the heat flow difference between sample pan 112 and reference pan 113, which are supported by a thermoelectric disc 116 inside a closed furnace chamber 124. The thermoelectric disc 116 serves as the major heat flow path for transferring heat from furnace 119 to sample pan 112 and reference pan 113. The disc is also used as the common material of the differential thermocouple for measuring the temperature difference between the sample and reference pans. Microcomputer 127 receives differential temperature and sample temperature from sample thermocouple 114 and reference thermocouple 115 via analog-to-digital converter 126. Microcomputer 127 also controls the temperature of the furnace 119 by controlling the power to the furnace using heater controller 125.

Personal computer 110 and digital plotter 109 are used to analyze, store, display and plot the analytical results. A purge gas is usually introduced via the purge gas inlet. The purge gas can be a gas that reacts with constituents of the sample being analyzed, or it can be an inert gas, i.e., a gas that does not react with the sample used to prevent reactions with air. Typical purge gases include dry air, oxygen, nitrogen, argon, helium, carbon monoxide and carbon dioxide.

DEFINITIONS

"Transition" or "Transformation", as used herein, mean any type of physical or chemical transformation, phase change, or structural change in a material.

"Analyzing", as used herein with respect to materials, means determining the composition, phase, structure, and/or identification of the material.

"Rapidly reversible", as used herein, means any portion of a signal, transition, or event which is a direct function of the rate of change of temperature. For example, the contribution to the heat flow signal in DSCs attributable to the rate of change of temperature of the sample material is a rapidly reversible transition. In DSC, for example, one of the contributions to the rapidly reversible portion of the heat flow signal is the heat capacity of the sample material. Rapidly reversible processes include those processes which are thermodynamically reversible and have small kinetic time constants relative to the rate of change of the driving variable.

"Non-rapidly reversible", as used herein, means any portion of a signal, transition or event which is a direct function of the value of the temperature. For example, the contribution to the heat flow signal in DSC attributable to the absolute temperature of the sample material is a non-rapidly reversible transition. This might be caused by a chemical or physical change taking place such as recrystallization. Non-rapidly reversible processes include those processes which are thermodynamically irreversible, as well as processes which are thermodynamically reversible, but which reverse very slowly relative to the rate of change of the driving variable due to the kinetic limitations of the process.

"Deconvolution" as used herein, means the process of separating the dependence of, e.g., heat flow in a differential scanning calorimeter, into one or more component parts so that the component parts can be utilized or analyzed separately, or compared with each other. For example, in DSCs, the dependence of heat flow on temperature can be deconvoluted into rapidly reversible and non-rapidly reversible components.

"Parset", as used herein, is a part-cycle of data.

SUMMARY OF THE INVENTION

The present invention enhances the interpretation of DDSC data by parsing the DDSC data into shorter sections or "parsets" of data depending upon the conditions that the sample is experiencing at any given moment in time. These parsets of data can then be analyzed individually to give a more accurate interpretation of the sample response to the DDSC temperature program.

In the first preferred embodiment of the present invention, the heat flow data is parsed according to whether it is obtained while the sample is being heated, cooled, or reheated. In the second preferred embodiment of the present invention, the heat flow data is parsed according to whether the cyclic component of the modulated heat flow data is positive or negative. In the third preferred embodiment of the present invention, the heat flow data is parsed depending upon whether the cyclic component of the temperature is positive or negative. In a fourth preferred embodiment of the present invention, the heat flow data is parsed according to whether the cyclic component of the derivative of the modulated temperature is positive or negative.

Each of the four preferred embodiments of the present invention can be applied to DDSC data obtained using a single modulation frequency ("standard DDSC") or to DDSC data using two or more modulation frequencies ("multiplexed DDSC"). Multiplexed DDSC can provide, in a single measurement, data showing the response of a sample to two (or more) different modulation frequencies. Thus it increases the throughput of a DDSC instrument, by using one DDSC run to obtain data that would otherwise require separate runs at each of the different modulation frequencies. Moreover, in some cases, the type of data that can be obtained from a single multiplexed DDSC measurement would not be obtainable from separate sequential DDSC measurements.

The first preferred embodiment of the present invention is shown in FIGS. 2a–2d. As shown in FIGS. 2a–2d, each DDSC scan is split up into three separate components depending upon whether the sample is undergoing heating, cooling or re-heating. The relative size of the heating, cooling and re-heating components is determined by the profile of the modulated temperature (i.e., by the DDSC parameters set by the operator). Once these three components have been isolated, they can each be analyzed individually to investigate the sample response to temperature change under each of these different regimes.

Computer programs implementing the first preferred embodiment of the present invention in Microsoft Qbasic are included at Appendix A. The first program (the "parsing program") splits the data into three separate files (heating, cooling and re-heating) by comparing the temperature at an instant with the previous recorded temperature. The parsing program contains a short "memory" to remove any ambiguity when two adjacent temperature values are the same. The second program (the "deconvolution program") deconvolutes the data in each file into rapidly reversible and non-rapidly reversible components. The programs implement the present invention in QuickBasic. The programs are:

1/ TEMPAR1.BAS—Queries the user for the parsing method and works upon two report files written from the module controller. The first file should contain Time(s), Modulated Temperature (°C.) and Underlying Temperature (°C.) and Derivative of Modulated Temperature (°C./s). The second file should contain Time(s), Derivative of the Average Temperature (°C./s), Modulated Heat Flow (mW) and Average Heat Flow (mW). The 1.5 cycle data delay induced by the DDSC software in the average signals is removed and then the data are subtracted from their respective modulated signals to leave the cyclic components. The output file consists of Time, Mod Temp, Cyclic Mod Temp, Cyclic deriv Mod Temp, Cyclic Mod Heat Flow.

2/ TEMPAR2.BAS—Works upon the output from TEMPAR1. The data is split into 3 separate files according to whether the sample is being heated, cooled or reheated. It works by comparing the Modulated Temperature at an instant with the previous temperature and it has a short 'memory' to remove the ambiguity when two adjacent values are the same.

3/ TEMPAR3.BAS—Works upon the three output files in turn from TEMPAR2. It loads in one parset of data at a time and performs a linear regression on the Cyclic Deriv Mod Temp and the Cyclic Mod Heat Flow data. It then moves the Cyclic Mod Heat Flow data forward by one step in time and recalculates the line of best fit. This process continues until the phase difference is resolved (the relationship becomes as linear as possible—calculated by a least square fit). Time, parset number, gradient, intercept and phase lag are written to a file ready for analysis in LOTUS 1-2-3.

4/ CMTPAR2.BAS—Works upon the output from TEMPAR1. The data is split into 2 files depending upon whether the cyclic component of the modulated temperature is positive or negative at any moment in time, i.e., whether the sample experiences above average or below average heating rates.

5/ CDTPAR2.BAS—Works on the output from TEMPAR1. Parses as in CMTPAR2 except it depends upon the Cyclic derivative of modulated temperature.

6/ CHFPAR2.BAS—As CMTPAR2 except it parses according to Cyclic Heat Flow being positive or negative.

7/ CYCPAR3.BAS—Works upon the output from any of the above three programs. It calculates the heat capacity and phase lag data using the same principles as TEMPAR3 but the main program loop is executed twice rather than three times.

Computer programs implementing all four preferred embodiments of the present invention in Microsoft Qbasic are included at Appendix B.

Deconvolution

When the different components are contained in separate files, each file can be separately deconvoluted. However, the conventional DDSC deconvolution program cannot be used with the present invention, because it needs one and a half complete cycles of raw data to deconvolute each data point. The following shows how part-cycles of DDSC heat flow data can be deconvoluted.

The fundamental equation describing the response of a sample to a DDSC heating program is:

$$\frac{dQ}{dt} = -(b + A\omega\cos(\omega t))C_p + C\sin(\omega t) + f'(t,T)$$

where:
dQ/dt is the modulated heat flow;
(b+Aω Cos (ωt)) is the derivative of the modulated temperature, i.e., the measured quantity dT/dt;
$C_p$ is the heat capacity;
f(t,T) is a function of time and temperature that governs the kinetic response of a physical or chemical transformation; and
f'(t,T) is f(t,T) averaged over the modulation period.

The equation for the underlying heat flow response to the modulated heating program is:

$$\text{Underlying } \frac{dQ}{dt} = -bC_p + f(t,T)$$

This underlying heat flow is equivalent to the heat flow obtained using conventional differential scanning calorimetry.

The underlying heat flow is subtracted from the modulated heat flow to calculate the cyclic component of the heat flow:

$$\text{cyclic } \frac{dQ}{dt} = -(A\omega\cos(\omega t))C_p + C\sin(\omega t)$$

where (Aω cos (ωt)) is the cyclic derivative modulated temperature. C sin (ωt) is the kinetic response to the temperature modulation. This quantity is often insignificant in comparison to the signal arising from $C_p$.

In principle, the cyclic derivative of the modulated temperature and the cyclic heat flow are sinusoidal. There is a phase lag between these two signals as a consequence of both the effect of the kinetic response C sin (ωt) (when present) and the response time of the calorimeter. FIG. 3 is a plot of the cyclic heat flow signal versus time. As shown by FIG. 4, the phase lag causes the cyclic –dT/dt v. cyclic heat flow plot to be a curve, instead of a straight line. If one of the signals is shifted in such a way as to eliminate this phase lag, a plot of –dT/dt against dQ/dt will be a straight line. The slope of this straight line should be either (1) proportional to the sample's heat capacity when there is no significant kinetic effect, or (2) proportional to the apparent heat capacity when such an effect is present.

When taken over a whole cycle, this deconvolution technique is equivalent to the Fourier transform deconvolution technique described in U.S. Pat. No. 5,224,775. However, unlike that deconvolution technique, this technique can also be applied to any fraction of a modulation cycle, or to any set of data, irrespective of whether the data is distributed evenly over time.

As discussed above, the linearity of the data which appears as a curve in FIG. 4 can be improved by shifting the cyclic heat flow signal with respect to the cyclic –dT/dt signal. FIG. 5 shows the data of FIG. 4 shifted to partially improve its linearity. FIG. 6 shows how the data of FIG. 4 can be plotted as a straight line by optimally shifting the cyclic heat flow signal with respect to the cyclic –dT/dt signal.

The optimum shift is determined as follows:

1. Calculate the least squares fit of the first part-cycle of data (or parset) to a straight line, by subjecting the data (in its original form) to a linear regression.
2. Advance the cyclic heat flow data forwards by one step in time, i.e., by one data sampling interval.
3. Calculate the least squares fit of the shifted data to a straight line.
4. If the linearity of the data is improved, advance the cyclic heat flow data an additional sampling interval.
5. Continue calculating least squares fits and advancing the data (as in the example shown in FIG. 5) until the plot is as linear as possible (as in the example shown in FIG. 6). The slope or gradient of the line of best fit is now proportional to the heat capacity of that parset of data. This process is repeated for every parset in the data file.

This analysis is carried out for each heating, cooling and re-heating file, resulting in three additional files, each containing five columns of information: Initime, Sectn, Grad, Intcpt, Phase.

Initime: The real time of the first data point in each parset.

Sectn: The index number of the parset being analyzed.

Grad: The slope or gradient of line of best fit (i.e., the heat capacity for that parset).

Intcpt: The intercept of the line of best fit.

Phase: The phase lag for that parset.

Computer programs implementing this technique are included herein at Appendix A.

Generally, three measurements are carried out: one with an empty sample pan, one with a reference material (e.g., sapphire) in the sample pan, and one with a sample material in the sample pan. Each measurement is analyzed as described above. The apparatus is then calibrated (to correct for the heat capacity of the empty sample pan) by subtracting the heat capacities obtained with the reference material in the sample pan from the known values of the heat capacities of the reference material over the whole temperature range. Each point in the sample measurement is then multiplied by the calibration constant for that temperature to calculate the actual heat capacity of the sample at that temperature.

The present invention can be used to investigate the kinetics and thermodynamics of polymers during the melting and rearrangement of metastable crystallites. It can also be used to investigate transitions in other materials.

Accordingly, it is an object of the present invention to improve the understanding of transitions in polymers and other materials by parsing data obtained using a dynamic differential scanning calorimeter into separate subsets, depending upon the temperature conditions (described above) the sample was experiencing while the data was obtained.

It is another object of the present invention to improve the understanding of transitions in polymers and other materials by parsing data obtained using a dynamic differential scanning calorimeter into separate subsets, depending upon whether the data was obtained during heating, cooling or reheating of the sample.

It is another object of the present invention to improve the understanding of transitions in polymers and other materials by parsing data obtained using a dynamic differential scanning calorimeter into separate subsets, depending upon whether the data was obtained while the cyclic component of the modulated heat flow data was positive or negative.

It is another object of the present invention to improve the understanding of transitions in polymers and other materials by parsing data obtained using a dynamic differential scanning calorimeter into separate subsets, depending upon whether the data was obtained while the cyclic component of the temperature was positive or negative.

It is another object of the present invention to improve the understanding of transitions in polymers and other materials by parsing data obtained using a dynamic differential scanning calorimeter into separate subsets, depending upon whether the data was obtained while the cyclic component of the derivative of the modulated temperature was positive or negative.

DETAILED DESCRIPTION OF THE INVENTION

Figure 1:
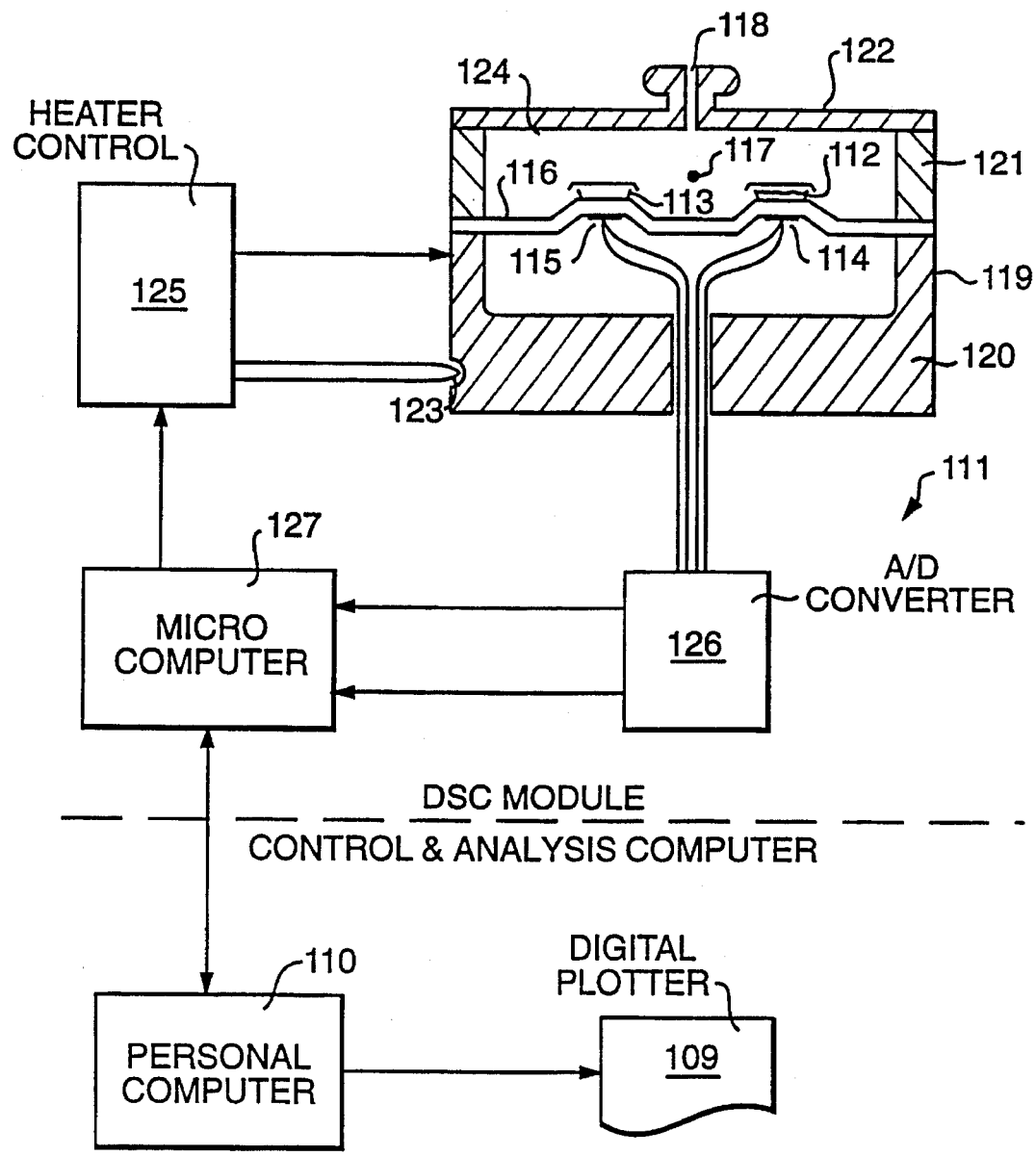
FIG. 1 is a schematic block diagram of a DDSC apparatus.
Figure 2A:
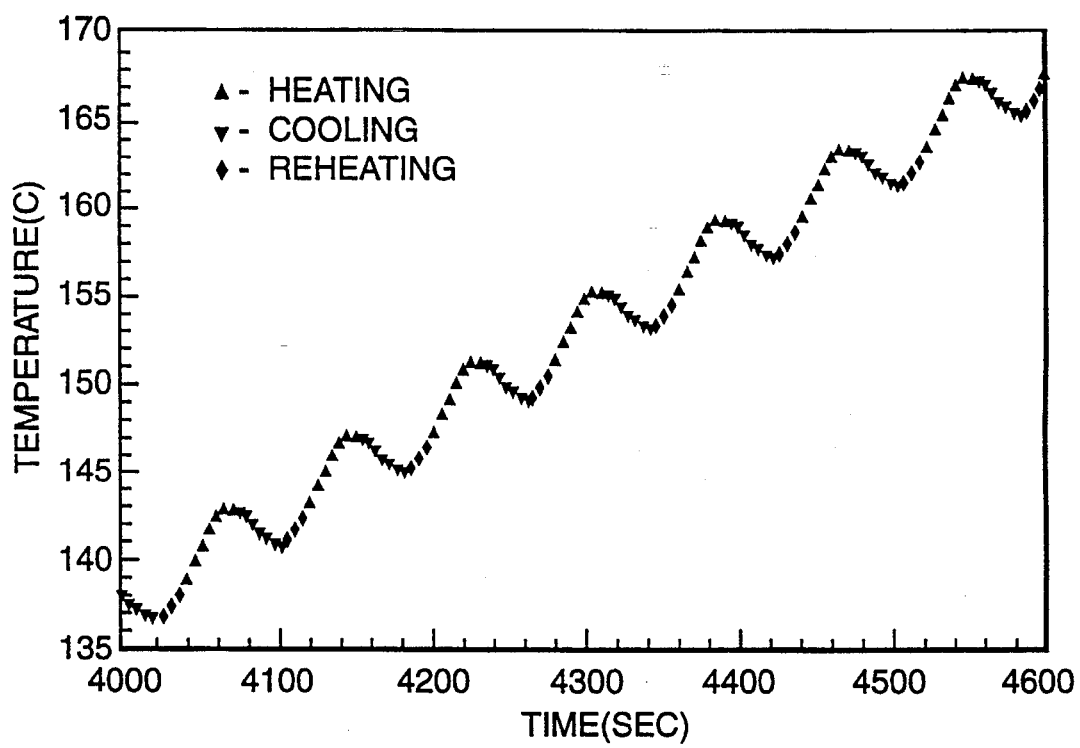
FIG. 2a is a plot of the temperature of an DDSC run, showing how the temperature is broken down into heating, cooling and re-heating components.
Figure 2B:
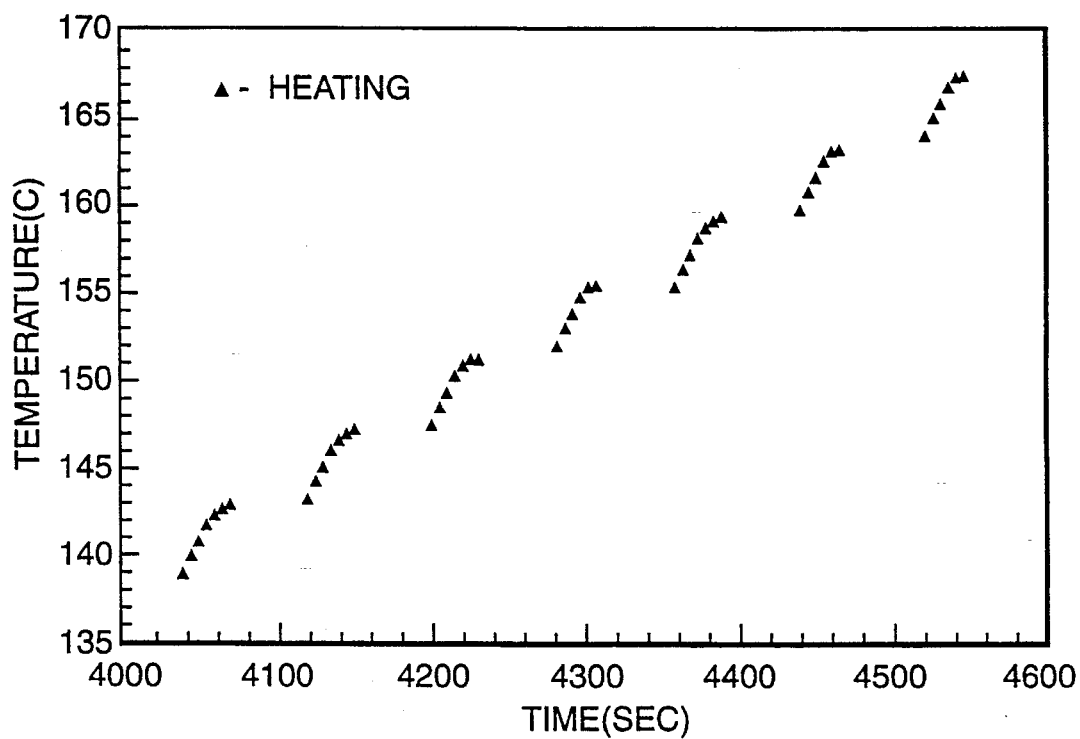
FIG. 2b is a plot of the heating component of the DDSC run shown in FIG. 1.
Figure 2C:
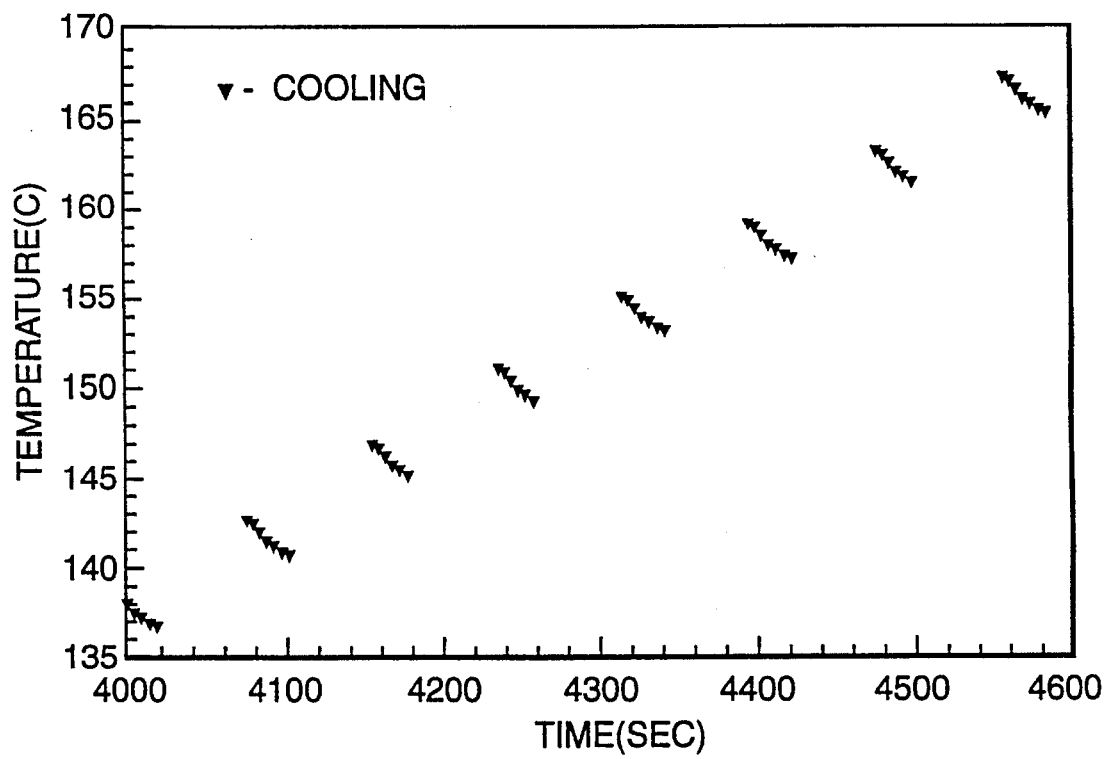
FIG. 2c is a plot of the cooling component of the DDSC run shown in FIG. 1.
Figure 2D:
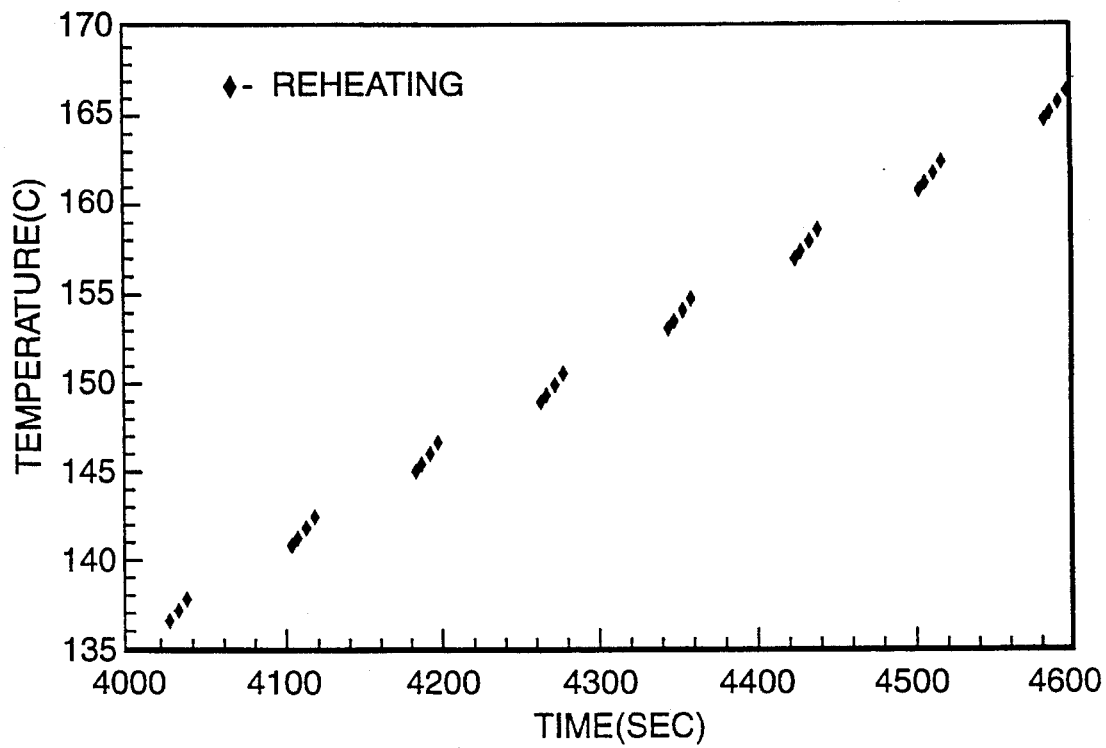
FIG. 2d is a plot of the re-heating component of the DDSC run shown in FIG. 1.

Cooling a sample during a melt changes the type of results that are obtained by introducing an asymmetry in the response of the sample. Under these conditions, the standard DDSC deconvolution approach is invalid. However, it is not always possible to avoid cooling if a good signal to noise ratio is required. Parsing overcomes this problem and provides additional information about the sample and its propensity to supercool. It therefore has very general applicability and should be routinely used to check that an measurement contains no asymmetry, and to show that results obtained using Discrete Fourier transforms are valid.

General Observations

The present invention will be described in detail using the examples below. The following comments apply generally to all the embodiments of the present invention described in the examples.

Because the analysis method 'loses' data points as the Cyclic Heat Flow column is moved forward in time, if there are not a sufficient number of data points, the linear fit will always improve whether or not the phase lag is being removed. To make sure that this does not occur, the data parsets must be as large as possible, with equal amounts of heating, cooling and reheating in each cycle. This limitation is not as severe in the Cyclic Parsing methods, because in those methods the data is split up symmetrically.

Also, analysis of each parset results in only one data point. Thus it results in a decrease in resolution of the processed data. In principle, alternative methods of analyzing parsed data are possible. However, the Linear Regression/Least Square Fit method illustrated herein as provided the best results.

Calibration

The measurements in the examples described below were calibrated by running separate Empty Pan and Sapphire Disk measurements under identical conditions to the Sample run. The Empty Pan measurement was run first, with the lid uncrimped so that the same pan could be used in all three runs. This eliminated any errors that might have arisen from using non-uniform sample pans. For the second measurement the lid is removed and a sapphire disk (60.637 mg) was placed in the pan, the lid being replaced on top. Finally the sapphire was removed and the sample was put in its place. A flat and thin sample was selected—the quenching process described below involved flattening the sample with the lid while it was isotherming in the melted state.

To calculate the response of the sample (and sapphire) only, the baseline data from the Empty Pan measurement was subtracted from the results of the other two measurements. The resulting sapphire data was compared to a polynomial fit of its literature values over the whole temperature range. The results were used to calculate individual calibration constants for every data point of the measurement. The sample data was then multiplied by these constants to give the final calibrated results.

EXAMPLE 1

The First Preferred Embodiment

The first preferred embodiment of the present invention, implemented using the programs listed in Appendix A, is illustrated in this example, with three DDSC runs. The first run was carried out using an empty sample pan, the second run was carried out using a sapphire sample, and the third run was carried out using a sample of poly(ethylene terephthalate) ("PET"). The empty pan and sapphire runs served to calibrate the method. The third run is an example of the actual use of parsed DDSC to obtain heat capacities parsed according to whether the sample was being heated, cooled or re-heated.

All DDSC runs were carried out on a TA Instruments DSC2910 Differential Scanning Calorimeter operating with a 25 cc/min Helium purge. The PET sample used was approximately 16 mg. of ICI MELINEX PET which was quenched by rapid cooling to room temperature from a ten-minute isotherm at 270° Celsius. It was then analyzed over the temperature range from −30° C. to 330° C., at an underlying heating rate of 3° C./min.

The modulation parameters which were found to be most useful for measuring the heat capacities of PET were a period of 80 seconds (the maximum obtainable on TA Instruments' DSC2910 DSC) and a programmed amplitude of 2° C. The programmed amplitude of 2° C. was not fully achieved by the DSC cell. The empty pan and sapphire disk runs were carried out using the same modulation parameters as the PET run.

Figure 3:
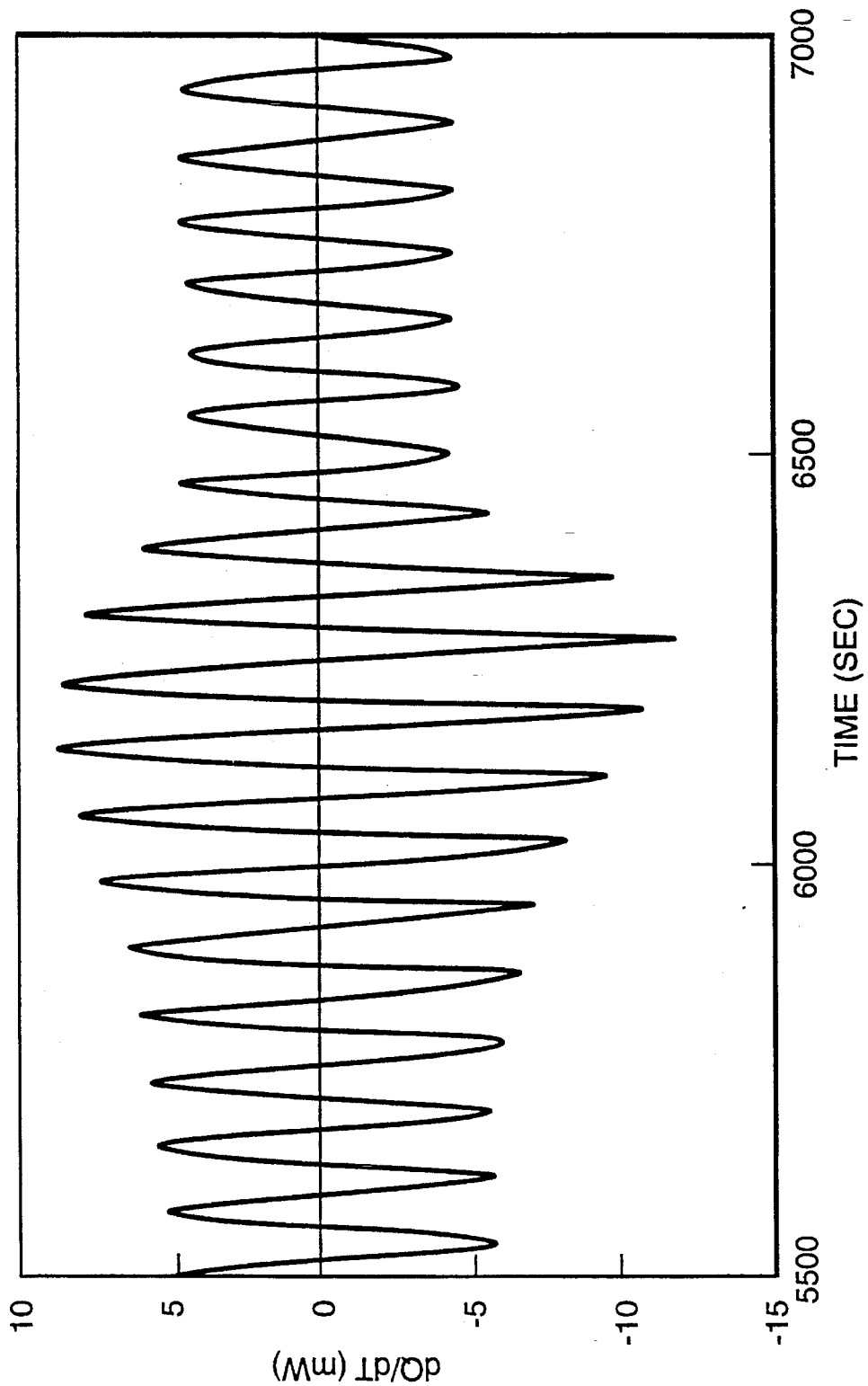
FIG. 3 is a plot showing the cyclic heat flow through the melting peak of PET.
Figure 4:
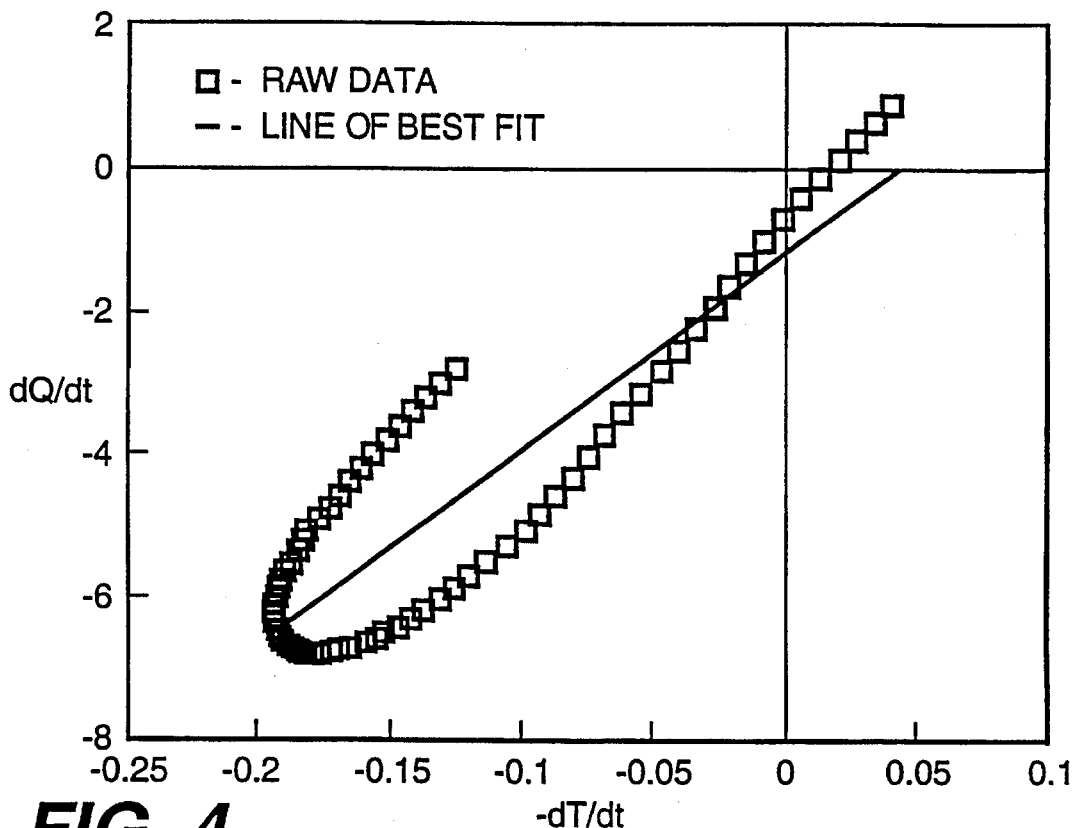
FIG. 4 is a plot of one parset of data, prior to correcting the data for instrumental phase lag.
Figure 5:
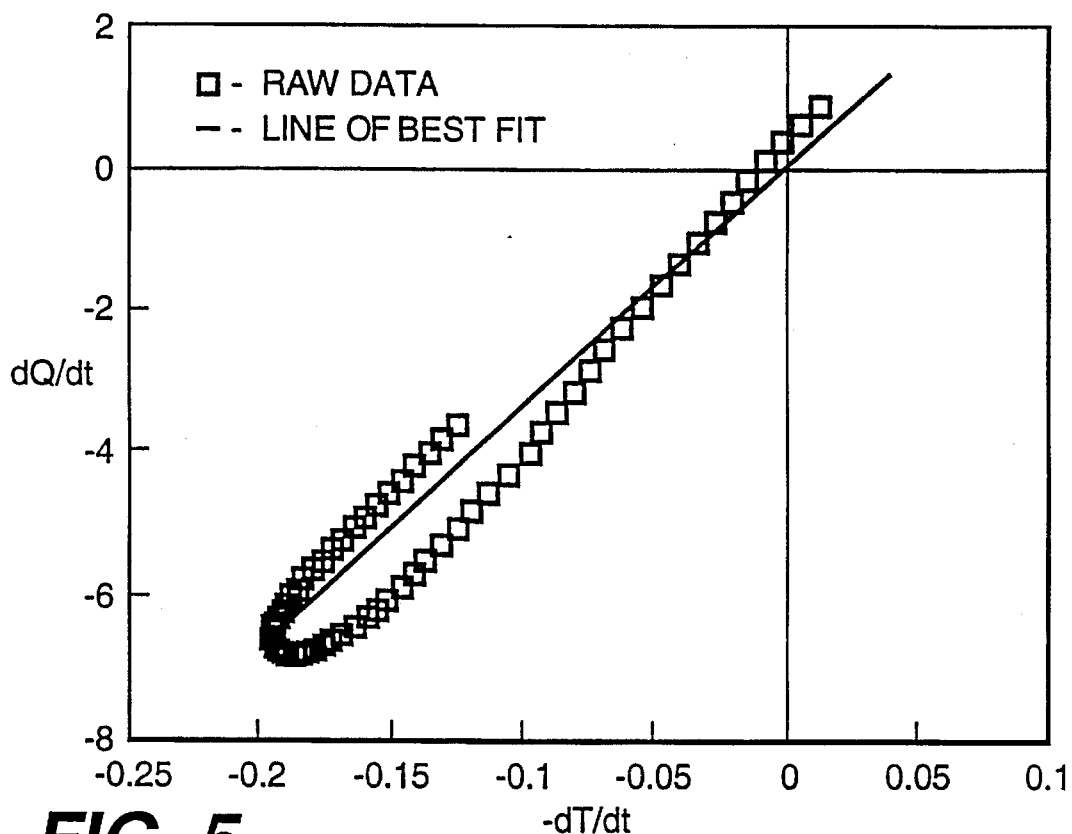
FIG. 5 is a plot of one parset of data, partially corrected for instrumental phase lag.
Figure 6:
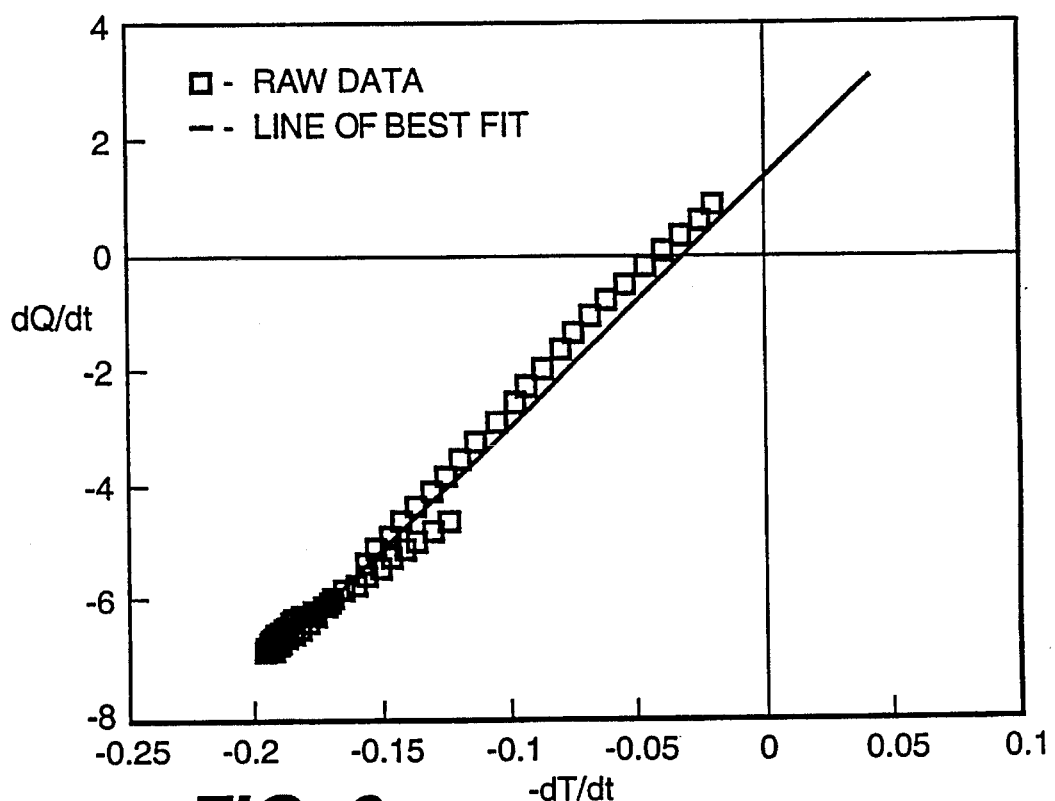
FIG. 6 is a plot of one parset of data, fully corrected for instrumental phase lag.

The following data was recorded during each run: time (in seconds), modulated temperature (in °C.), modulated heat flow (in mW), underlying heat flow (in mW) and the derivative of the modulated temperature with respect to time (in °C./second). When a run was completed the data was converted to ASCII format, and then imported into LOTUS 1-2-3. The underlying heat flow data was subtracted from the modulated heat flow data (after correcting for the one and a half cycle delay induced by the DDSC deconvolution program) to provide the cyclic heat flow data, as shown in FIG. 3. The five columns of data (time, modulated temperature, cyclic heat flow and the derivative of the modulated temperature) were then exported from LOTUS 1-2-3 as another ASCII file. The data was then ready to be parsed.

The apparatus was calibrated to correct for the heat capacity of the empty sample pan by subtracting the empty sample pan run data from the sapphire run data, and then comparing the net sapphire data to literature values for sapphire over the whole temperature range. A calibration factor was thus obtained for every point in the PET measurement—each point in the PET data was multiplied by the calibration factor to obtain the actual measured PET heat capacities.

Figure 8:
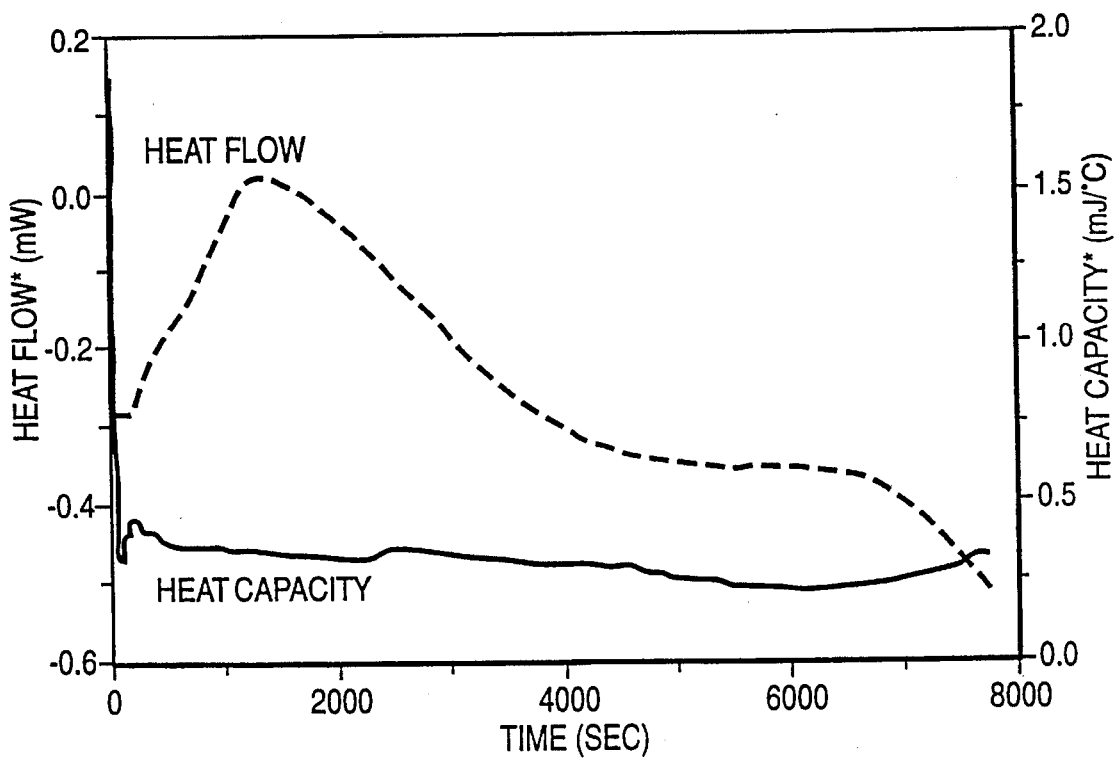
FIG. 8 is a plot of empty sample pan data obtained using conventional DDSC.
Figure 7:
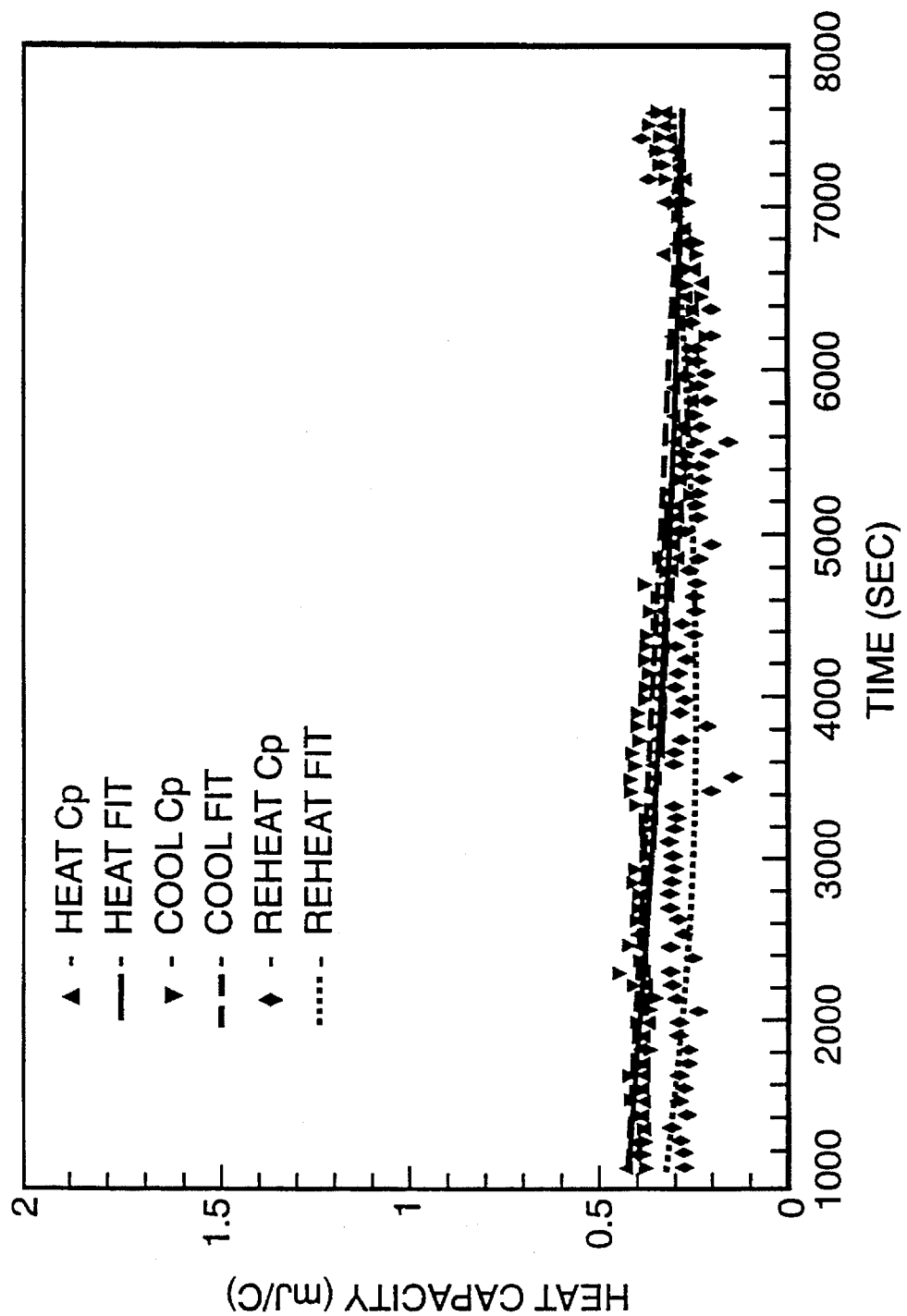
FIG. 7 is a plot of empty sample pan DDSC data as calculated by parsing and second order polynomial fits.

The heating, cooling and reheating components of the heat capacity obtained for the empty pan are shown in FIG. 7. These three components are very similar to each other, and their absolute values are comparable to the standard DDSC heat capacity calculated using the deconvolution algorithm disclosed in the parent application, shown in FIG. 8 (see Table 8). Second-order polynomials were then fitted to each of the three heating, cooling and re-heating empty-pan heat capacity data sets.

Figure 9:
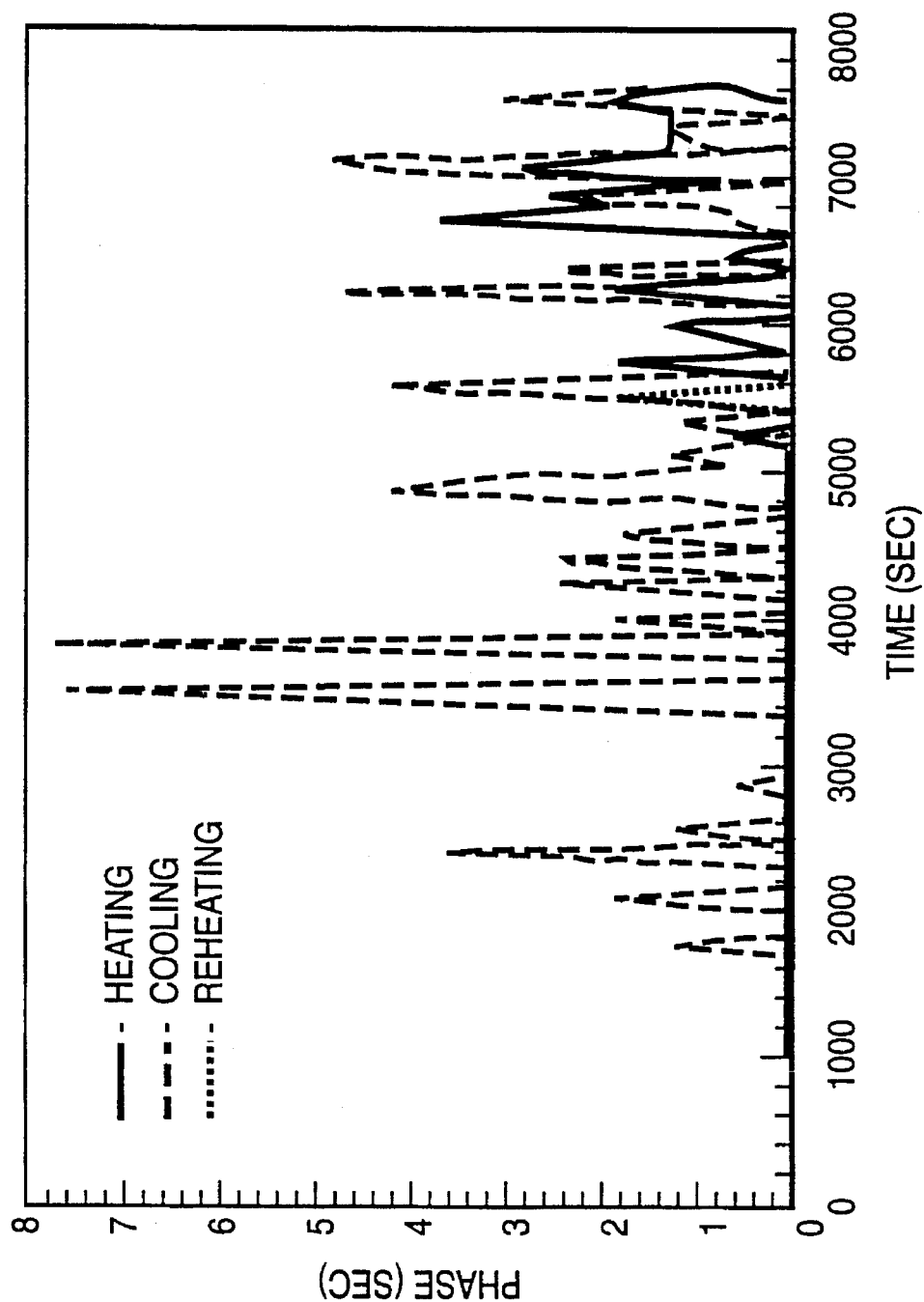
FIG. 9 is a plot of empty sample pan phase lag data.

The phase lag measurements, shown in FIG. 9, exhibit excessive noise (in an ideal instrument, the phase lag would be zero over the whole temperature range). The noise in the empty sample phase lag data is high because the heat flow is low when the sample pan is empty. Thus any small anomalies have a disproportionate effect on the fitting algorithm. However, these errors do not have a very significant effect on the heat capacity measurements.

Figure 10:
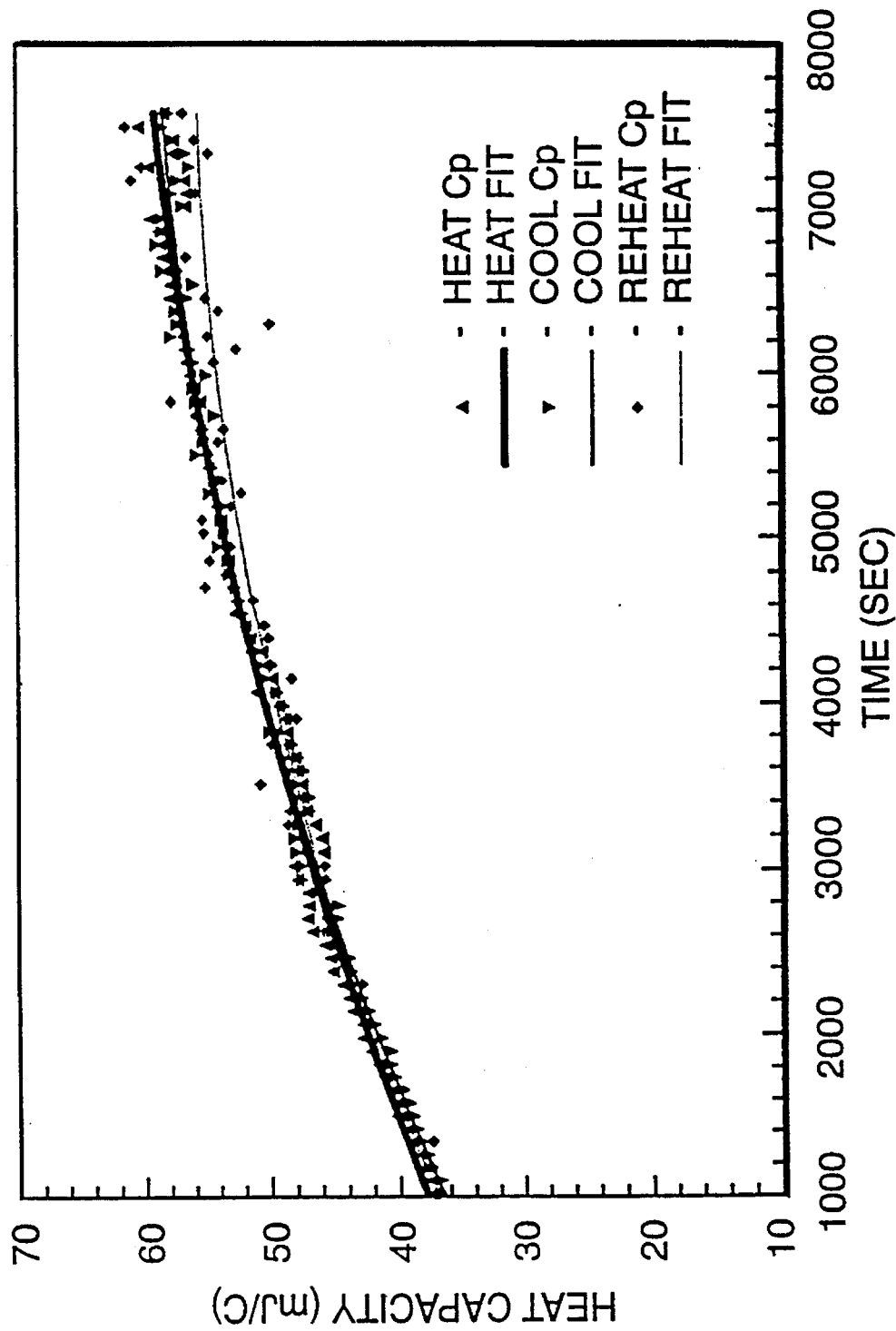
FIG. 10 is a plot of parsed sapphire heat capacities.
Figure 11:
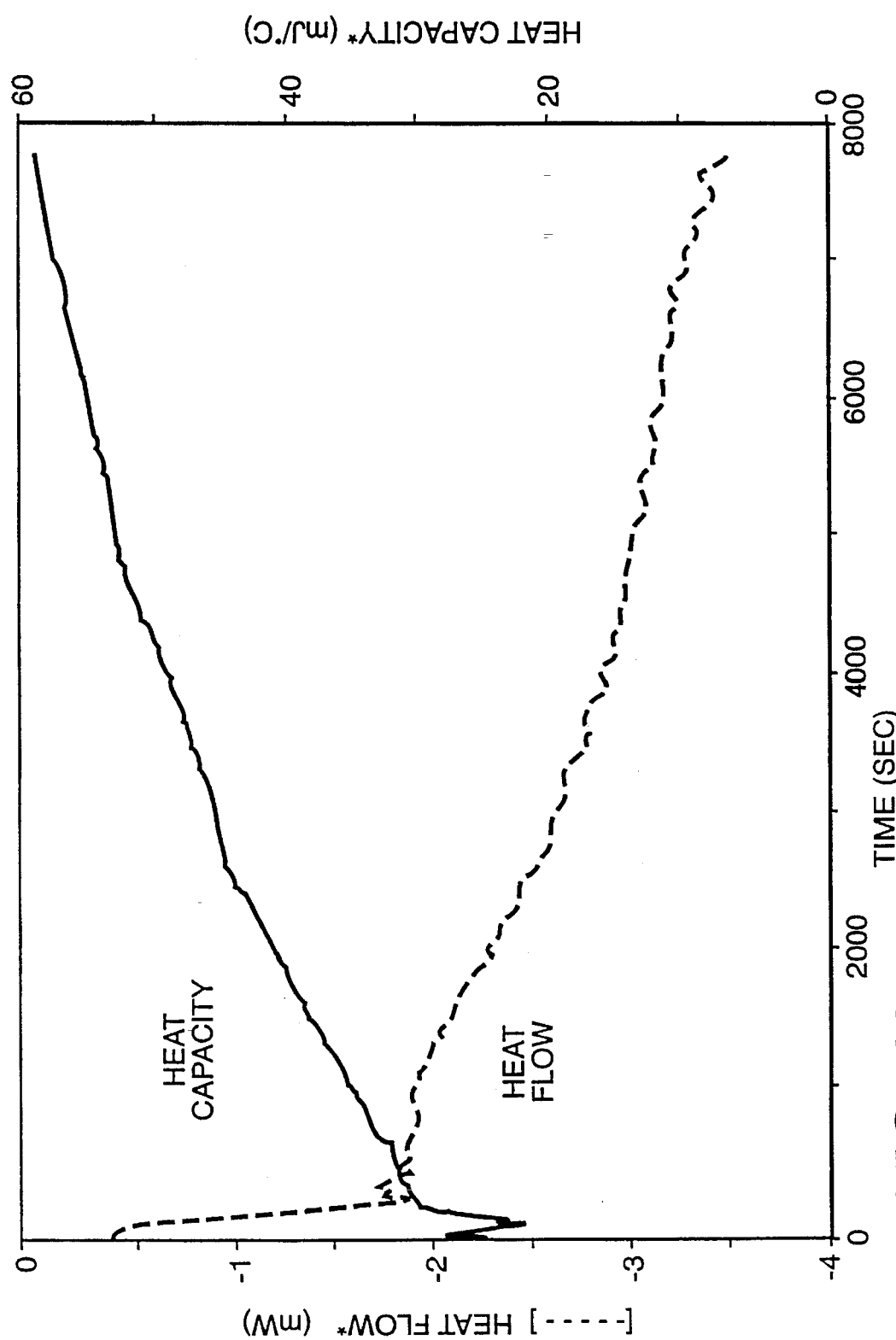
FIG. 11 is a plot of sapphire heat capacity and heat flow obtained using conventional DDSC.
Figure 12:
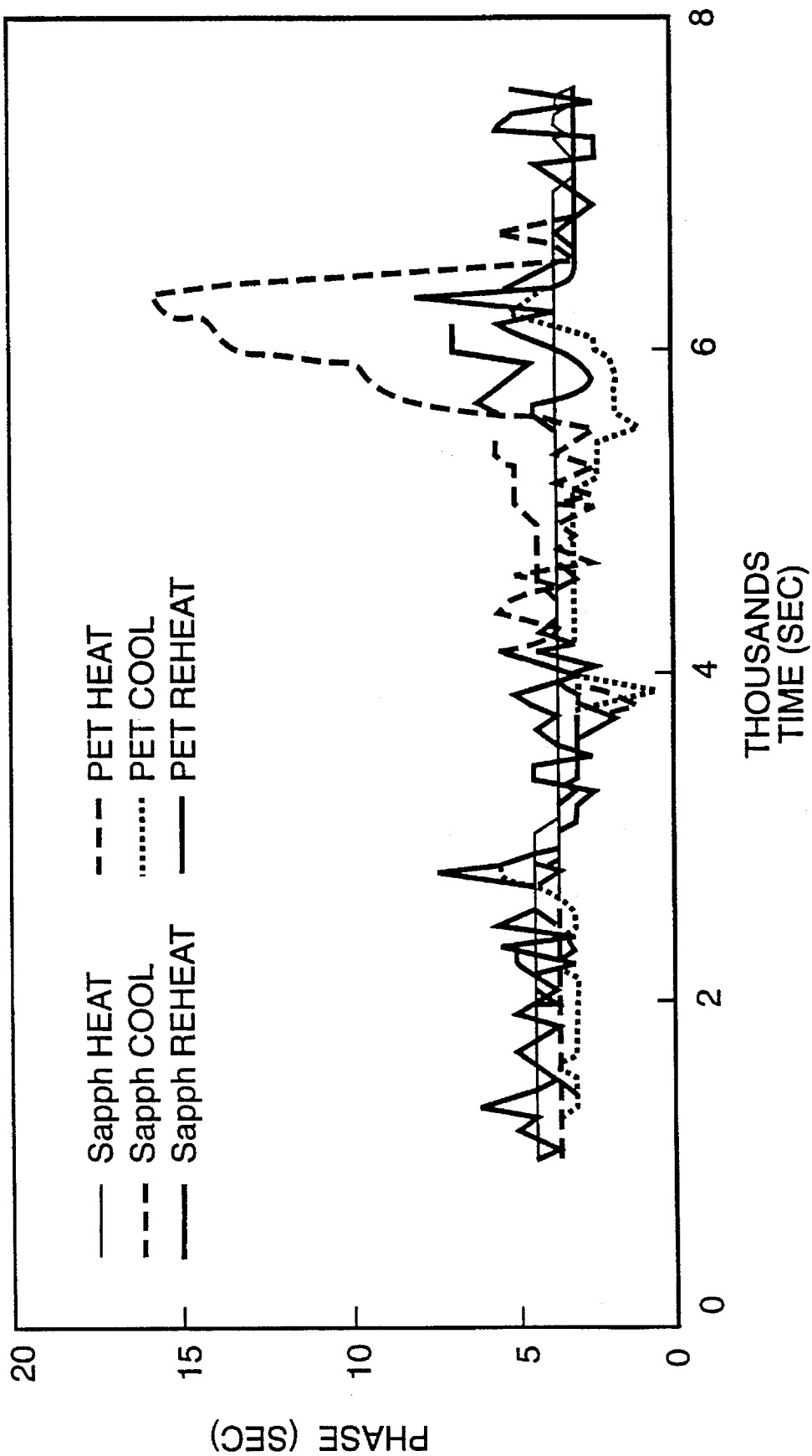
FIG. 12 is a plot of phase lag data for sapphire and PET.

The data from the run with sapphire in the sample pan were then similarly reduced. The results are shown in FIGS. 10 and 11. The three components are again very similar to each other, and have the same value as the heat capacity of sapphire obtained using conventional DDSC. The sapphire data was also fitted to second order polynomials. The phase lag data is shown in FIG. 12. Like the empty pan phase lag data, the sapphire phase lag data is relatively noisy.

Figure 13:
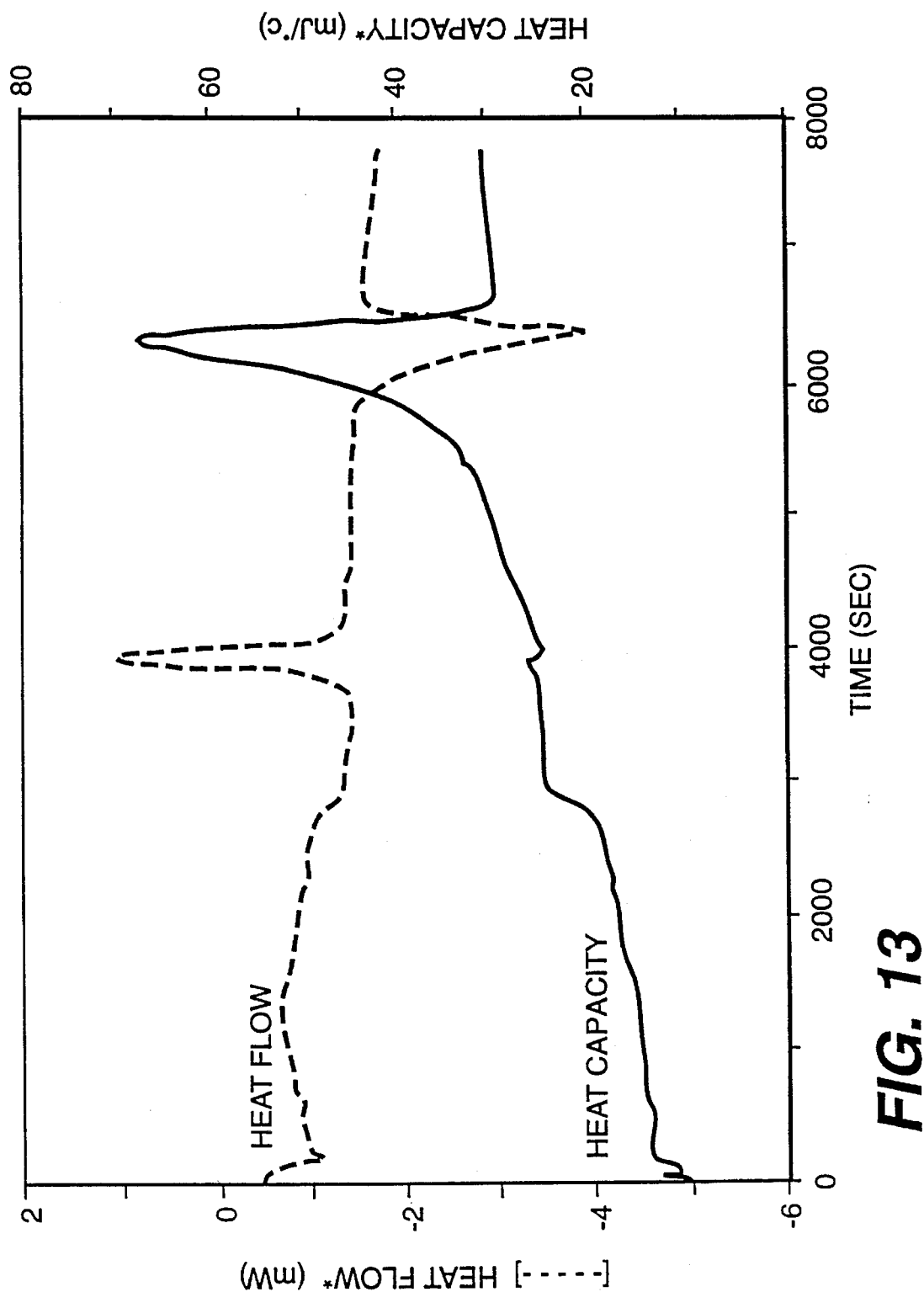
FIG. 13 is a plot of PET data obtained using conventional DDSC.
Figure 14:
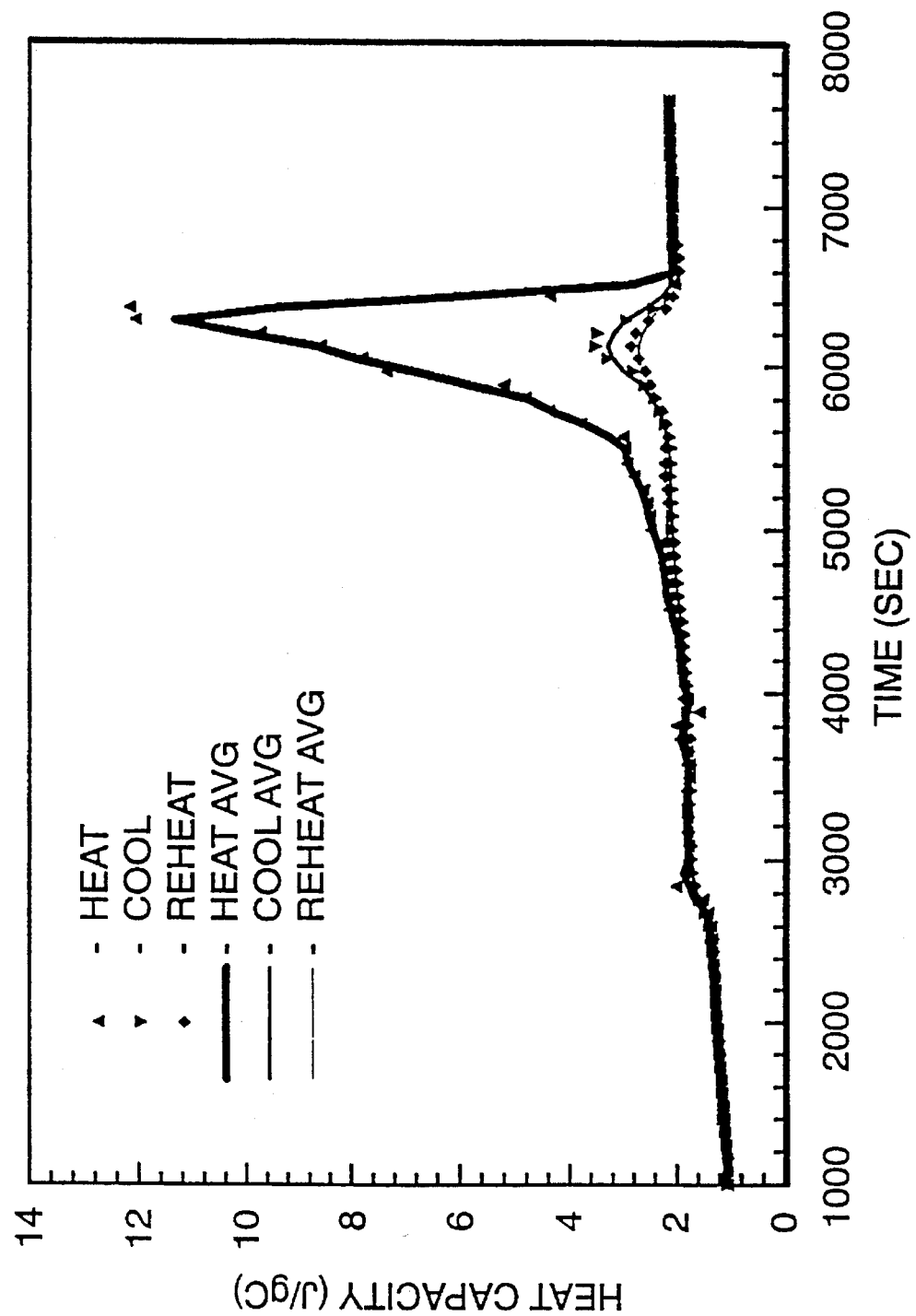
FIG. 14 is a plot of parsed PET heat capacities.
Figure 15:
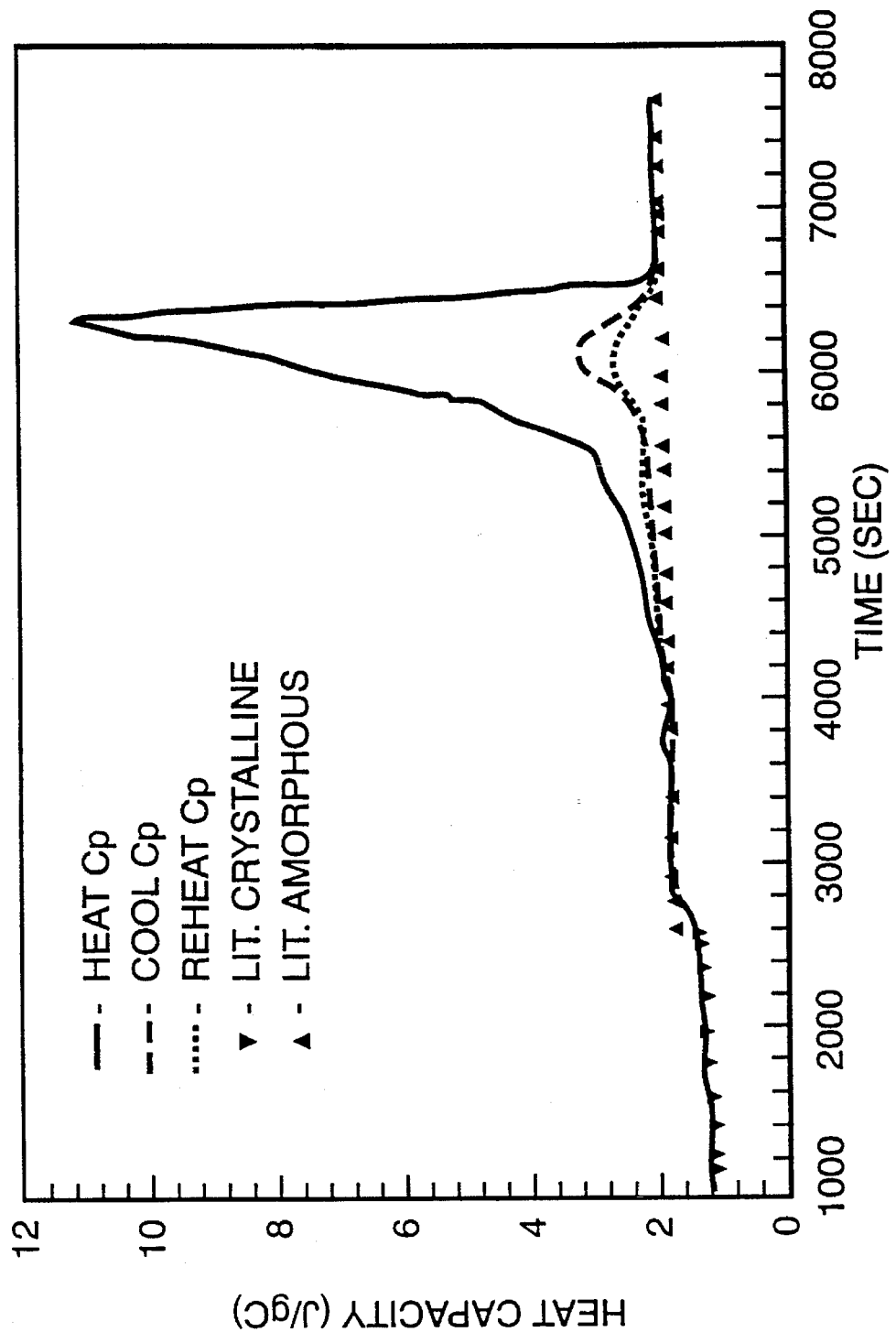
FIG. 15 is a comparison of calibrated PET heat capacity data with ATHAS recommended values.

The raw data from the run with PET in the sample pan, reduced using conventional DDSC techniques, is shown in FIG. 13 (see Table 13). A recrystallization peak can be seen in the heat flow data but not in the heat capacity data. The raw data was then reduced according to the present invention, i.e., it was parsed, analyzed and then calibrated over the whole temperature range using the polynomials calculated from the empty pan and sapphire runs. The resulting plots are shown in FIGS. 14 and 15. There is excellent agreement of the heating, cooling and reheating components within the glassy temperature range and within the melt temperature range. The observed values compare very favorably with the ATHAS recommended literature heat capacity values. The excellent agreement with the ATHAS values serves to justify the calibration methodology.

However, the most interesting feature is apparent in the transition from the solid state to the melted state at approximately 250° C. There is a considerable difference in the observed heat capacity at the solid-to-melt transition according to whether the PET sample is being heated, cooled, or re-heated. Thus the present invention can be a powerful tool for characterizing materials and classifying transitions.

EXAMPLE 2

The First Preferred Embodiment

This example illustrates the first preferred embodiment of the present invention, implemented using the programs listed in Appendix B. In this example, a helium purge of 25 cc/min was used to increase the accuracy of the heat capacity measurements. The sample was 16,934 mg of ICI Melinex PET which had been quench cooled to room temperature after a 10 minute isotherm at 270° C. It was analyzed from −30° to 330° C., ramping at 3° C./minute with modulation period 80 s and amplitude 2° C. The period used is the maximum permitted by the DSC2910 control software to ensure that there are as many points as possible in each cycle. The amplitude was set high so that each parset (heating, cooling or reheating) contained approximately the same number of points. Identical Empty pan and Sapphire runs were previously recorded to use in calibration.

Figure 16:
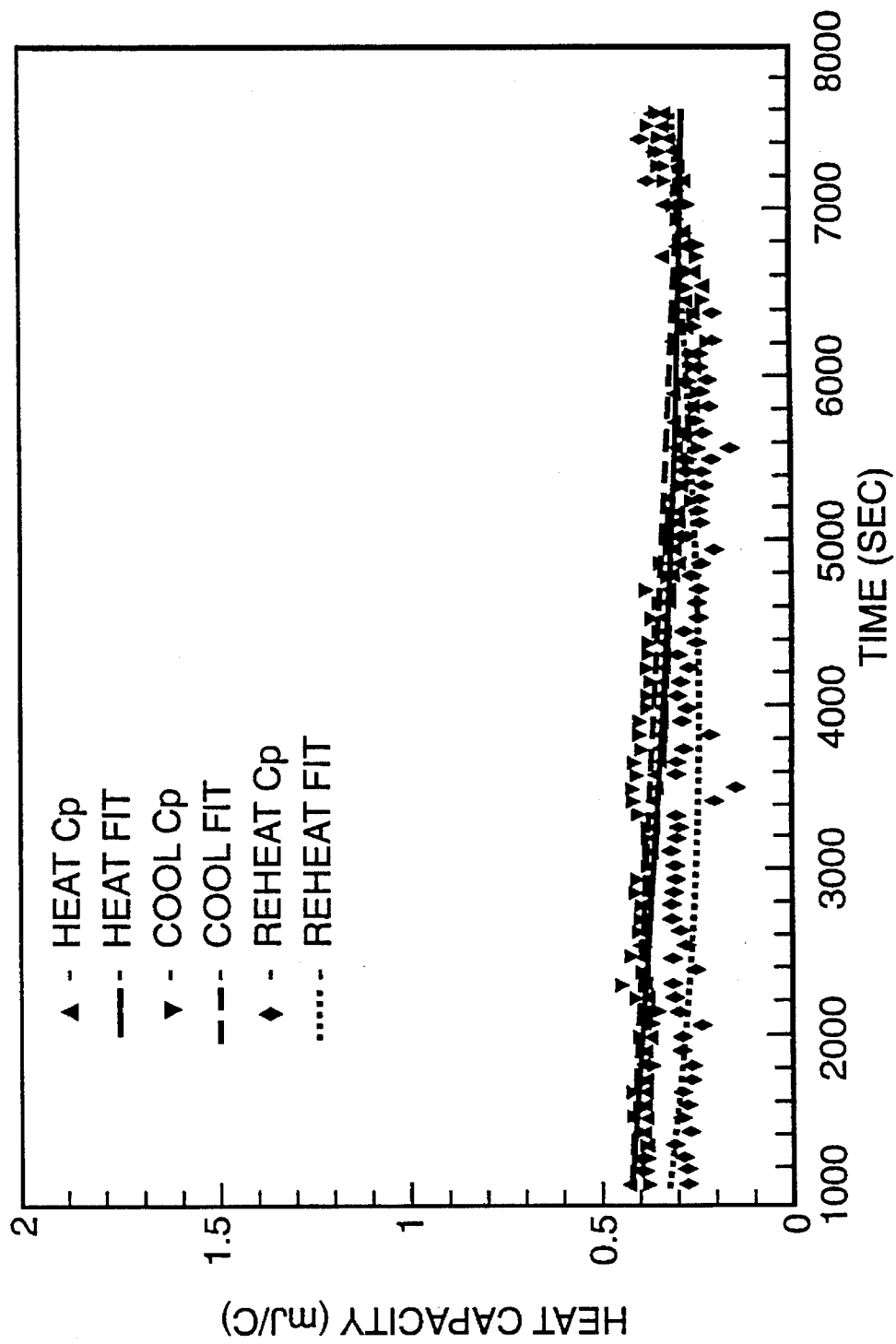
FIG. 16 is a plot of the heat capacities of an empty sample pan.
Figure 17:
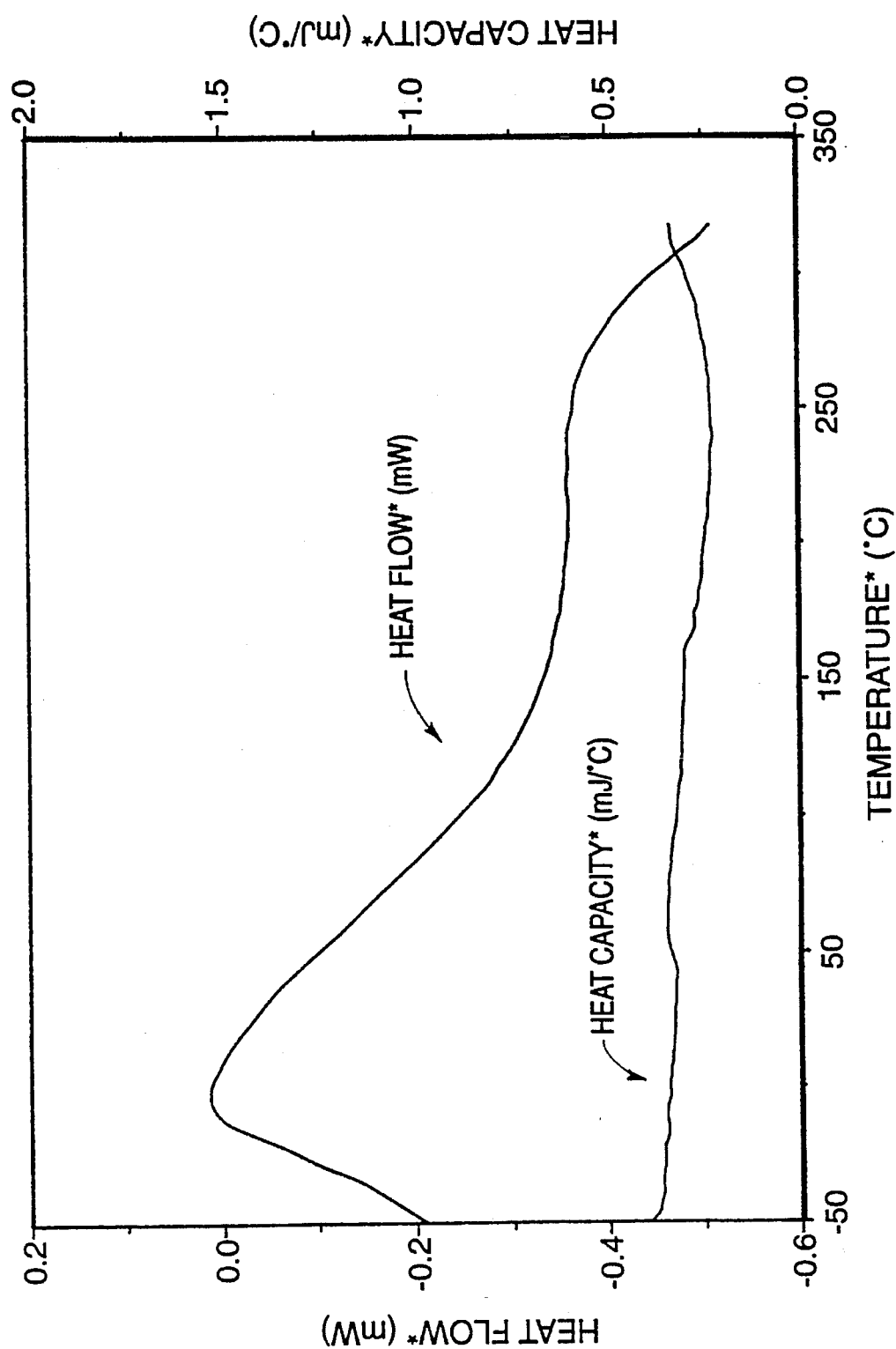
FIG. 17 is a baseline plot of heat capacity and heat flow.
Figure 18:
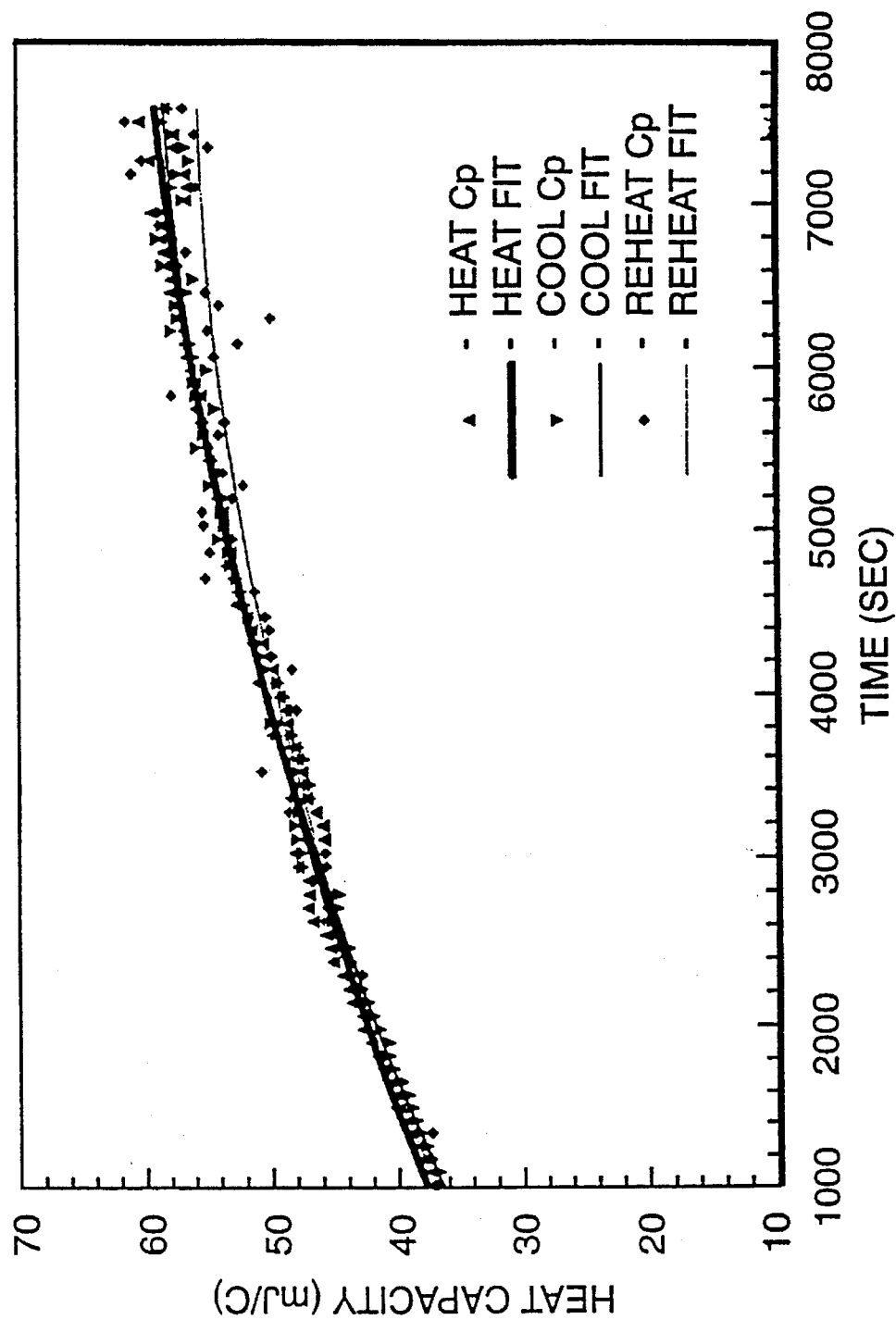
FIG. 18 is a plot of the heat capacities of a sapphire disk on heating, cooling and reheating.
Figure 19:
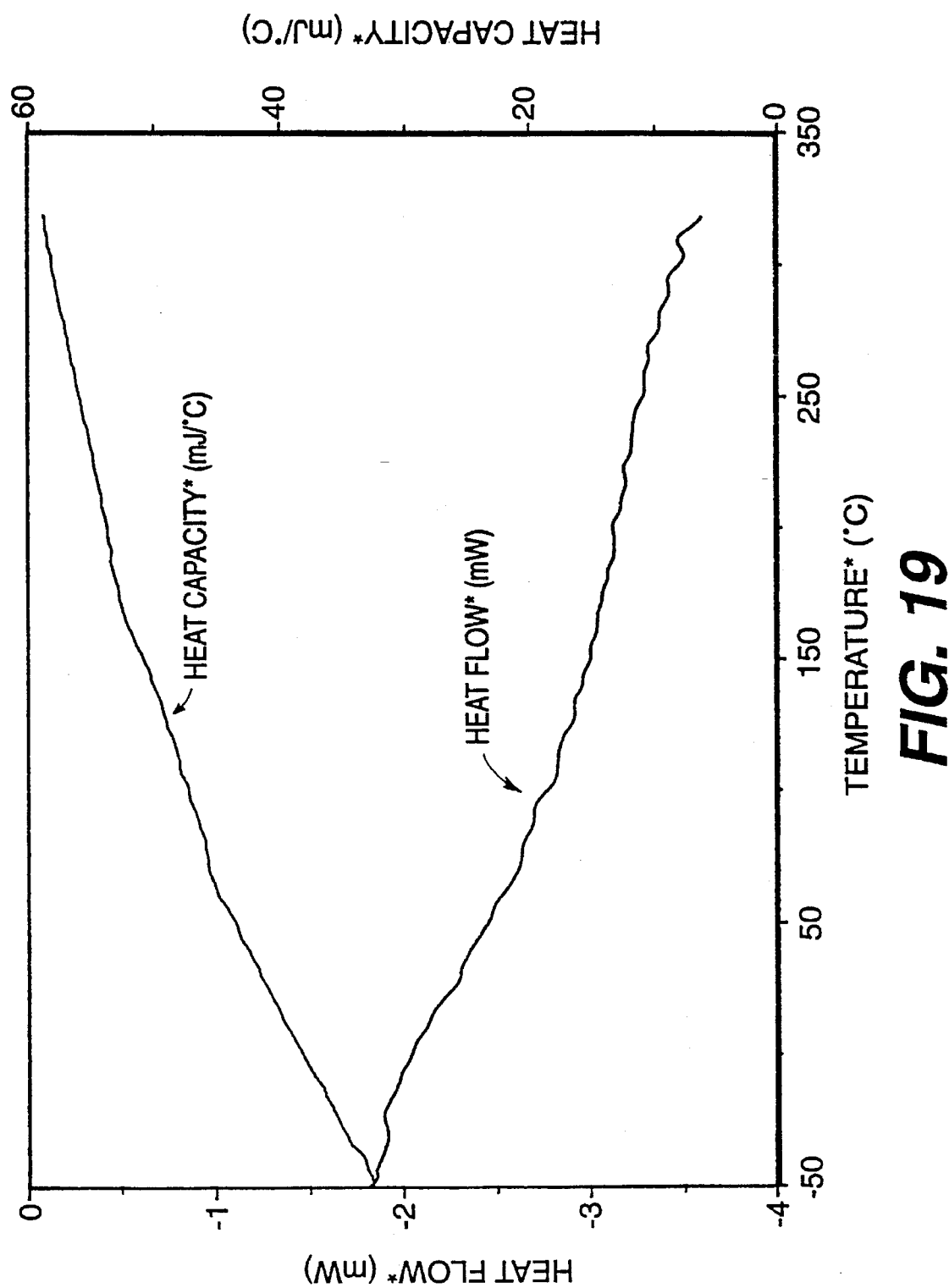
FIG. 19 is a plot of the heat flow and heat capacity of a sapphire disk.

The results for the empty pan run are shown in FIG. 16. The corresponding results calculated using the standard DDSC algorithm are shown in FIG. 17 (see Table 17). Heating, cooling and reheating give very similar results and they compare well with the conventional data. The three data sets were fitted to second order polynomials in preparation for calibration. Analysis of the sapphire measurement gave FIG. 18 and FIG. 19 (see Tables 18 and 19). Again the three components are very similar to one another and compare well with the standard results. The data sets were also fitted to second order polynomials for the calibration.

Figure 20:
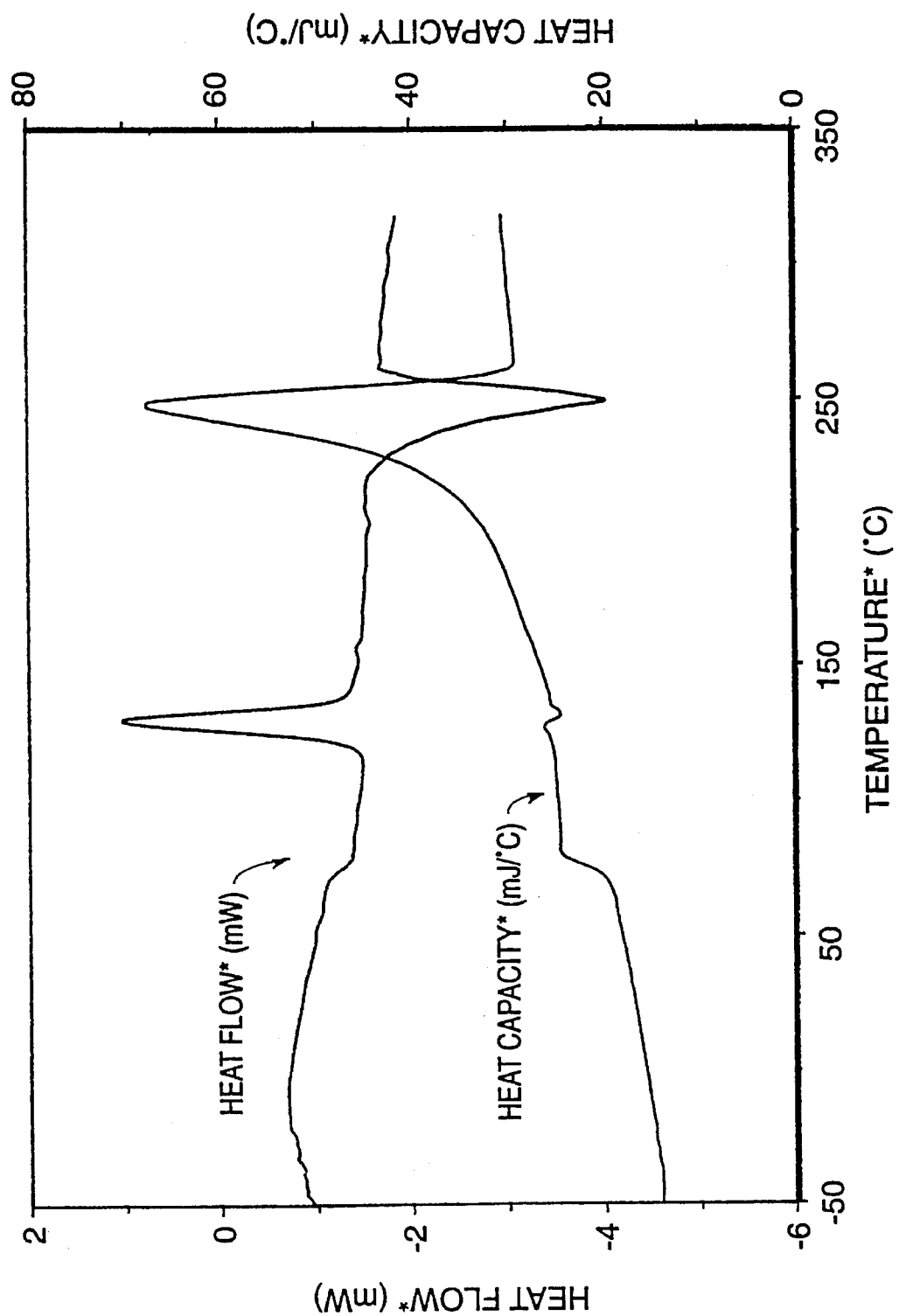
FIG. 20 is a plot of the heat flow and heat capacity of a PET sample.
Figure 21:
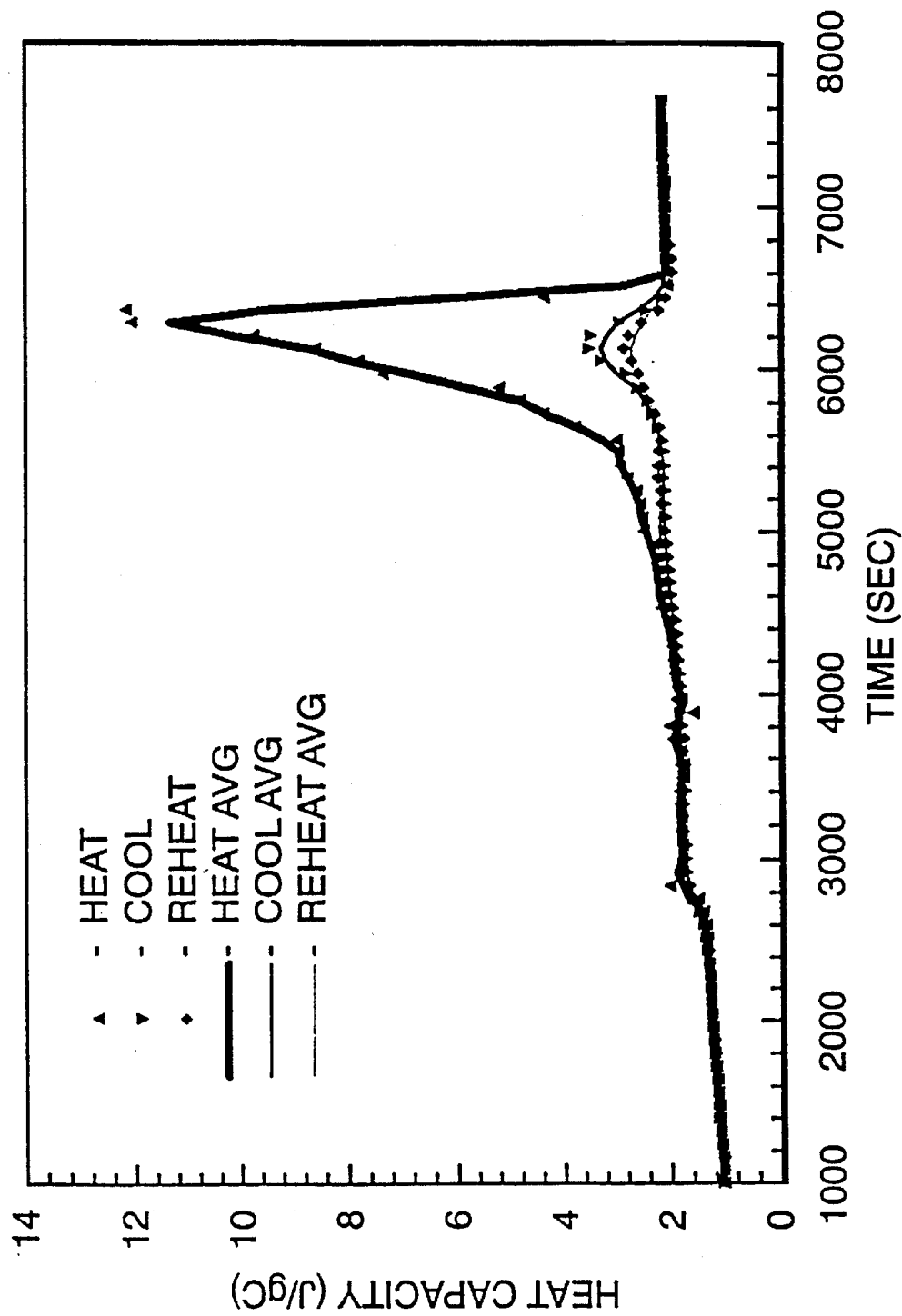
FIG. 21 is a plot of the heat capacities of a sample of quenched PET on heating, cooling and reheating.
Figure 22:
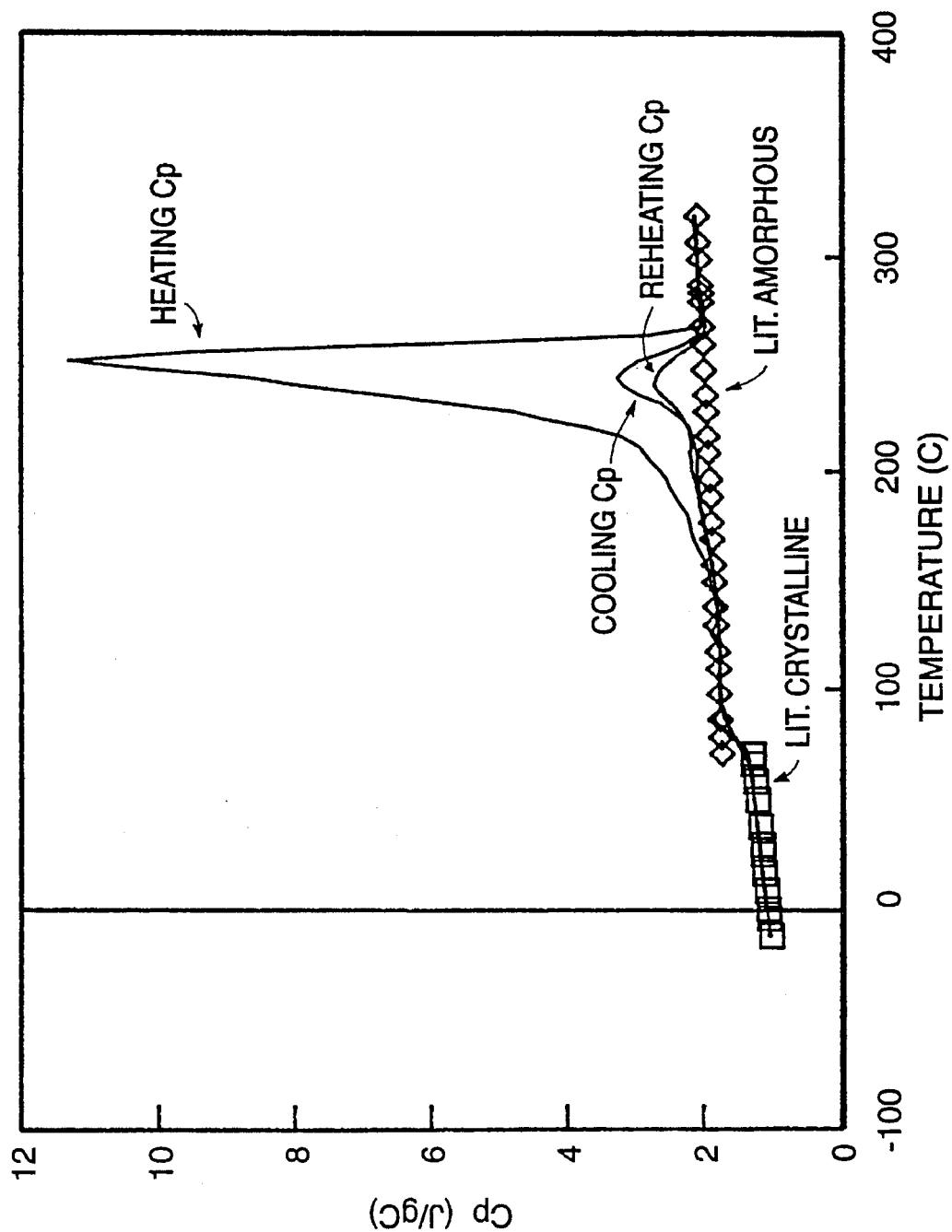
FIG. 22 is a comparison of parsed and literature data of the heat capacity of PET as a function of temperature.
Figure 23:
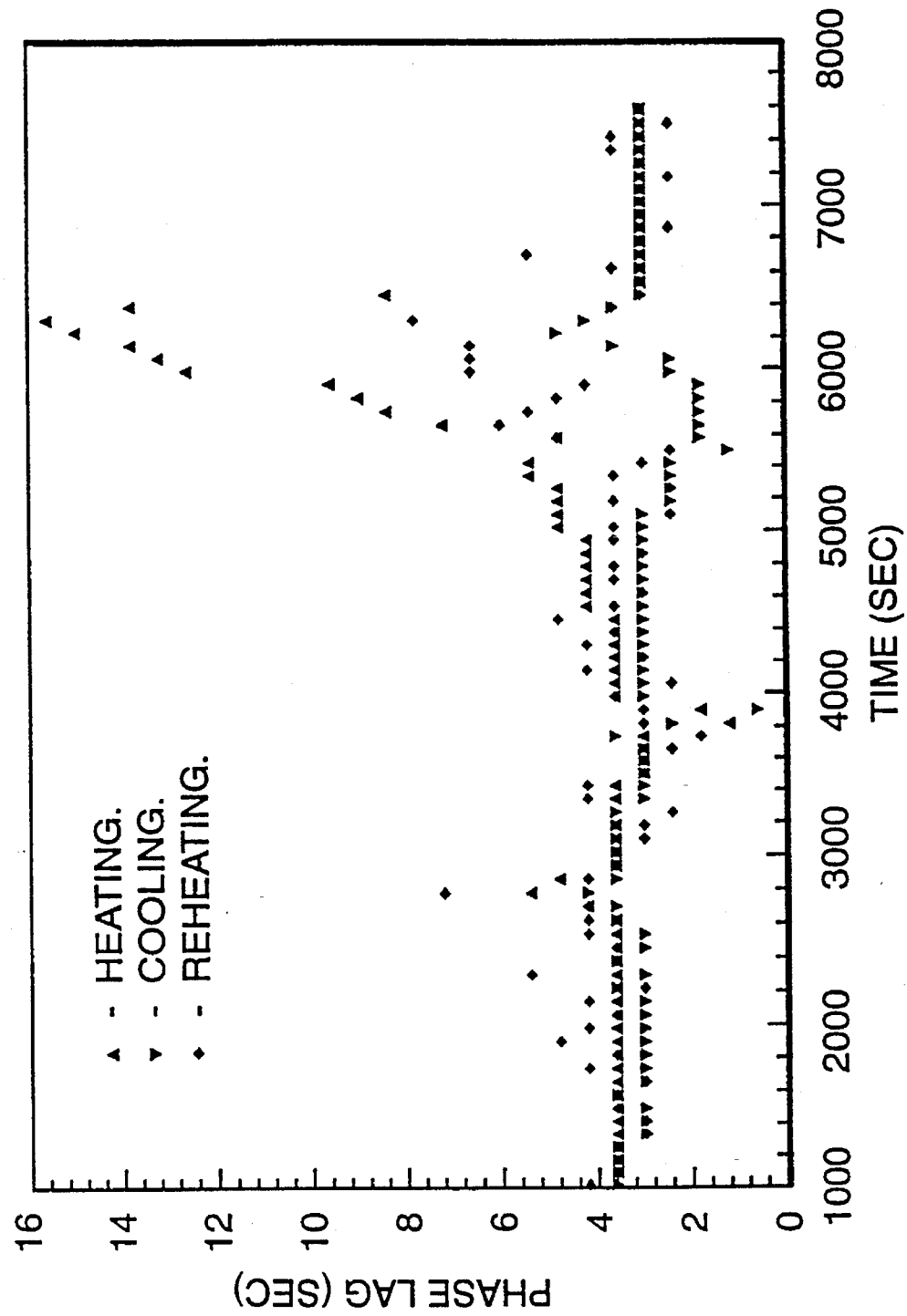
FIG. 23 is a plot of phase lag data of quenched PET on heating, cooling and reheating.
Figure 24:
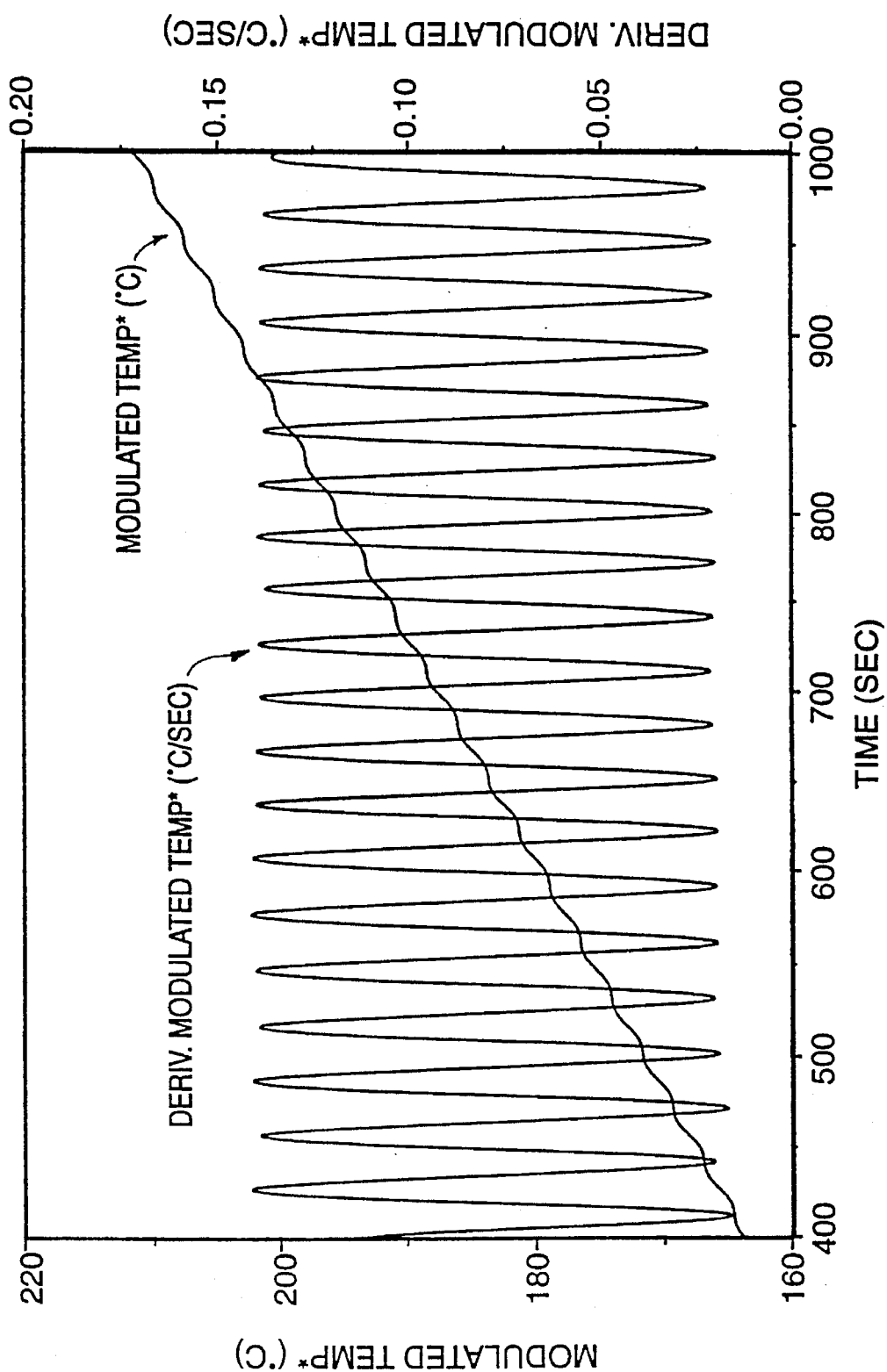
FIG. 24 is a plot of the modulated temperature and the derivative of the modulated temperature used in Example 3.

The data from the PET measurement without parsing is shown in FIG. 20 (see Table 20). A recrystallization peak is apparent in the heat flow data but not in the heat capacity data. The raw data was parsed, analyzed using the Qbasic programs and then calibrated over the whole temperature range using the polynomials calculated from the previous two measurements. The resulting plots show some interesting features (FIG. 21 and FIG. 22). As in the first example, there is an excellent agreement of the heating, cooling and reheating components within the glassy (−30 to 60° C.) and the melt (270° to 330° C.) regions of the temperature range. The observed values in these regions compare very favorable with the ATHAS recommended literature values, proving that the methods of analysis and calibration are valid. However, the most interesting feature is the difference in the heat capacities between the recrystallization temperature and the melt. There is a considerable asymmetry between the three different components—it is clear that the observed heat capacity is dependent upon whether the sample is being heated, cooled or reheated. The heat capacity is much higher when the sample is undergoing heating. The Phase Lag data which is calculated inherently when determining the heat capacity values is shown in FIG. 23. The data is very noisy and hence of limited usefulness but the same basic features are apparent agreement of the heating, cooling and reheating values except in the melt where they are very different. It is also that the Cooling phase actually decreases through the melt showing that the process is exothermic.

EXAMPLE 3

The Second, Third and Fourth Preferred Embodiments

The second, third and fourth preferred embodiments of the present invention were implemented using a sample of quenched PET over the temperature range 130° to 330° C. at 5° C./min with a modulation period of 30 seconds and an amplitude of 0.2° C. The heating rate and modulation parameters were chosen such that the sample only undergoes heating.

Figure 25:
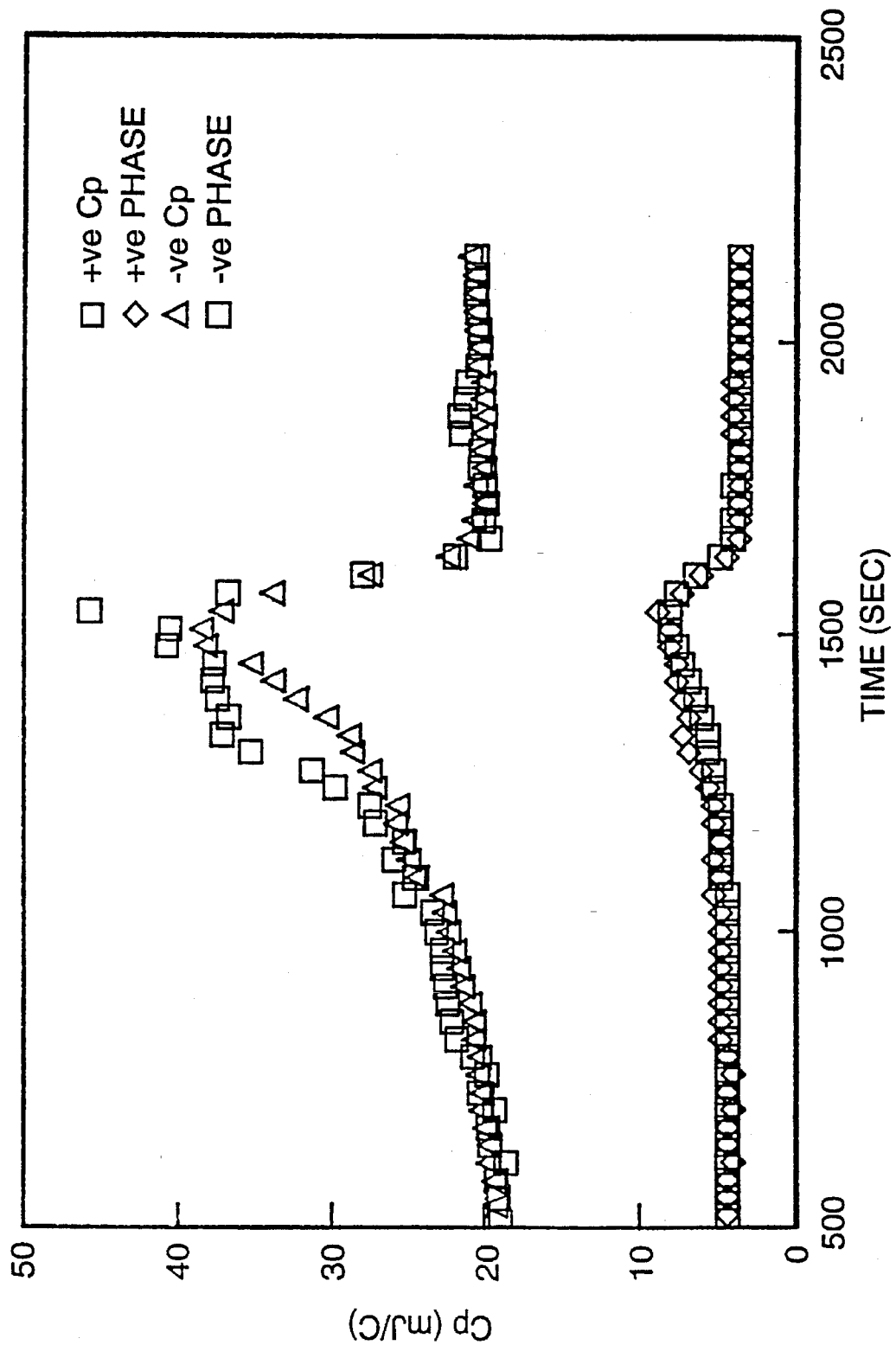
FIG. 25 is a plot of the heat capacities and phase lag of quenched PET parsed according to cyclic modulated temperature.
Figure 26:
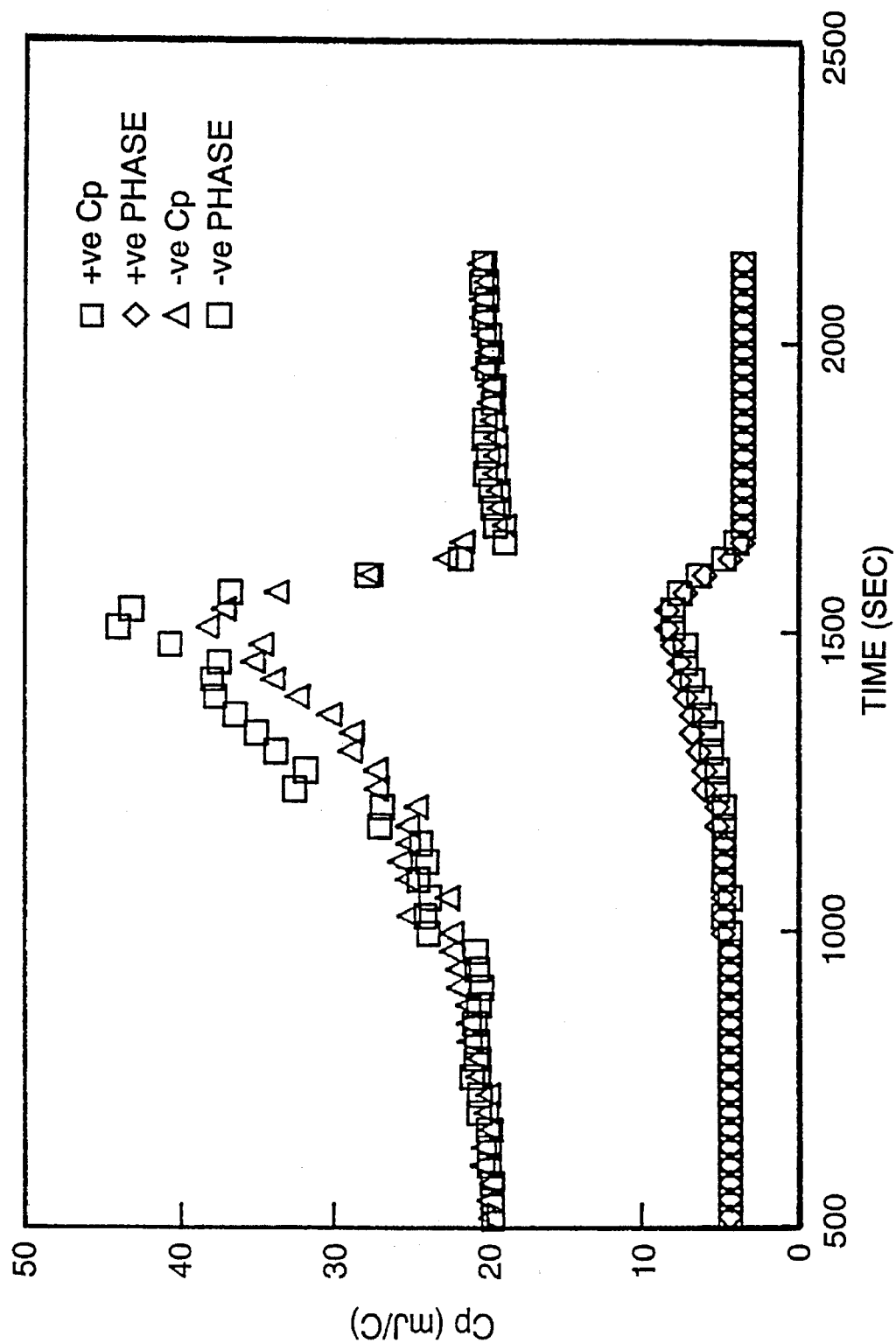
FIG. 26 is a plot of the heat capacities and phase lag of quenched PET parsed according to cyclic heat flow.
Figure 27:
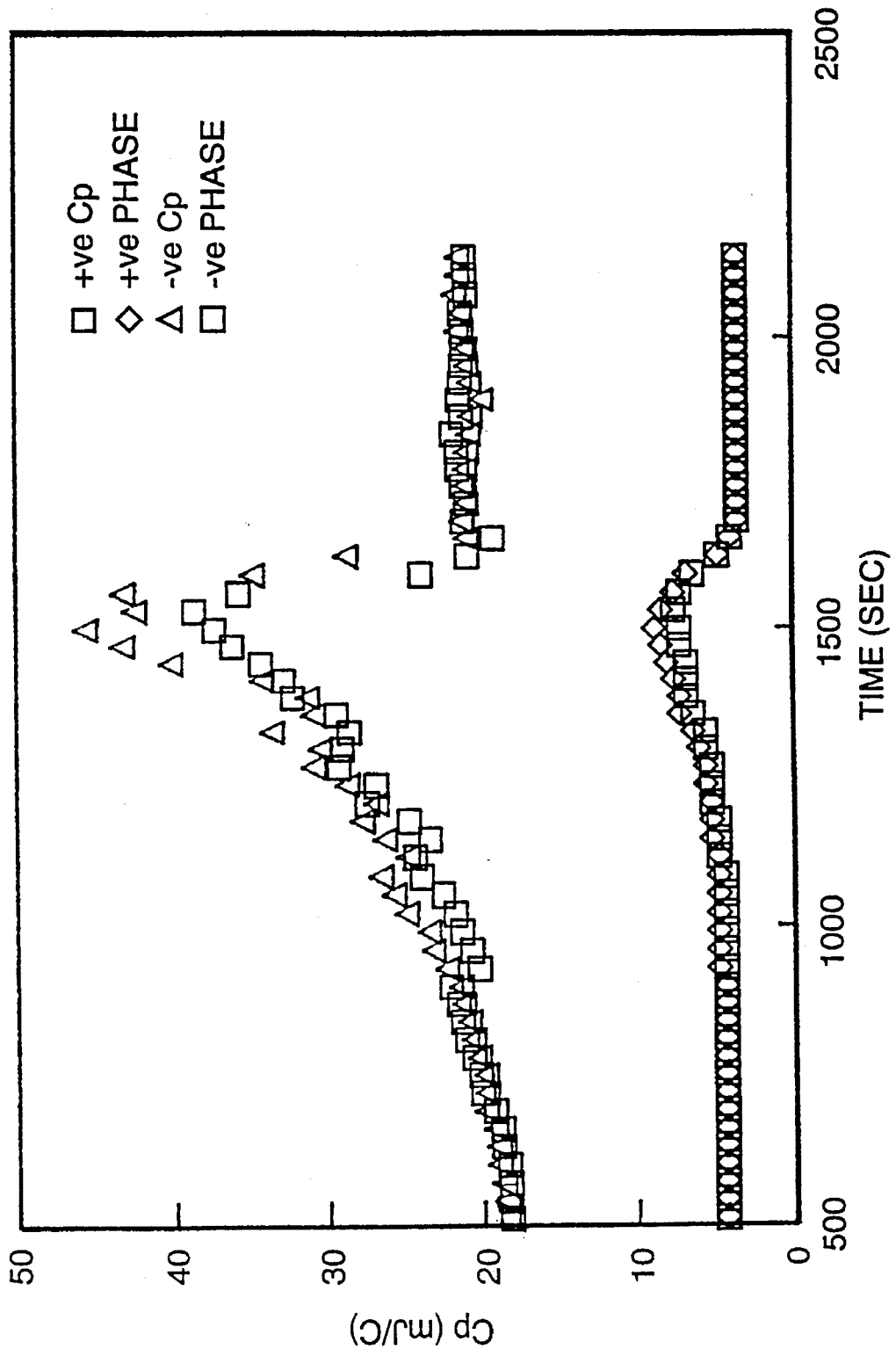
FIG. 27 is a plot of the heat capacities and phase lag of quenched PET parsed according to cyclic derivative modulated temperature.

The results are shown in FIG. 25, FIG. 26 and FIG. 27 (see Tables 26 and 27). Again, there is good agreement and symmetry above the melting peak. However, in this Example the agreement extends from the recrystallization temperature through to the melt as well. This trend is especially apparent in the Phase Lag data when compared to the measurement shown in Example 2. The heat capacity data, however, shows that the result is not perfectly symmetrical, although it exhibits great improvement compared to the measurement of Example 2, in which the sample was allowed to cool.

EXAMPLE 4

Multiplexed DDSC Theory

The heat flow in a standard DDSC measurement is given by:

$$\frac{dQ}{dt} = -(b + A\omega \text{Cos}\omega t)C_p + C\text{Sin}\omega t + f'(t,T)$$

where:

dQ/dt is the modulated heat flow;

b+Aω Cos ωt is the derivative of the modulated temperature;

f'(t,T) is the average underlying kinetic function;

$C_p$ is the heat capacity;

C is the amplitude of the kinetic response to the sine wave modulation.

The first two terms are measured quantities. The third term is automatically removed during the deconvolution process. This leaves the last two terms as the unknowns in the heat flow equation. Because there are two modulations in a multiplexed measurement, there will be two sets of equations. The unknown values can therefore be calculated from the simultaneous equations, including the amplitude C of the kinetic response to the sine wave modulation. This analysis should increase the understanding of kinetics during melting of semi-crystalline polymers. Because the two equations are obtained from the same measurement (and sample), the scope for error in these analyses is greatly reduced.

Also, frequency dependent heat capacities obtained at two or more frequencies can be extrapolated to the theoretical value for an infinitely high modulation frequency. This would then provide the true baseline for this type of melting.

Programming Multiplexed DDSC

Figure 28:
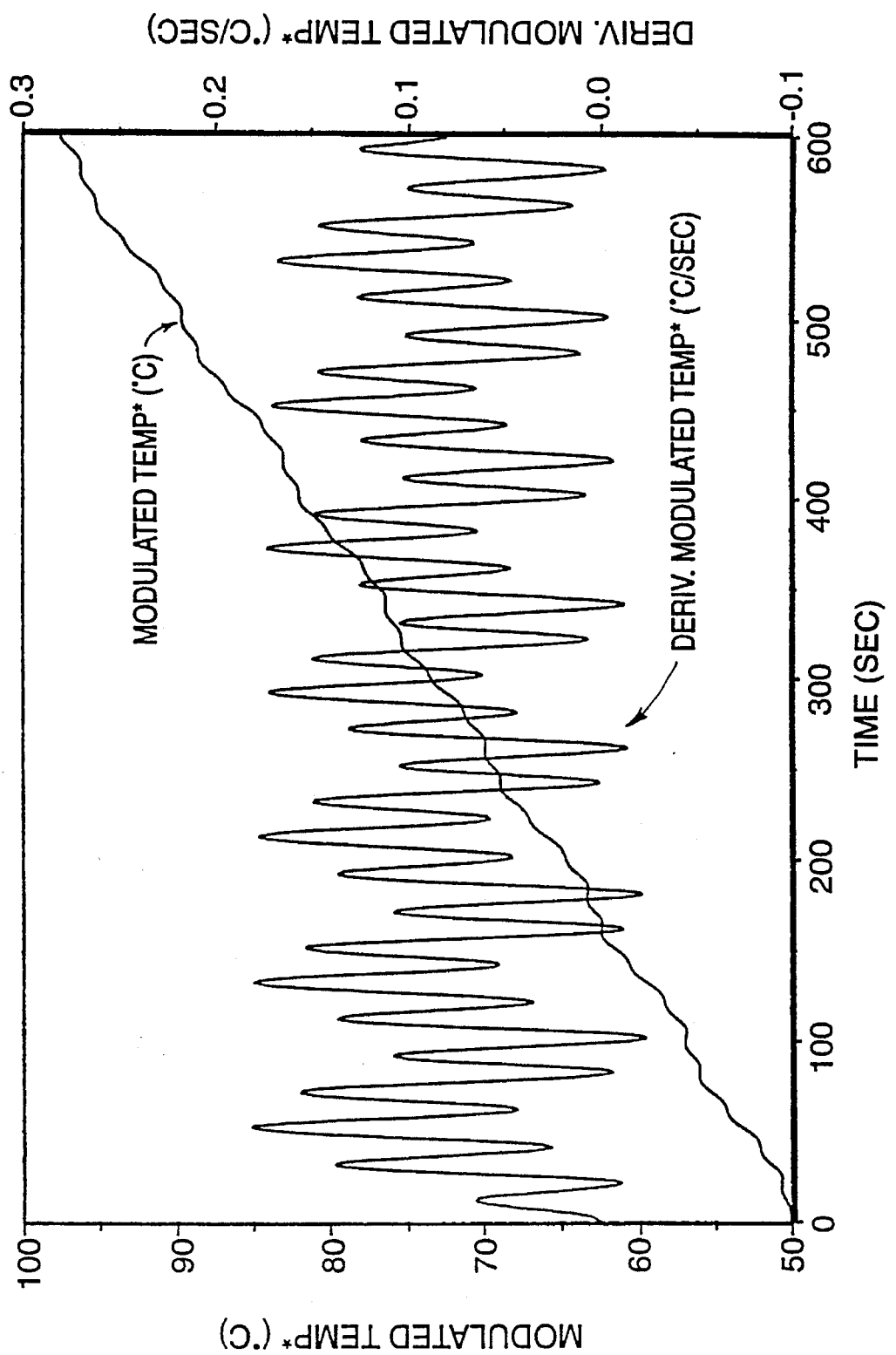
FIG. 28 is a plot of a multiplexed temperature profile and the derivative of the modulated temperature.
Figure 29:
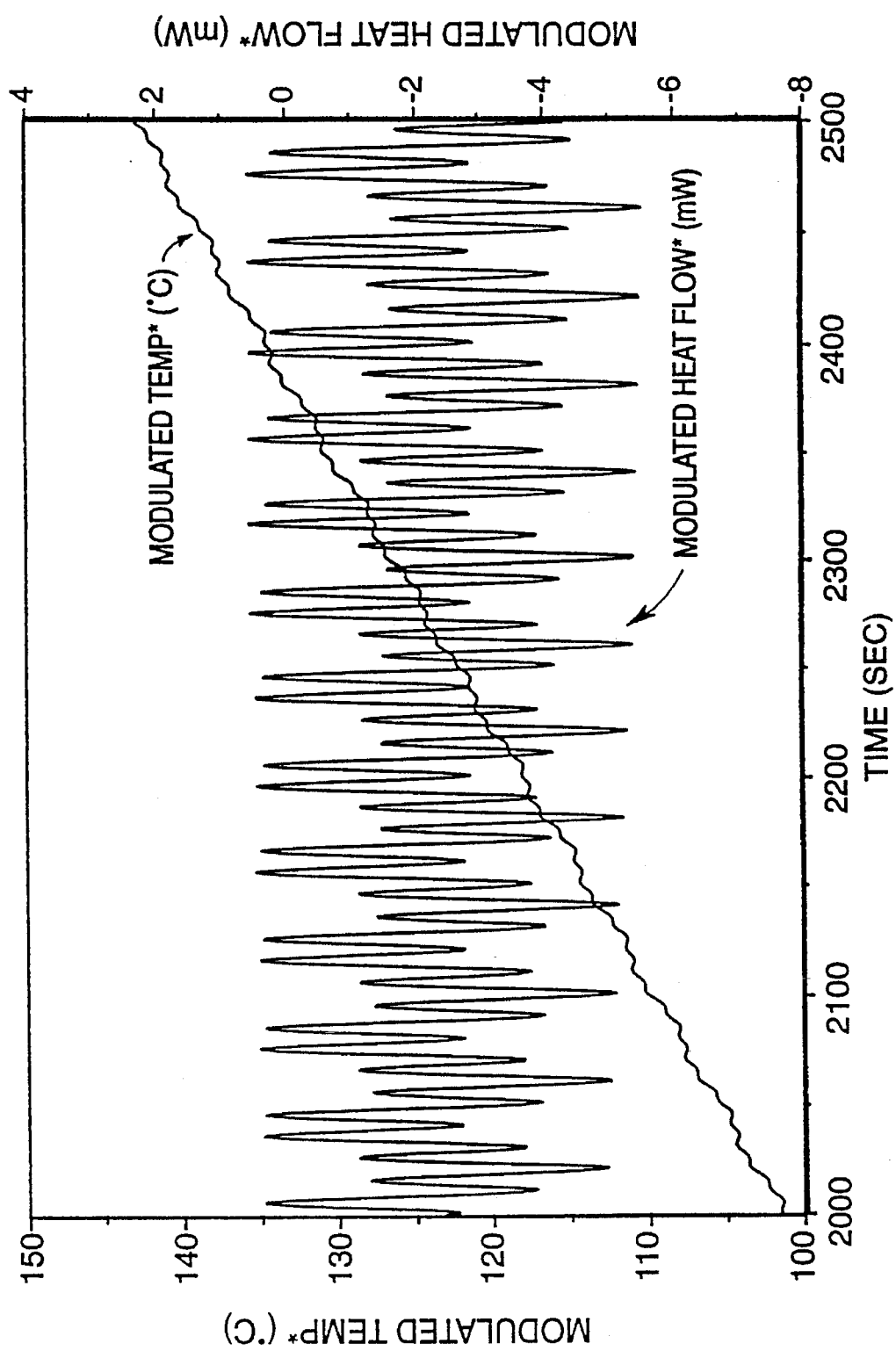
FIG. 29 is a plot of another multiplexed temperature profile and corresponding sample response.

Examples of multiplexed DDSC temperature profiles are shown in FIGS. 28 and 29 (see Tables 28 and 29). The primary modulation was controlled using the method editor on a TA Instruments Thermal Analyst 2000. The secondary modulation parameters were set using special Q-commands which allow direct communication with the module itself. These commands are set as multipliers of the primary modulation parameters. For example, when the primary modulation period is set at 30 seconds and the period Q-command is set at 3, then the secondary modulation period would be 90 seconds.

In some cases the parameters chosen require the cell to operate under extreme conditions, i.e., short periods and high amplitudes. In those cases, helium must be used as a purge gas, because it is a much better conductor of heat than nitrogen. Helium also has the added advantage of reducing any thermal conductivity errors that may be present due to the size and shape of the sample.

The data was converted to ASCII format using the TAGET and TAB2A commands available in RMX File Utilities. It was then imported into LOTUS 1-2-3 where the required data, Time (seconds), Modulated Temperature (°C.) and Modulated Heat Flow (mW), were selected and printed to another file for analysis.

The analysis program was developed using standard DDSC deconvolution software. In the program, the modulations are smoothed out over a complete cycle to provide the underlying signals and the amplitudes of these modulations are used along with a generated reference sine angle to calculate the heat capacity data. These processes are contained within the following four sub-programs:

1/ FTMPLX1.BAS—This sub-program uses the Lotus file containing Time (seconds), Multiplexed Temp (°C.) and Multiplexed Heat Flow (mW). It queries the user for the experimental and analysis parameters and then averages the multiplexed signals at the primary (shorter) modulation period to leave the secondary (longer) period modulation (FIG. 30; Table 30). The irregular form of the Heat Flow data is explained below.

Figure 31:
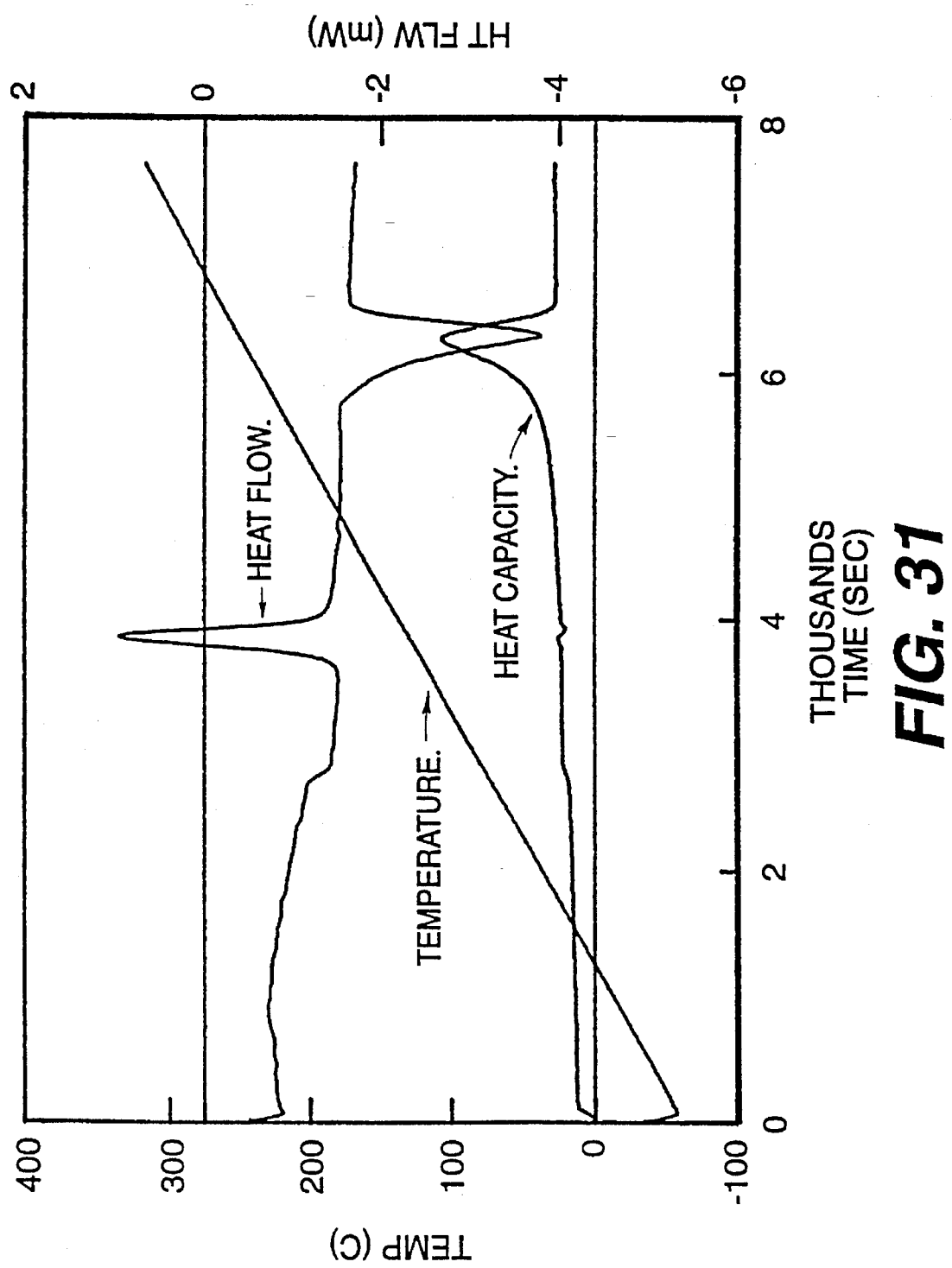
FIG. 31 is a plot of the data of FIG. 30 after a second deconvolution.

2/ FTMPLX2.BAS—This sub-program uses the output from FTMPLX1. It averages at the secondary modulation period to obtain the underlying data. A Reference Sine Angle is generated and from the secondary modulation Temperature and Heat Flow amplitudes it calculates the Heat Capacity. Time, Underlying Temperature, Underlying Heat Flow and Heat Capacity are written to a file at user defined intervals ready for analysis in a LOTUS spreadsheet (FIG. 31; Table 31).

3/ FTMPLX3.BAS—This sub-program uses the original LOTUS file and the output from FTMPLX1. It checks the alignment in time of the two files and then proceeds to subtract the secondary modulation Temperature and Heat Flow data from the respective multiplexed data. This leaves the cyclic component of the primary modulation (FIG. 32; Table 32) which is also combined with a generated Reference Sine Angle to calculate the Temperature and Heat Flow amplitudes and hence the primary modulation Heat Capacity (FIG. 33; Table 33).

4/ FTMPLX4.BAS—This sub-program uses the output from FTMPLX3. The primary modulation Heat Capacity contains a dependence upon the secondary modulation so this program averages again over the longer modulation period. Time, Averaged Heat Capacity and the Amplitude of this dependence are written to a file at the user defined intervals for analysis in the LOTUS spreadsheet (FIG. 34; Table 34).

Figure 34:
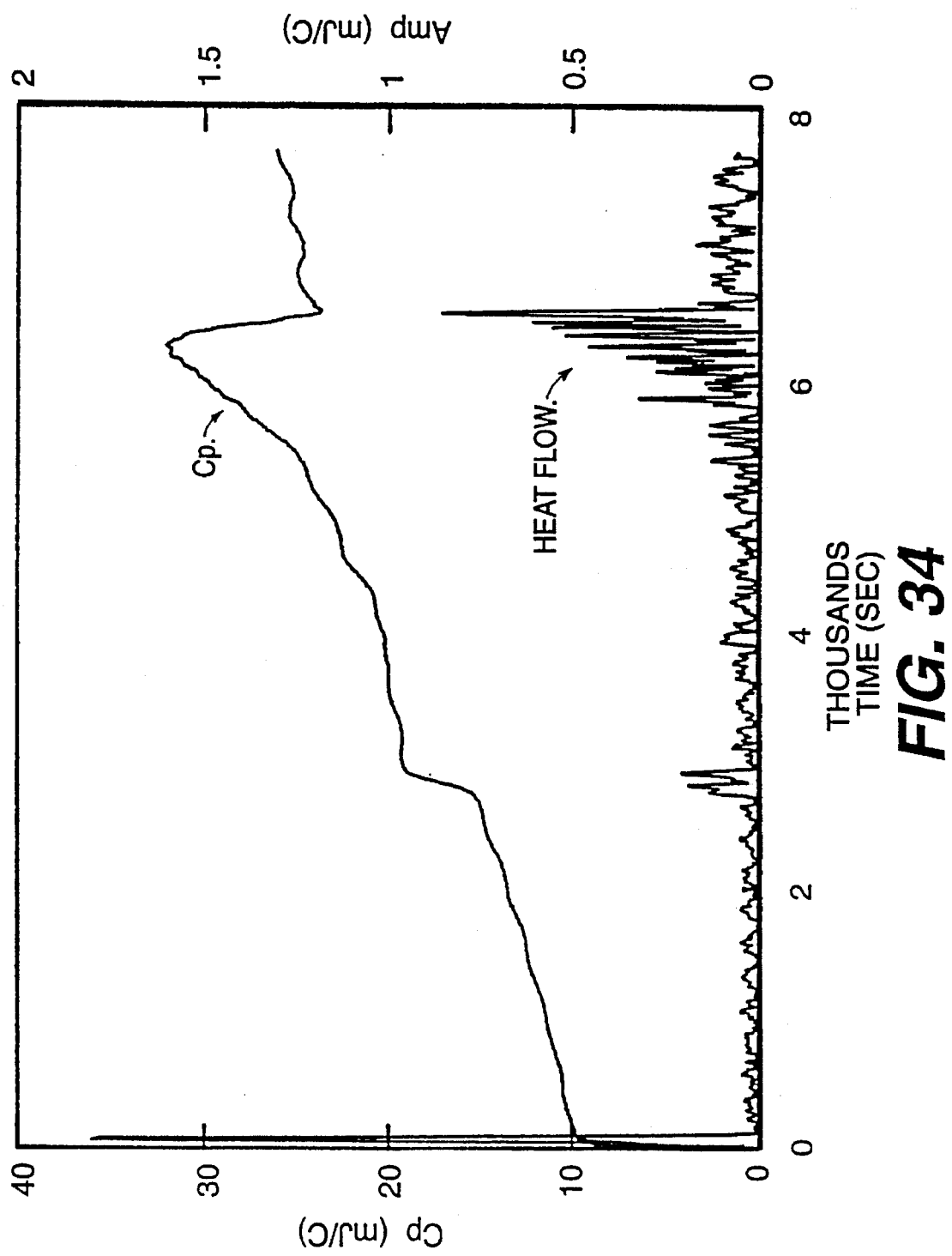
FIG. 34 is a plot of the heat capacity after removal of the secondary period.

Analysis of the primary modulation showed a dependence upon the secondary (longer) modulation period which necessitated the final Fourier transform process, i.e., the primary heat capacity is averaged over the secondary period to get the smooth results. This allows access to the amplitude of this dependence. The results, as shown in FIG. 34 (see Table 34), show a near zero dependence over the whole temperature range with the exception of the melt and possibly the glass transition. This observation is surprising and demonstrates that there may be information present in a multiplexed measurement that cannot be obtained from two separate DDSC measurements.

Data Collection Rate

Figure 30:
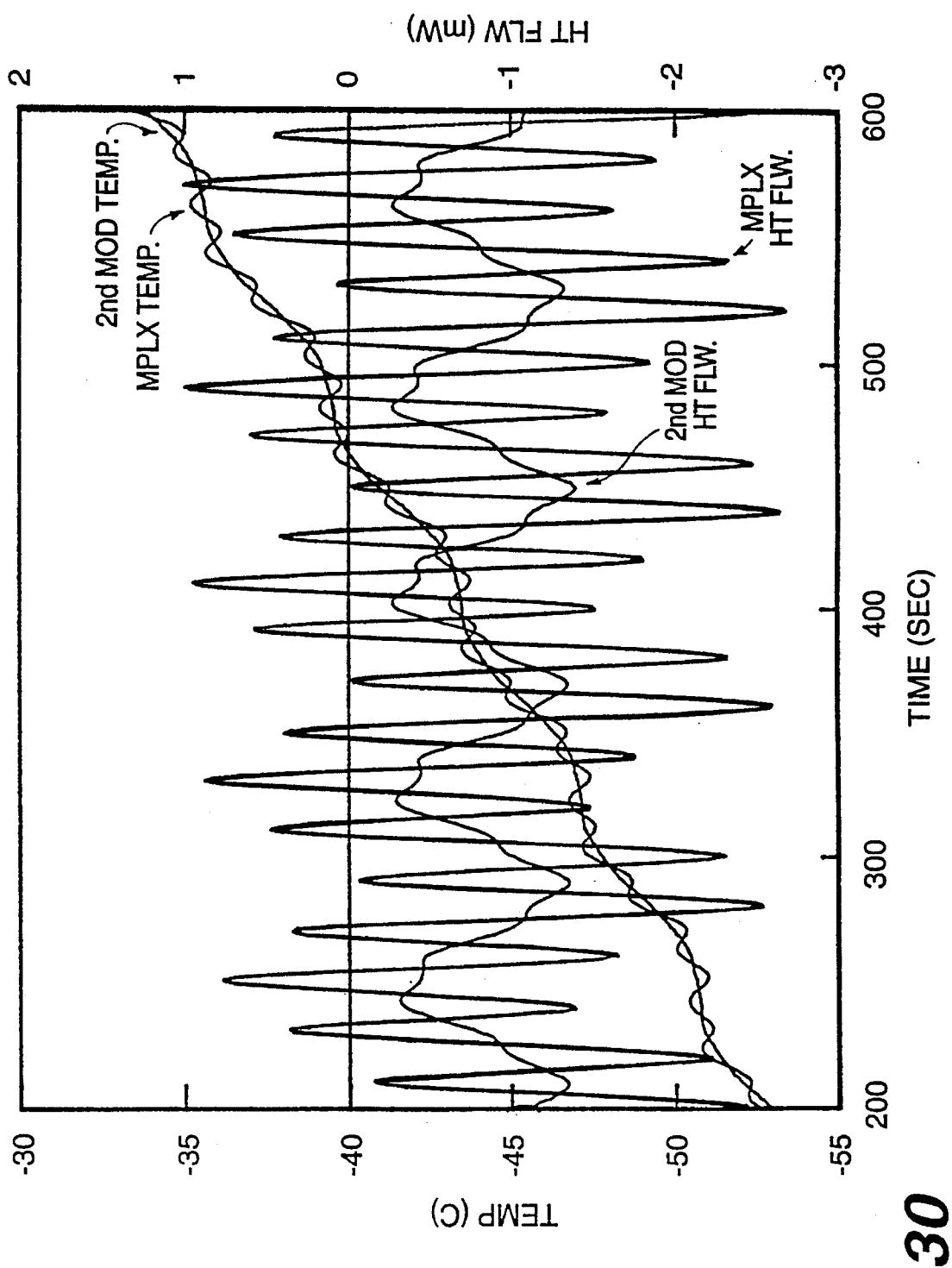
FIG. 30 is a plot of multiplexed data and once-deconvoluted data.

If the data collection rate of the instrument is not consistent, such that the Fourier transform analysis of the data does not take place over precise modulation cycles, the resulting data is distorted, as shown in FIG. 30 (see Table 30). The magnitude of this distortion depends upon the data collection rate and the period as set by the operator and is not significant in standard DDSC measurements. For example, it is of the order of up to 1 second/cycle in a 40 second period measurement with a data sampling rate of 2 seconds/point. Fourier transforming a single modulation produces a 'straight' line with comparatively slow changes in magnitude, in which any slight variations from the ideal are not noticeable.

In Multiplexed measurements this error becomes significant because the result of the Fourier transformation is a rapidly changing sine wave signal which amplifies the effect of any slight irregularities. Because the primary modulation is calculated from the multiplexed data minus the distorted secondary modulation data, the errors are carried through and could generate noise in the primary heat capacity data.

As shown in the Figures discussed below, the heat capacities obtained using multiplexed DDSC agree with each other, but not with the ATHAS recommended literature values.

Applications

The advantage of multiplexing is that it enables the investigator to study the sample response to more than one frequency in a single measurement. This not only saves time but also avoids discrepancies that might arise from differences between different samples. Our evidence to date suggests melting transitions are strongly frequency dependent whereas other transitions are not. This is clearly evident in the PET example shown in FIGS. 35 and 36 (see Tables 35 and 36). This additional information is useful, therefore, in assigning events and more clearly delineating where a melting event starts.

Multiplexed DDSC Measurements

Multiplexed DDSC measurements were carried out on a TA Instruments DSC2910 Differential Scanning Calorimeter. The sample was 16.934 mg of ICI Melinex PET which had been quench cooled after isotherming at 270° C. for 10 minutes. It was heated from −60° to 330° C. at 3° C./minute with a primary modulation period of 20 seconds and an amplitude of 0.2° C. The multipliers were set at 4 and 0.2 respectively, giving a secondary modulation with a period of 80 seconds and an amplitude of 0.04° C. Temperature amplitude control was turned off to enable the cell to achieve the complex modulation. Identical measurements were also run on an empty pan and on a sapphire disk to use in calibration (see above).

Figure 35:
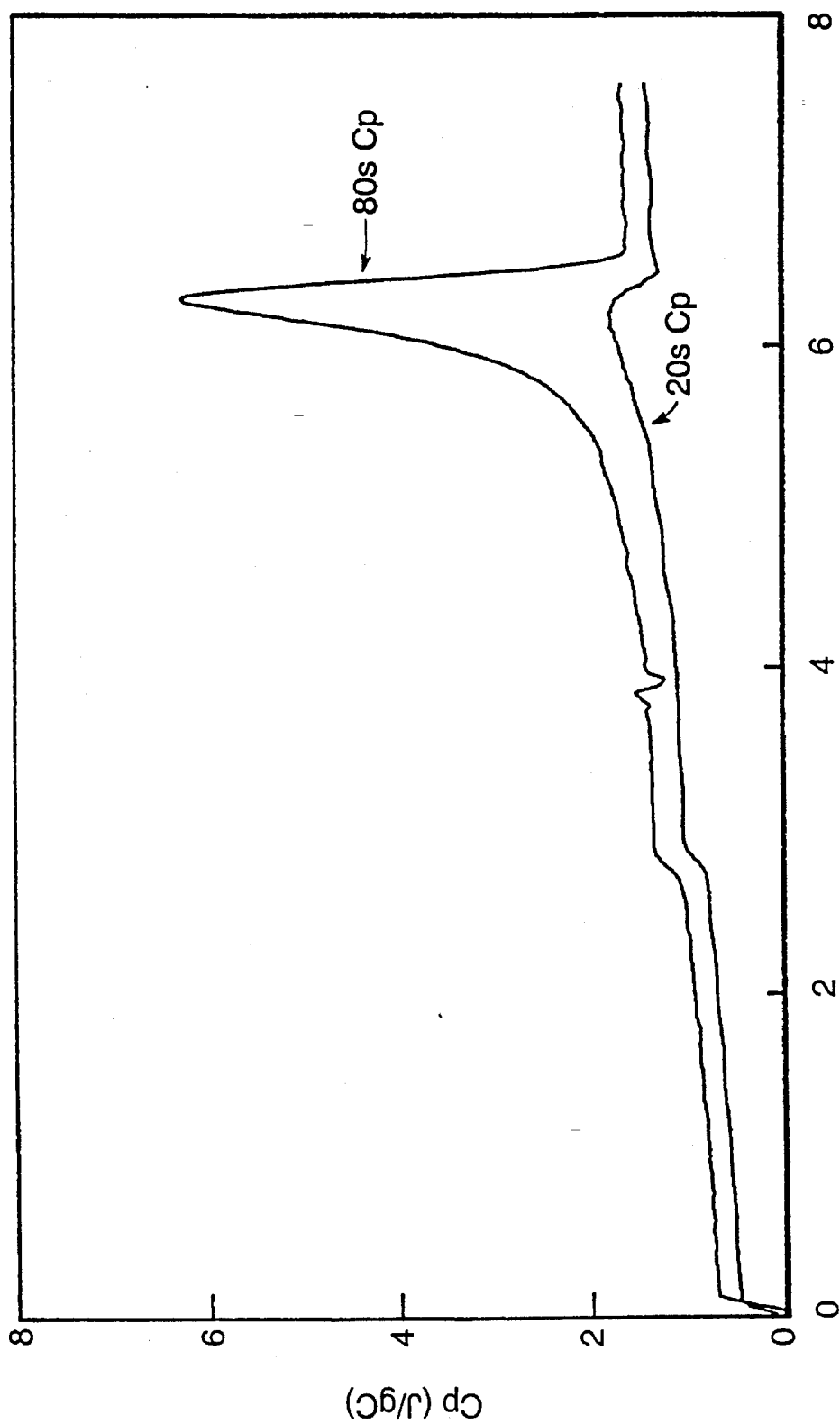
FIG. 35 is a comparison of the primary and secondary modulation heat capacities.
Figure 36:
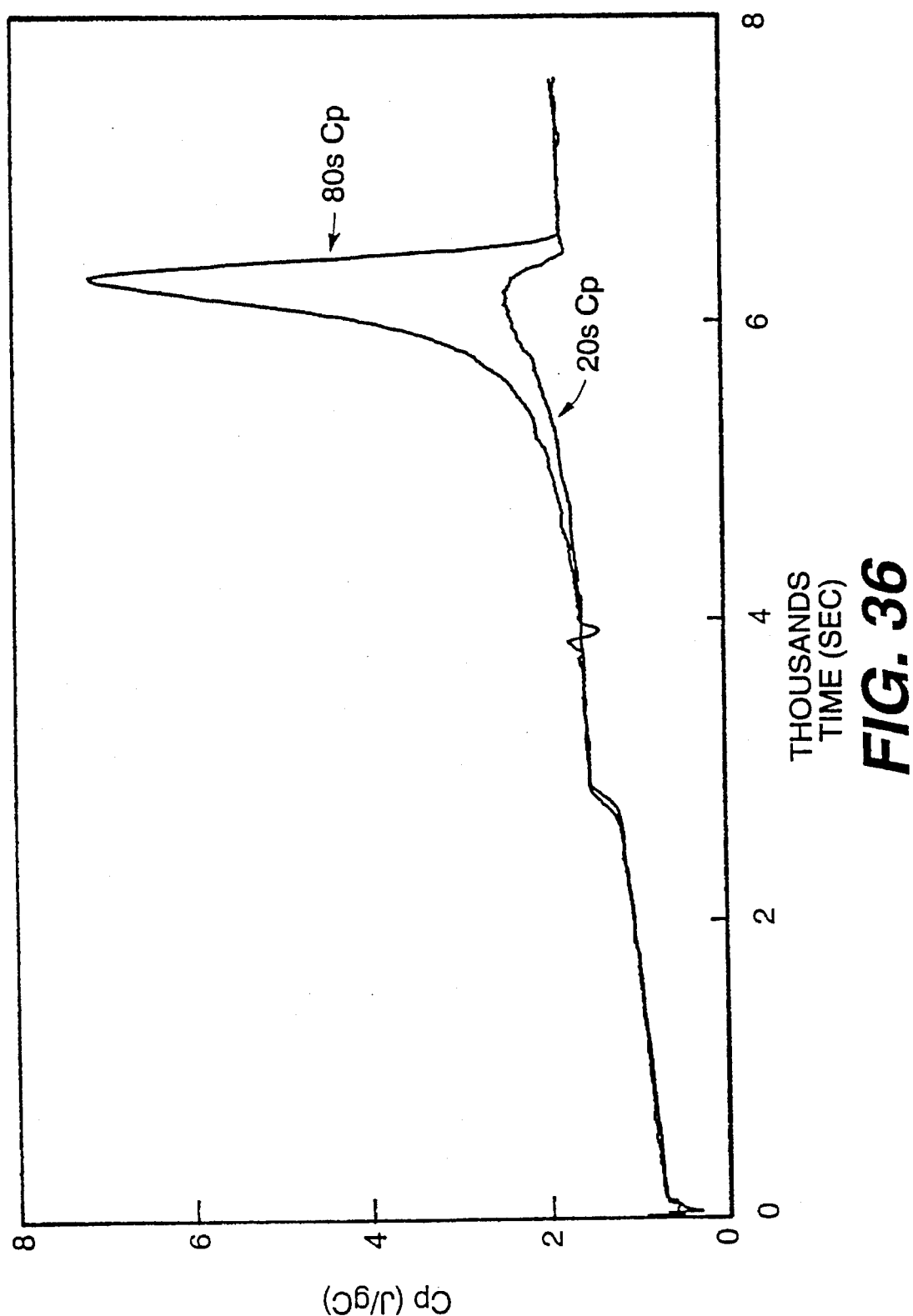
FIG. 36 is a comparison of the primary and secondary modulation heat capacities after calibration.

FIG. 35 (see Table 35) shows the results after deconvolution. Clearly there are two heat capacity data sets (one from each modulation) and the values of the apparent heat capacities are dependent upon modulation frequency. Calibration resolves this difference, as shown in FIG. 36 (see Table 36). There is a very good agreement between the two heat capacities up to the recrystallization peak and above the melt which confirms that multiplexing produces useful data. However, a large difference is observed during the melt which proves that the apparent heat capacity during such an event is still dependent upon the frequency of the modulation. It is within this region that the most useful information can be gleaned.

Digitization Noise

Figure 37:
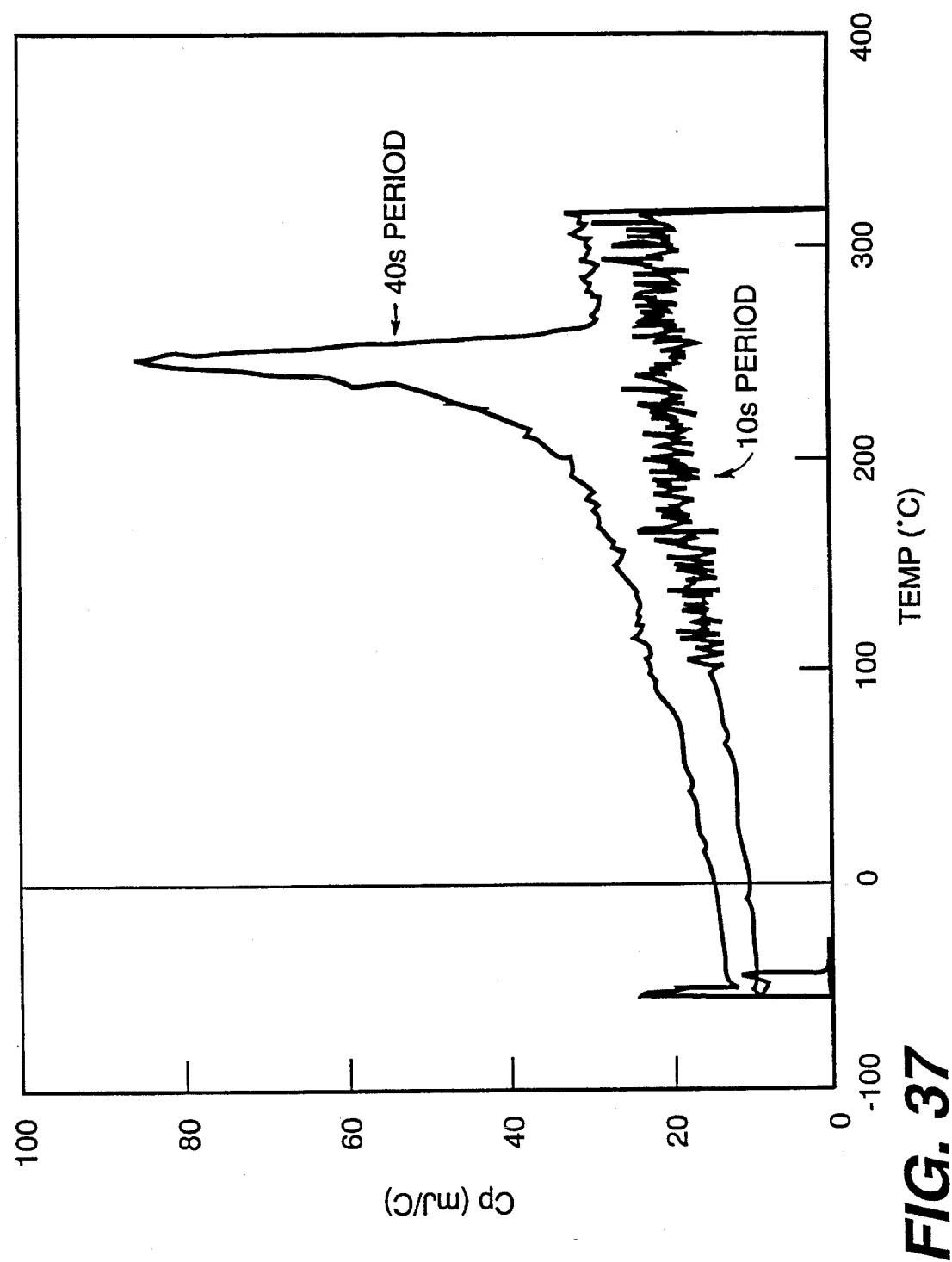
FIG. 37 shows that the noise problem increases significantly at 100° C. (if an insufficient number of significant figures is retained).

The report files generated from the raw data must include a sufficient number of significant figures to avoid generating unnecessary noise. FIG. 37 (see Table 37) shows that this problem can be particularly significant at temperatures above 100° C., simply because one additional significant figure is required to express temperatures at or above 100° C., compared to temperatures below 100° C.

Parsing Multiplexed DDSC Measurements

The simplest method for parsing multiplexed DDSC data is to remove the higher frequency by averaging the data over the appropriate period, and then parse the data in accordance with the averaged data. Each parsed data set could then be analyzed in the manner described above for standard DDSC. The higher frequency can then be restored and parsed in accordance with the time intervals given by the parsing at the lower frequency. The higher frequency data could then be analyzed to calculate $C_p$ and phase lag.

A second, more complicated, method is to parse the multiplexed signal itself. In this method, individual cycles in the higher frequency modulation will be separated, for example, into heating, cooling and reheating parsets (whereas, in the first method for parsing multiplexed DDSC data, discussed above, the data was not parsed at the higher frequency). The problem with this greater level of fragmentation of data is that sometimes only a small part of the cycle would be separated out, and this might not be enough for accurate analysis. The advantage of this more complicated second method is that it is more rigorous than the first simpler method, and potentially generates more information.

A third method is to essentially follow the second method, but ignore data sets that are too small. A fourth method also essentially follows the second method, but separates out the data sets which conform to simple behavior. In this fourth method, for example, only those data sets wherein both frequencies are heating, both frequencies are cooling and both frequencies are reheating are selected for analysis. The third and fourth methods could also be used in combination.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. For example, the parsing method could readily be extended to provide a smooth continuous curve rather than the discrete points described herein. The scope of the invention is to be defined only by the claims appended hereto, and by their equivalents.

TABLE 8

PARAMETERS USED TO OBTAIN PLOT SHOWN IN FIG. 8

| | |
|---|---|
| Sample: | Baseline |
| Size: | 0.0000 mg |
| Method: | −60 to 330 R3 P80 A2 |
| Comment: | −60 to 330° C. at 3° C./min. Period 80s. Amp 2° C. |
| File: | A:PARS-1.029 |
| Run Date: | 10-Jan-94 13:52 |
| Purge: | Helium |

TABLE 11

PARAMETERS USED TO OBTAIN PLOT SHOWN IN FIG. 11

| | |
|---|---|
| Sample: | Sapphire |
| Size: | 60.6360 mg |
| Method: | −60 to 330 R3 P80 A2 |
| Comment: | −60 to 330° C. at 3° C./min Period 80s. Amp 2° C. |
| File: | A:PARS-1.030 |
| Run Date: | 11-Jan-94 09:04 |
| Purge: | Helium |

TABLE 13

PARAMETERS USED TO OBTAIN PLOT SHOWN IN FIG. 13

| | |
|---|---|
| Sample: | PET |
| Size: | 16.3140 mg |
| Method: | −60 to 330 R3 P80 A2 |
| Comment: | −60 to 330° C. at 3° C./min. Period 80s. Amp 2° C. |

TABLE 13-continued

PARAMETERS USED TO OBTAIN PLOT SHOWN IN FIG. 13

| | |
|---|---|
| File: | A:PARS-1.031 |
| Run Date: | 11-Jan-94 12:21 |
| Purge: | Helium |

TABLE 17

PARAMETERS USED TO OBTAIN PLOT SHOWN IN FIG. 17

| | |
|---|---|
| Sample: | Baseline (UNCRMPD: 22.509) |
| Size: | 0.0000 mg |
| Method: | −60 to 330 R3 P80 A2 |
| Comment: | −60 to 330° C. at 3° C./min. Period 80s. Amp 2° C. |
| File: | A:PARS-1.029 |
| Run Date: | 10-Jan-94 13:52 |
| Purge: | Helium |

TABLE 18

PARAMETERS USED TO OBTAIN PLOT SHOWN IN FIG. 18

Heat Capacities of Sapphire Disk Heating, Cooling and Reheating

TABLE 19

PARAMETERS USED TO OBTAIN PLOT SHOWN IN FIG. 19

| | |
|---|---|
| Sample: | Sapphire (UNCRMPD: 22.509) |
| Size: | 60.6360 mg |
| Method: | −60 to 330 R3 P80 A2 |
| Comment: | −60 to 330° C. at 3° C./min. Period 80s. Amp 2° C. |
| File: | A:PARS-1.030 |
| Run Date: | 11-Jan-94 09:04 |
| Purge: | Helium |

TABLE 20

PARAMETERS USED TO OBTAIN PLOT SHOWN IN FIG. 20

| | |
|---|---|
| Sample: | PET (UNCRMPD: 22.509) |
| Size: | 16.3140 mg |
| Method: | −60 to 330 R3 P80 A2 |
| Comment: | −60 to 330° C. at 3° C./min Period 80s. Amp 2° C. |
| File: | A:PARS-1.031 |
| Run Date: | 11-Jan-94 12:21 |
| Purge: | Helium |

TABLE 24

PARAMETERS USED TO OBTAIN PLOT SHOWN IN FIG. 24

| | |
|---|---|
| Sample: | PET |
| Size: | 13.6610 mg |
| Method: | 130 to 330 R5 P30 A0.2 |
| Comment: | 130 to 330° C. at |

TABLE 24-continued

PARAMETERS USED TO OBTAIN PLOT SHOWN IN FIG. 24

| | |
|---|---|
| | 5° C./min. |
| | P = 30s A = 0.2° C. |
| File: | A:PARS-1.034 |
| Run Date: | 24-Feb-94 13.47 |
| Purge: | Helium |

TABLE 25

PARAMETERS USED TO OBTAIN PLOT SHOWN IN FIG. 25

HEAT CAPACITIES AND PHASE LAG OF
QUENCHED PET
130 to 330C
Heating only
Parsed according to Cyclic Mod Temp: (+ve or −ve)

TABLE 26

PARAMETERS USED TO OBTAIN PLOT SHOWN IN FIG. 26

HEAT CAPACITIES AND PHASE LAG OF
QUENCHED PET
130 to 330C
Heating only
Parsed according to Cyclic Heat Flow: (+ve or −ve)

TABLE 27

PARAMETERS USED TO OBTAIN PLOT SHOWN IN FIG. 27

HEAT CAPACITIES AND PHASE LAG OF QUENCHED
PET
130 to 330 C.
Heating only
Parsed according to Cyclic Deriv Mod Temp:
(+ve or −ve)

TABLE 28

PARAMETERS USED TO OBTAIN PLOT SHOWN IN FIG. 28

| | |
|---|---|
| Sample: | PET (UNCRMPD) |
| Size: | 16.7040 mg |
| Method: | 50 to 100 R5 P20 A0.10 |
| Comment: | 50 to 100 R: 5° C./min. |
| | P: 20s Amp: 0.10° C. |
| | QIO.2 QJ4 QH-1 |
| File: | A:MDSC-14.027 |
| Run Date: | 2-Feb-94 15:14 |
| Purge: | He |

TABLE 29

PARAMETERS USED TO OBTAIN PLOT SHOWN IN FIG. 29

| | |
|---|---|
| Sample: | QUENCHED PET (UNCRMPD) |
| Size: | 16.4130 mg |
| Method: | −60 to 330 R5 P10 A0.15 |
| Comment: | −60 to 330 R: 5° C./min. |
| | P: 10s Amp: 0.15° C. |
| | QIO.1 QJ4 QH-1 |
| File: | A:MDSC-14.024 |

TABLE 29-continued

PARAMETERS USED TO OBTAIN PLOT SHOWN IN FIG. 29

| | |
|---|---|
| Run Date: | 2-Feb-94 09:02 |
| Purge: | He |

TABLE 30

PARAMETERS USED TO OBTAIN PLOT SHOWN IN FIG. 30

MULTIPLEXED DATA AND 1ST DECONVOLUTION
From FTMPLX1.BAS -
Leaving secondary modulation

TABLE 31

PARAMETERS USED TO OBTAIN PLOT SHOWN IN FIG. 31

DECONVOLUTION OF SECONDARY MODULATION
From FTMPLX2.BAS -
Leaving the underlying signals

TABLE 32

Figure 32:
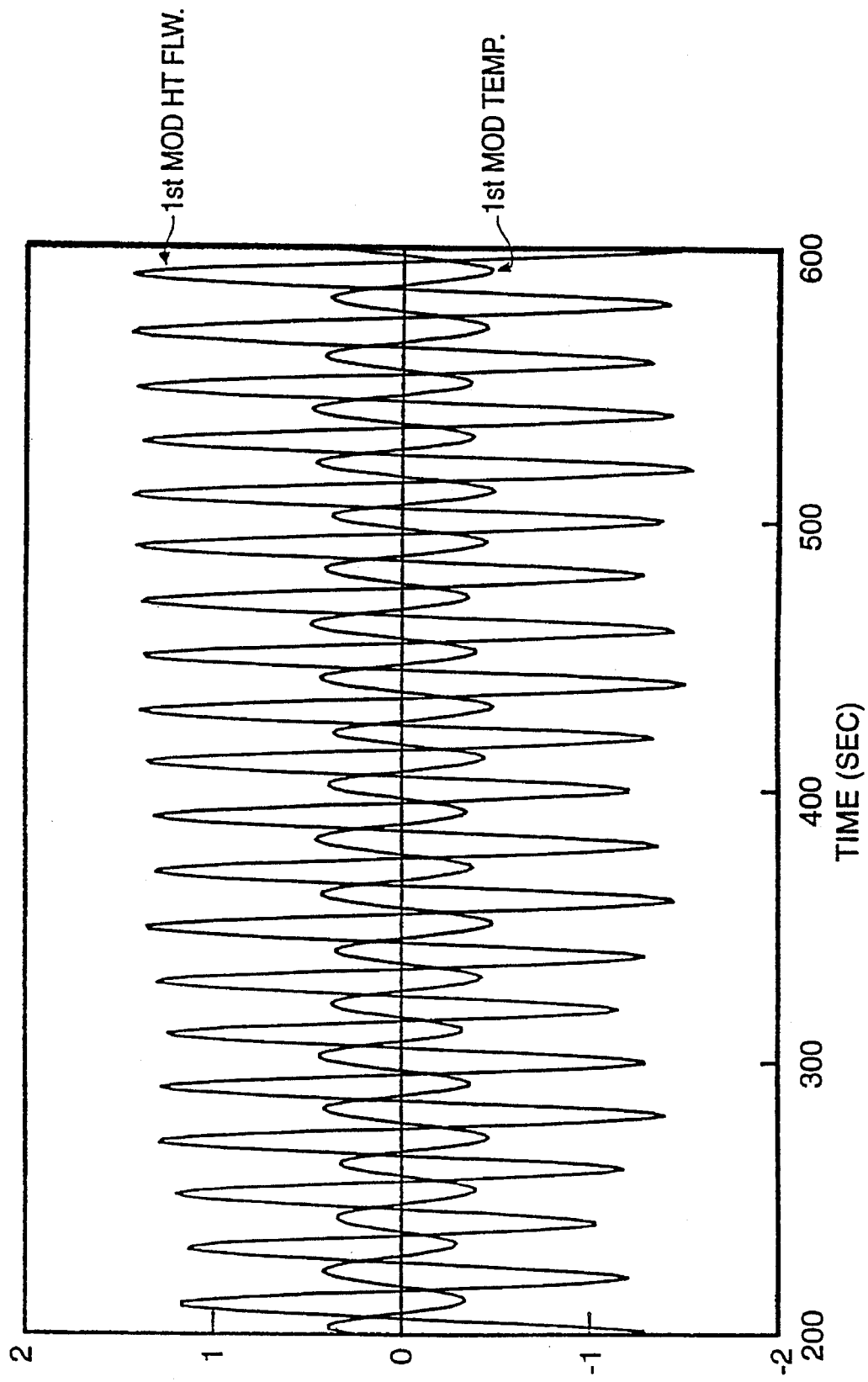
FIG. 32 is a plot of the cyclic component of the primary modulation.
Figure 33:
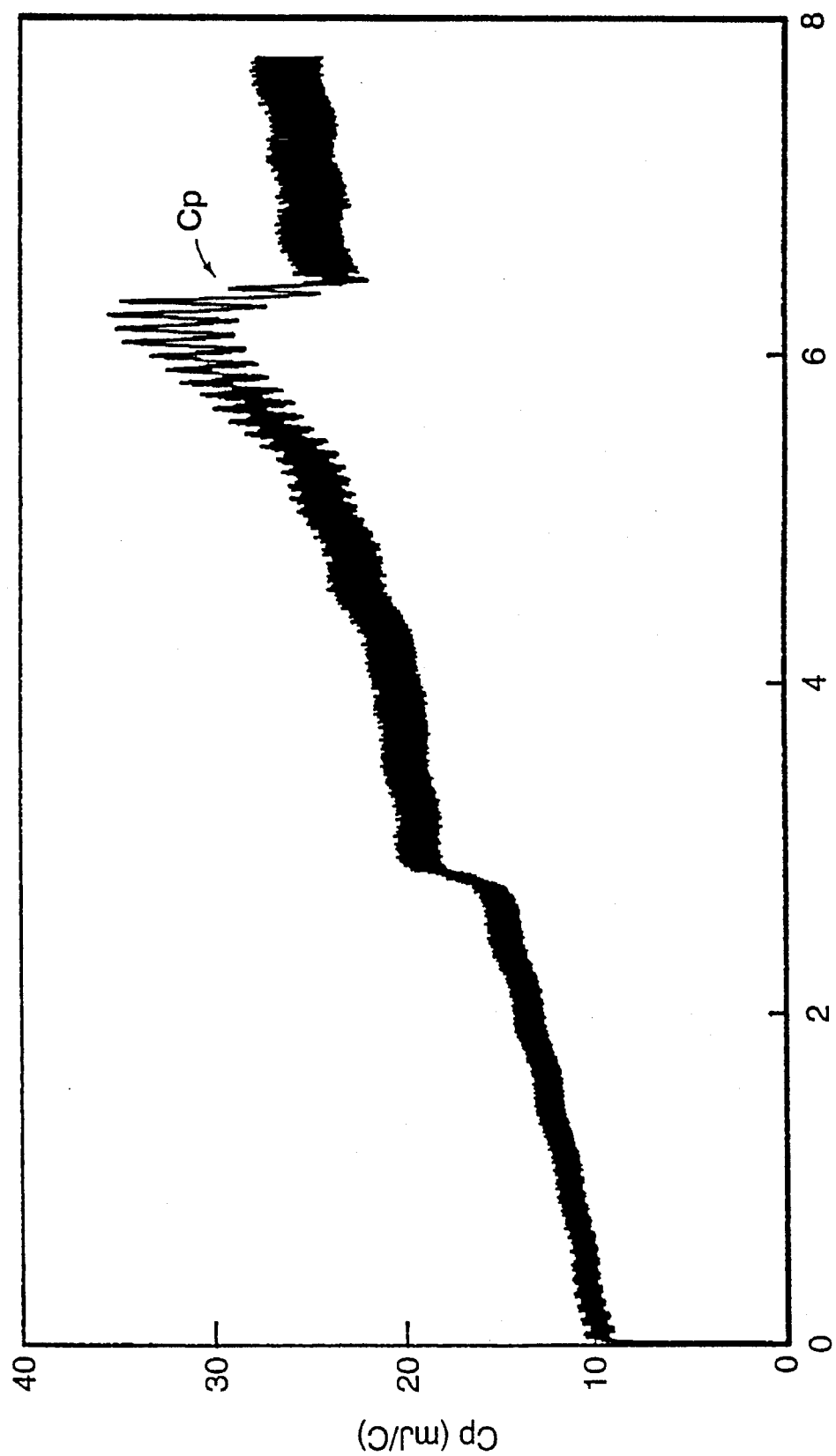
FIG. 33 is a plot of the primary modulation heat capacity.

PARAMETERS USED To OBTAIN PLOT SHOWN IN FIG. 32

CYCLIC COMPONENTS OF PRIMARY MODULATION
Multiplexed signals -
Secondary Modulation signals
Calc in FTMPLX3.BAS

TABLE 33

PARAMETERS USED TO OBTAIN PLOT SHOWN IN FIG. 33

HEAT CAPACITY OF PRIMARY MODULATION
Calculated from cyclic components of signals by
FTMPLX3.BAS

TABLE 34

PARAMETERS USED TO OBTAIN PLOT SHOWN IN FIG. 34

HEAT CAPACITY OF PRIMARY MODULATION
Fourier Transformed at secondary period
Calculated by FTMPLX4.BAS

TABLE 35

PARAMETERS USED TO OBTAIN PLOT SHOWN IN FIG. 35

APPARENT HEAT CAPACITIES OF QUENCHED PET
Multiplexed Experiment

TABLE 36

PARAMETERS USED TO OBTAIN PLOT SHOWN IN FIG. 36

CALIBRATED HEAT CAPACITIES OF QUENCHED PET

TABLE 36-continued

PARAMETERS USED TO OBTAIN PLOT SHOWN IN FIG. 36

Multiplexed Experiment

TABLE 37

PARAMETERS USED TO OBTAIN PLOT SHOWN IN FIG. 37

EXAMPLE OF NOISE PROBLEMS IN HEAT CAPACITIES OF PET
Multiplexed Experiment
Noise increases significantly at 100 C.

APPENDIX A

The programs in this appendix are written in Microsoft Qbasic. They are intended to serve as examples of programs that implement the present invention. They are not intended to limit the invention in any way. The scope of the invention is to be defined only by the claims appended hereto, and by their equivalents.

DATA PARSING PROGRAM (©, 1994, TA Instruments, Inc.)

```
' open input/output files

CLS

INPUT "Please enter name of file to be parsed (Q to
    Quit) : ", name$

IF name$ = "Q" OR name$ = "q" THEN END

OPEN name$ FOR INPUT AS #1

INPUT "Name of output files : ", out$

OPEN out$ + ".HT" FOR OUTPUT AS #2
    OPEN out$ + ".CL" FOR OUTPUT AS #3
    OPEN out$ + ".RH" FOR OUTPUT AS #4

IF name$ = "Q" OR name$ = "q" THEN END

'SOUND 250, 10: SOUND 210, 5: SOUND 170, 10: SOUND 210,
    10: SOUND 250, 10: SOUND 340, 20

DIM temp(5000)

A = 1: zero = 100 ' zero is used as a marker for the
    analysis program SMLRG10.BAS maxtemp = -200

'FOR k = 1 to 17

'LINE INPUT #1, titles$

'NEXT k
' read in data line-by-line, parse and write to output files

DO UNTIL EOF(1)
```

```
LINE INPUT #1, z$ temp(A) = VAL(MID$(z$, 14, 8)): tim = VAL(MID$(z$, 5,
9)): modQ = VAL(MID$(z$, 22, 9)): thet = VAL(MID$(z$,
32, 8)): dmt = VAL(MID$(z$, 40 10))

IF temp(A) >= maxtemp - .00001 OR temp(A) = maxtemp AND
h = 1 THEN

PRINT "heat", z$ h = 1

WRITE #2, tim, dmt, thet, temp(A), modQ
WRITE #3, tim, dmt, thet, zero, zero
WRITE #4, tim, dmt, thet, zero, zero maxtemp = temp(A)

ELSEIF temp(A) < temp(A - 1) OR temp(A) = temp (A - 1)
AND h = 0 THEN

PRINT "cool", z$
h = 0

WRITE #3, tim, dmt, thet, temp(A), modQ
WRITE #2, tim, dmt, thet, zero, zero
WRITE #4, tim, dmt, thet, zero, zero

ELSE

PRINT "reheat", z$ h = 2

WRITE #4, tim, dmt, thet, temp(A), modQ
WRITE #2, tim, dmt, thet, zero, zero
WRITE #3, tim, dmt, thet, zero, zero

END IF

A = A + 1

LOOP

' Close all files

CLOSE #2: CLOSE #3: CLOSE #4

CLS

'SOUND 420, 10: SOUND 380, 5: SOUND 330, 10: SOUND 210,
10: SOUND 230, 10: SOUND 250, 10
```

```
        PRINT "Complete!"

END

DECONVOLUTION PROGRAM (©, 1994, TA Instruments, Inc.)

' open files and query input file requirements

CLS

INPUT "Enter name of file to work out :", nam$

OPEN nam$ FOR INPUT AS #1

INPUT "Enter name of output file :", out$

OPEN out$ FOR OUTPUT AS #2

INPUT "Enter number of sections to analyze :", sect

INPUT "Enter data sampling interval :", sampint

INPUT "Enter starting point.  (Must be in space between
        sections) :", start DIM x (5000): DIM y(5000): DIM m(50): DIM c(50): DIM
        avdif(50)

count = 0                'move to required starting point

DO UNTIL count = start count = count + 1

INPUT #1, tim$, dmt$, thet$, modt$, modq$ y(count) = VAL(modq$): x (count) = -VAL(dmt$)

LOOP

FOR sectn = 1 TO sect

IF count = start THEN GOTO 10

5       inicount = count      'read in data parset until "100"
                               marker is found DO UNTIL y(count) = 100 count = count + 1

INPUT #1, tim$, dmt$, thet$, modt$, modq$
```

```
        y(count) = VAL(modq$): x (count) = -VAL(dmt$)

LOOP num = count - inicount

'******** CALCULATION ********

ERASE avdif, m, c: n = 0: b = 0: avdif(0) = 10000000

LOCATE 10, 12: PRINT "-dT/dt advanced by :"; b;
    "seconds."

GOTO 15

' least square fit loop

DO WHILE avdif(n) < avdif(n - 1) OR m(n - 1) < 0 OR
    avdif(n) > .5

15  n = n + 1: xtot = 0: xsqtot = 0: ytot = 0: xytot = 0:
    totdif = 0 j = n - 1        ******* n=no of times through shifting
                             process *** k = num - j v = inicount

DO UNTIL v - inicount = k    ' linear regression
                                   calculations xtot = xtot + x(v)

xsq = x(v) ^ 2: xsqtot = xsqtot + xsq ytot = ytot + y(v + j)

xy = x(v) * y(v + j)

xytot = xytot + xy v = v + 1

LOOP

LOCATE 10, 32: PRINT b xav# = xtot / k yav# = ytot / k
```

```
Sxx = xsqtot - ((xtot ^ 2) / k)

Sxy = xytot - (xtot * ytot / k)

m(n) = Sxy / Sxx c(n) = yav# - m(n) * xav#

PRINT "slope", m(n): PRINT "const", c(n)

w = inicount        'difference of the squares calculation

DO UNTIL w - inicount = k dif = ABS ((m(n) * x(w) + c(n)) - y(w + j))

totdif = totdif + dif w = w + 1

LOOP avdif(n) = totdif / k

PRINT "Average Sum of Differences Squared ", avdif(n)

h = h + sampint

CLS

PRINT "The Phase Difference has been resolved for section"; sectn

PRINT

PRINT "The -dT/dt signal had to be shifted forward in time by :";  b - (2 * sampint); "seconds."

PRINT "The line of best fit through the points has gradient : ", m(n - 1)

PRINT "and an offset of : ", c(n - 1)

PRINT "The average sum of the Differences is : ", avdif(n - 1)

PRINT #2, initime, sectn, m(n - 1), c(n - 1), b - (2 * sampint)

10   DO WHILE y(count) = 100   ' moves through gaps in files
                                 while "100"

count = count + 1          ' marker is present.
```

```
INPUT #1, tim$, dmt$, thet$, modt$, modq$ y(count) = VAL(modq$): x(count) = -VAL(dmt$)
LOOP initime = VAL(tim$)

NEXT sectn
```

' clear memory and close files

```
ERASE x: ERASE y

CLOSE #1: CLOSE #2
```

APPENDIX B

[PAGE 1]
'\*\*\*All of the following programs are protected by Copyright TA Instruments 1994\*\*\*
　　　　\*\*\*\*\*\*INTRO.BAS\*\*\*\*\*\*

```
5 CLS
PRINT "   WELCOME to Rob's Fabulous Guide to Deconvoluting MDSC Data..."
PRINT "                         ..and his low quality programs"
PRINT
PRINT "                              Please select the lesser of the five evils ;"
LOCATE 10, 10
PRINT " (1)          Parsing and analysis of MDSC data."
LOCATE 12, 10
PRINT " (2)          Analysis of Multiplexed MDSC data."
LOCATE 14, 10
PRINT " (3)          Parsing and analysing Multiplexed MDSC data."
LOCATE 16, 10
PRINT " (4)          General information on the analysis programs."
LOCATE 18, 10
PRINT " (5)                  Quit before the going gets tough."
10 x$ = INPUT$(1)
x = VAL (x$)
SELECT CASE x
CASE 1
Run "C:\rob\pars\parsint.bas"
CASE 2
RUN "C:\rob\MPLX\MPLXint.BAS"
CASE 3
PRINT
PRINT "I'm afraid I haven't even attempted that yet!!"
GOTO 10
CASE 4
GOTO 20
CASE 5
CLS: PRINT "You made the best choice, why make things more complicated than they already are?"
SLEEP 3
END
CASE ELSE
PRINT
PRINT            "Don't be silly .. Pick 1, 2 ,3, 4 or 5."
GOTO 10
END SELECT
20 CLS
PRINT "          Rob's Fabulous Guide to Deconvoluting MDSC Data"
PRINT
PRINT "          Part 2; the return of the Temperature Perturbation...."
LOCATE 7, 1
PRINT "              It is recommended that all data should be loaded onto the hard drive of "
PRINT "your computer before analysis and output files should also be written to the "
PRINT "the hard drive - These files can then be deleted/removed when analysis is "
PRINT "complete. Substantial time savings are obtained using this method."
PRINT " - Alternatively you can buy a top of the range computer with a maths"
PRINT " coprocessor + superconducting chips but this is more expensive."
PRINT " - Or you can improve my programs a bit (I'm only a chemist you know)"
PRINT
PRINT "All of the programs available have their limitations and should any problems"
PRINT "be encountered it is recommended that they should be run individually in turn"
PRINT "and the results after each stage studied until the problem becomes apparent."
PRINT " The files that carry the information from one stage of analysis to another"
PRINT "are not deleted until the final stage of the final program so isolating the "
PRINT "required data should not pose a problem; just remove the KILL statements."
PRINT
PRINT "              Press any key to return to main menu...."
y$ = INPUT$(1)
```

IF y$ <> "" THEN GOTO 5

[PAGE 2]
MULTIPLEXING DEVONVOLUTION SOFTWARE

\*\*\*\*\*\*\*MXPLXINT.BAS\*\*\*\*\*\*\*

```
CLS
PRINT "You choose to live dangerously, two modulations are deadlier than one..."
SLEEP 3
CLS
PRINT "                          Analysis of Multiplexed MDSC."
LOCATE 3, 10
PRINT "               This is achieved using four QBasic programs ;"
PRINT
PRINT "               All four programs use the same calculations; Fourier transforming one"
PRINT "oscillation at a time to leave the underlying data. They only differ in their"
PRINT "input/output characteristics and the number of calcuations they perform."
PRINT
PRINT " 1 / FTMPLX1 -  Removal of the primary modulation from the multiplexed signals to"
PRINT "                            leave the secondary modulation. It reads from a LOTUS file that"
PRINT "                            contains Time(s), Mod Temp(C), Mod Heat Flow (mJ) in that order."
PRINT
PRINT " 2 / FTMPLX2 -  Analysis of secondary modulation."
PRINT
PRINT " 3 / FTMPLX3 -  Subtraction of secondary modulation from the multiplexed signals"
PRINT "                            to give the cyclic component of the primary modulation. This "
PRINT "                            component is then analysed."
PRINT
PRINT " 4 / FTMPLX4 -  Fourier Transforming the results from the primary modulation at "
PRINT "                            the secondary modulation frequency to remove and measure their "
PRINT "                            dependance upon it."
PRINT
PRINT " Press Q to return to main menu or anything else to begin :"
y$ = INPUT$(1)
SELECT CASE y$
CASE "q", "Q"
Run "C:\rob\INTRO.BAS"
CASE ELSE
RUN "C:\rob\mplx\FTMPLX1.BAS"
END SELECT
END
```

\*\*\*\*\*\*FTMPLX1.BAS\*\*\*\*\*\*

\*\*\*\*\*\*Reads from LOTUS files\*\*\*\*\*\*
\*\*\*\*\*\*\*and removes primary modulation\*\*\*\*\*\*
\*\*\*\*\*\*\*\*\*analyses FULL mod cycle\*\*\*\*\*\*

```
CLS
PRINT " FTMPLX1 - Removing primary modulation from multiplexed signals."
PRINT
INPUT "Enter File name for Deconvolution : ", fil$
OPEN "c:\rob\MPLX\" + fil$ FOR INPUT AS #1
INPUT "Enter Primary Modulation Period (s) : ", period
INPUT "Enter Secondary Modulation Period (s) :", period2
INPUT "Enter Data Sampling Interval (s/point) : ", sampint
INPUT "Enter Output Points Skip for Lotus Files :", outint
INPUT "Enter File Name of Output Files for Lotus :", outfil$
OPEN "c:\rob\MPLX\FTMPLX1.dec" FOR OUTPUT AS #2
WRITE #2, fil$, period, period2
WRITE #2, sampint, outint, outfil$
LOCATE 12, 20: PRINT "Time (s) ="
``` points = (period / sampint) + 1
DIM t (500): DIM Qm(500): DIM arrQ(500): DIM Tm(500): DIM arrT(500)
arrQ = 0: arrT = O
j = 1: count = 1: n = 0: PI = 3.141592653589#

[PAGE 3]
```
c = j + 1      '*** c is 1 cycle behind j**
'FOR a = 1 TO 17
'LINE INPUT #1, title$
'NEXT a
DO UNTIL EOF(1)        *main loop*
LINE INPUT #1, dat$
t(j) = VAL (MID$ (dat$, 1, 12)): Tm(j) = VAL (MID$ (dat$, 13, 9)): Qm(j) = VAL (MID$ (dat$, 22, 9))
LOCATE 12, 30: PRINT t(j)
'          *******Working out Total Ht Flw / Temp*******
IF count >= (points - 1) / 2 THEN
Qtot = Qtot + Qm(b): Ttot = Ttot + Tm(b)
Qtot = Qtot - arrQ(j): Ttot = Ttot - arrT(j)
arrQ(j) = Qm/(b): arrT(j) = Tm(b)
Qav2 = Qtot / points: Tav2 = Ttot / points
END IF
IF count >= points THEN
time = t(c)  'Time delay of one cycle
WRITE #2, time, Tav2, Qav2
END IF
j = (j MOD points) + 1
b = (b MOD points) + 1
c = (c MOD points) + 1
count = count + 1
LOOP
CLOSE #1: CLOSE #2
ERASE t, Qm, arrQ, Tm, arrT
CLS
RUN "C:\rob\mplx\FTMPLX2.bas"
END '  *****FTMPLX2.BAS*****
                '*****Reads from FTMPLX1 output*****
                '*******Giving secondary modulation Cp*******

CLS
OPEN "c:\rob\MPLX\FTMPLX1.dec" FOR INPUT AS #1
INPUT #1, fil$, period, period2
INPUT #1, sampint, outint, outfil$
PRINT " FTMPLX2 - Deconvoluting Secondary Modulation"
PRINT
OPEN "C:\rob\mplx\" + outfil$ + ".spd" FOR OUTPUT AS #2
PRINT fil$, "Period1 :"; period, "Period2 :"; period2, "Sampint :"; sampint
LOCATE 12, 20: PRINT "Time (s) = "
points = (period 2 / sampint) + 1
DIM arr (500): DIM t (750): DIM Qm (500): DIM arrC (500): DIM arrS (500): DIM arrQ (500): DIM Tarr (500): DIM Tm (500):
DIM TarrC (500):  DIM arrS (500): DIM arrT (500): DIM arrp (500): DIM arrQ2/500): DIM arrT2 (500)
arr = 0: arrC = 0: arrS = 0: arrQ = 0: Tarr = 0: TarrC = 0: TarrS = 0: arrT = 0
j = 1: n = 0: total = 0: Ttotal = 0: count = 1: counter 1: PI = 3.14159265389#: Kcp = 1
b = j + ((points - 1) / 2) + 1
c = j
d = c + 1
e = ((points) + ((points - 1) / 2))
DO UNTIL EOF (1)
'          *******Generating second reference sine angle*******
IF n = 0 THEN theta2 = 0: GOTO 10
theta2 = (n / (points - 1)) * 2 * PI
IF (points - 1) / n = 1 THEN n = 0
10 n = n + 1
                '*******Working out Average Ht Flw / Temp*******
INPUT #1, t(c), Tm(j), Qm(j)
LOCATE 12, 30: PRINT t(c)
total = total + Qm(j): Ttotal = Ttotal + Tm(j)
```

```
total = total - arr(j): Ttotal = Ttotal - Tarr(j)
arr(j) = Qm(j): Tarr(j) = Tm(j)
Qavl = total / points: Tavl = Ttotal / points
```

[PAGE 4]
```
IF count ) = (points - 1) / 2 THEN
Qtot = Qtot + Qm(b): Ttot = Ttot + Tm(b)
Qtot = Qtot - arrQ(j): Ttot = Ttot - arrT(j)
arrQ(j) = Qm(b): arrT(j) = Tm(b)
Qav2 = Qtot / points: Tav2 = Ttot / points
'                    *******Working out Ht Flw / Temp Amplitudes*******
Qcos = (Qm(b) - Qav1) * COS(theta2): Tcos = (Tm(b) - Tav1) * COS(theta2)
Qsin = (QM(b) - Qav1) * SIN(theta2): Tsin = Tm(b) - Tav1) * SIN(theta2)
QCtot = QCtot + Qcos: QStot = Qstot + Qsin: TCtot = TCtot + Tcos: TStot = TStot + Tsin
QCtot = QCtot - arrC(j): Qstot = QStot - arrS(j): TCtot = Tctot - TarrC(j): TStot = TStot - TarrS(j)
arrC(j) = Qcos: arrS(j) = Qsin: TarrC(j) = Tcos: TarrS(j) = Tsin
Qcossum = QCtot: Qsinsum = QStot: Tcossum = TCtot: Tsinsum = TStot
Qamp = 2 * SQR ((Qcossum ^ 2) + (Qsinsum ^ 2)) / points: Tamp = 2 * SQR ((Tcossum ^ 2)) / points '                    *****Working out Heat Capacity*****
omega = (2 * PI) / period2
Cp = Kcp * (Qamp / Tamp) * (1 / omega)

'                    *******Averaging Cp data for use in Lotus files*******
cptot = cptot + Cp
cptot = cptot - arrp(j)
arrp(j) = Cp
cpav = cptot / points '*cpav now delayed 1.5 cycles*

'                    *Further averaging Qav2 and Tav2 for output to lotus files*
Q2tot = Q2tot + Qav2: T2tot = T2tot + Tav2
Q2tot = Q2tot - arrQ2(j): T2tot = T2tot - arrT2(j)
arrQ2(j) = Qav2: arrT2(j) = Tav2
Q2av = Q2tot / points: T2av = T2tot / points'*Q2av now delayed 1.5 cycles*
END IF

*******Writing secondary Cp data to Lotus files*******
IF count >= e THEN
cptim = t(d)
s = counter / outint
IF s = 1 THEN
WRITE #2, cptim, T2av, Q2av = cpav "all have 1.5 cycle delay*
counter = counter + 1
END IF
A - counter = 0
A END IF
counter = counter + 1
j = (j MOD points) + 1
b = (b MOD points) + 1
c = (c MOD e) + 1
d = (d MOD e) + 1
count = count + 1
LOOP
CLOSE #1: CLOSE #2
ERASE arr, t, Qm, arrC, arrS, arrQ, Tarr, Tm, TarrC, TarrS, arrT, arrp, arrQ2, arrT2
CLS
RUN "c:\rob\mplx\FTMPLX3. bas"
END '*****FTMPLX3.BAS*****
                    '*****Reads from LOTUS file and FTMLPX1 output*****
                    '*******leaving primary modulation Heat Capacity*******
CLS
OPEN "C:\rob\MPLX\FTMPLX1.dec" FOR INPUT AS #2
INPUT #2, fil$, period, period2
INPUT #2, sampint, outint, outfil$
OPEN "C:\rob\MPLX\" + fil$ FOR INPUT AS #1
```

```
OPEN "c:\rob\MPLX\FTMPLX3.dec" FOR OUTPUT AS #3
WRITE #3, fil$, period, period2
WRITE #3, sampint, outint, outfil$
PRINT " FTMPLX3 - Deconvoluting Primary Modulation."
```

[PAGE 5]
PRINT
PRINT fil$, "Period1 :"; period, "Period2 :"; period2, "Sampint :"; sampint
'              *****Input titles from report file*****
'FOR a = 1 TO 17
'LINE INPUT #1, title$
'NEXT a
'              *****preparing for primary deconvolution*****
LOCATE 12, 20: PRINT "Time (s) = "
points = (period / sampint) + 1
DIM arr(500): DIM t (500): DIM Qm (500): DIM arrC (500): DIM arrS (500): DIM Tarr (500): DIM Tm (500): DIM TarrC (500): DIM TarrS (500)
arr = 0: arrC = 0: arrS = 0: Tarr = 0: TarrC = 0: TarrS = 0
j = 1: total = 0: total = 0: count = 1: m = 0; PI = 3.141592653589#: Kcp = 1
b = j + ((points - 1) / 2) + 1
c = j + 1
'              *****Inputting and subtracting data*****
DO UNTIL EDF (1) or EDF (2)
LINE INPUT #1, dat$
tim1 = VAL (MID$ (dat$, 1, 12)): T1 = VAL (MID$ (dat$, 13, 9)): Q1 = VAL (MID$ (dat$, 22, 9))
INPUT #2, tim2, T2, Q2
IF tim1 < > tim2 THEN PRINT "not O.K. so far!!" 'Checks alignment of data between input files*
t(j) = tim1: Tm(j) = T1 - T2: Qm(j) = Q1 - Q2

'              *****Generating Primary Ref Sine Angle*****
IF m = 0 THEN theta = 0: GOTO 5
theta = (m / (points - 1) * 2 * PI
IF (points - 1) / m = 1 THEN m = 0
5 m = m +1

'              '*****Working out Average Ht Flw / Temp*****
'LOCATE 12, 30: PRINT t(j)
total = total + Qm(j): Ttotal = Ttotal + Tm(j)
total = total - arr(j): Ttotal = Ttotal - Tarr(j)
arr(j) = Qm(j): Tarr(j) = Tm(j)
Qav1 = total / points: Tav1 = Ttotal / points '              *****Working out Ht Flw / Temp Amplitudes*****
IF count >= (points - 1) / 2 THEN
Qcos = (Qm(b) - Qav1)* COS(theta: Tcos = (Tm(b) - Tav1) * COS(theta)
Qsin = (Qm(b) - Qav1) * SIN(theta : Tsin = (Tm(b) - Tav1) * SIN(theta)
QCtot = QCtot + Qcos: QStot = QStot + Qsin: TCtot = Tcos: Tstot = TStot + Tsin
QCtot = QCtot - arrC(j): QStot = QStot - arrS(j): TCtot = TCtot - TarrC(j): Tstot = TStot -TarrS(j)
arrC(j) = Qcos: arrS(j) = Qsin: TarrC(j) = Tcos: TarrS(j) = Tsin
Qcossum = QCtot: Qsinsum = QStot: Tcossum = Tctot: Tsinsum = TStot
Qamp = 2 * SQR((Qcossum ^ 2) + (Qsinsum ^ 2)) / points: Tamp = 2 * SQR ((Tcossum ^ 2)) / points '              *****Working out Heat Capacity*****
omega = (2 * PI) / period
Cp = Kcp * (Qamp / Tamp) * (1 / omega)

'              *****Adding Artificial Delay*****
END IF
IF count >= points THEN
time = t(c)
WRITE #3, time, Cp
END IF
j = (j MOD points) + 1
b = (b MOD points) + 1
c = (c MOD points) + 1
count = count + 1
LOOP
CLOSE #1: CLOSE #2: CLOSE #3

```
ERASE arr, t, Qm, arrC, arrS, Tarr, Tm, TarrC, TarrS,
CLS
RUN "C:\rob\mplx\FTMPLX4.bas"
END
```

[PAGE 6]

'*****Reads FTMPLX3 output*****
'***** and Fourier Transforms Cp signal*****
'***** at Secondary modulation frequency*****
CLS
OPEN "c:\rob\MPLX\FTMPLX3.dec" FOR INPUT AS #1
INPUT #1, fil$, period, period2
INPUT #1, sampint, outint, outfil$
PRINT "FTMPLX4 - Fourier Transforming Primary Heat Capacity at Secondary Frequency."
PRINT
OPEN "C:\rob\mplx\" + outfil$ + ".ppd" FOR OUTPUT AS #3
PRINT fil$, "Period1 :"; period, "Period2" :"; period2, "Sampint :"; sampint
LOCATE 12, 20: PRINT "Time (s) ="
points = (period2 / sampint) + 1
DIM arr (500): DIM t(500): DIM Cp(500): DIM arrCp(500): DIM arrS(500): DIM arrC(500)
arrCp = 0: arrS = 0: arrC = 0
j = 1: total = 0: count = 1: counter = 1
b = j + ((points - 1) / 2) +1
c = j + 1
DO UNTIL EDF (1)
'*****Working out Average Cp*****
INPUT #1, t(j), Cp(j)
LOCATE 12, 30: PRINT t(j)
total = total + Cp(j)
total = total - arr(j)
arr(j) = Cp(j)
Cav1 = total / points
'       *****Working out Total Cp*****
IF count >= (points - 1) / 2 THEN
Ctot = Ctot + Cp(b)
Ctot = Ctot - arrCp(j)
arrCp(j) = Cp(b)
Cav2 = Ctot / points
'       *****Working out Cp Amplitude*****
Ccos = (Cp(b) - Cav1) * COS(theta)
Csin = (Cp(b) - Cav1) * SIN(theta)
CCtot = CCtot + Ccoa: CStot = CStot + Csin
CCtot = CCtot - arrC(j): CStot = CStot - arrS(j)
arrC(j) = Ccos: arrS(j) - Csin
Ccossum = CCtot: Csinsum = CStot
Camp = 2 * SQR ((Ccossum ^ 2) + (Csinsum ^ 2)) / points '       *****Adding Artificial Delay*****

END IF
IF count >= points THEN
DecCp = Cav2
time = t(c)
s = counter / outint
IF s = 1 THEN
WRITE #3, time, DecCp, Camp
counter = 0
END IF
counter = counter + 1
END IF
j = (j MOD points) + 1
b = (b MOD points) +1
c = (t MOD points) + 1
count = count + 1
LOOP
CLOSE #1: CLOSE #2: CLOSE #3

'       *****Clearing memory and "go-between" files*****

```
ERASE arr, t, Cp, arrC, arrS, arrCp
KILL "C:\rob\mplx\FTMPLX1.dec"
KILL "C:\rob\mplx\FTMPLX2.dec"
KILL "C:\rob\mplx\FTMPLX3.dec"
CLS : PRINT    " Multiplexed deconvolution is now Complete!!"
PRINT
PRINT "Primary modulation Deconvolution is saved as   : c:\rob\mplx\"; outfil$; ".ppd"
PRINT "Secondary modulation Deconvolutin is saved as : c:\rob\mplx\"; outfil$; ".spd"
SLEEP 10
```

[PAGE 7 -blank]

[PAGE 8]

PARSING SOFTWARE

*****PARSINT.BAS*****

```
CLS
PRINT "You made a good choice.  Prepare for the next part of your adventure...."
SLEEP 3

5 CLS
PRINT "                        Parsing and analysis of MDSC data."
LOCATE 3, 10
PRINT " Parsing is achieved by seven Qbasic program in this directory (C:\rob\pars\)"
PRINT
PRINT "1/ TEMPAR1.BAS -        This program reads data straight from 2 report files. The"
PRINT "                        required data is Time(s), Mod Temp(C), Av Temp(C) and Deriv"
PRINT "                        Mod Temp (C/s) in file #1; Time(s), Deriv Av Temp (C/s), Mod"
PRINT "                        Heat Flow(mW) and Av Heat Flow(mW) in file #2.  It removes "
PRINT "                        the 1.5 cycle data delay in the average signals and then"
PRINT "                        subtracts them from the Modulated signals to leave the "
PRINT "                        Cyclic component."
PRINT
PRINT " 2/ TEMPAR2.BAS -       Reads the output from TEMPAR1.BAS and parses the data into"
PRINT "                        seperate component files depending upon whether the cell is"
PRINT "                        Heating, Cooling or Reheating."
PRINT
PRINT "3/CMTPAR2.BAS -         Reads output from TEMPAR1 and writes the data to two"
PRINT "                        seperate files depending on whether the cyclic component"
PRINT "                        of the Mod Temperature is positive or negative."
PRINT
PRINT "    I: More information.  Q: Main menu.  Other: Start Parsing process...", y$
y$ = INPUT$ (1)
SELECT CASE y$
CASE "q", "@"
RUN "C:\rob\INTRO.BAS"
CASE "I", "i"
GOTO 20
CASE ELSE
RUN "C:\rob\pars\TEMPAR1.BAS"
END SELECT
END 20 CLS
PRINT "                        Parsing and analysis of MDSC data."
PRINT : PRINT
PRINT "                        ...QBasic Parsing programs continued :"
PRINT
PRINT " 4/ CDTPAR3.BAS -       Parses as CMTPAR3 but depending upon Cyclic Deriv Mod Temp."
PRINT
PRINT "5/ CHFPAR2.BAS -        Also as CMTPAR3 but parses according to Cyclic Heat Flow."
PRINT
PRINT "6/ TEMPAR3.BAS -        Analyses the three component files written from TEMPAR3.BAS"
PRINT "                        one by one. It takes each parset of data individually,        "
PRINT "                        compares da/dt against -dT/dt to give a line of best fit,"
PRINT "                        shifts one column of data forward in time a step and then"
PRINT "                        compares the fit with the previous one. This continues        "
PRINT "                        until the phase lag is resolved and the Heat Capacity is "
PRINT "                        then taken as the gradient of the line."
PRINT
PRINT " 7 / CYCPAR3.BAS -      Analyses the +ve and -ve cyclic component files written"
PRINT                        "from CMTPAR2, CDTPAR2 or CHFPAR2 using the above method."
PRINT : PRINT
PRINT "    I:  More information.  Q: Main menu.  Other:  Start Parsing process...", x$
```

```
x$ = INPUT$(1)
SELECT CASE x$
CASE "q", "Q"
RUN "C:\rob\INTRO.BAS"
CASE "I", "i"
END
```

[PAGE 9]
GO TO 30
CASE ELSE
RUN "C:\rob\pars\TEMPAR1.BAS"
END SELECT

```
30 CLS
   PRINT "                Parsing and analysis of MDSC data."
   LOCATE 4, 1
   PRINT "The best parsing results are achieved within certain experimental limitations :"
   PRINT
   PRINT "    Longer modulation periods are preferred to ensure that the cell can reach "
   PRINT "the required modulation amplitude. The amplitude also has to be large enough to"
   PRINT "allow the sample to cool by a substantial amount. The heating rate, period and"
   PRINT "amplitude should be adjusted until a temperature profile with approximately"
   PRINT "equal amounts of heating, cooling and reheating is achieved. The size of these"
   PRINT "components should also be as large as possible without exceeding the cells"
   PRINT "operating capabilities."
   PRINT
   PRINT " Another careful consideration is the Data Sampling rate. The ideal setting "
   PRINT "is a compromise between getting as many points per modulation as possible and"
   PRINT "reasonable file sizes to keep the analysis time to an acceptable level."
   PRINT
   PRINT " The optimal parameters are only achieved by experiment but as a guide-line we"
   PRINT "found the following to be of most use :"
   PRINT "Heating Rate: 3C/min. Period 80s. Amplitude: 2C. Data Sampling: 0.6s/point."
   PRINT
   PRINT "    I: More Information. Q: Main menu. Other: Start Parsing process...", z$
   z$: = INPUT$(1)
   SELECT CASE z$
   CASE "q", "Q"
   RUN "C:\rob\INTRO.BAS"
   CASE "I", "i"
   GOTO 5
   CASE ELSE
   RUN "C:\rob\pars\TEMPAR1.BAS"
   END SELECT

*******TEMPAR1.BAS*******
5 CLS
   PRINT "   TEMPAR1      Removing 1.5 cycle data delay in Report files"
   PRINT "                and subtracting underlying data from raw data."
   PRINT
   PRINT " Yet more decisions .... Select a method of parsing : "
   PRINT
   PRINT "1/ Modulated Temperature (HT, CL, RH).   2/ Cyclic Temperature (+ve, -ve)."
   PRINT
   PRINT "3/ Cyclic Heat Flow (+ve, -ve).   4/ Cyclic Deriv of Temperature (+ve, -ve)."
   M$ = INPUT$ (1)
   SELECT CASE M$
   CASE "1", "2", "3", "4"
   CASE ELSE
   CLS
   PRINT "           Please try a little bit harder - choose 1, 2, 3 or 4."
   SLEEP 3
   GOTO 5
   END SELECT
   PRINT
   INPUT "Please enter name of report file #1 (t, Tm, Tav, dmT) :", fil1$
   OPEN "c:\rob\pars\" + fil1$ FOR INPUT AS #1
   INPUT "Please enter name of report file #2 (t, dTav, Qm, Qav) :", fil2$
   OPEN "c:\rob\pars\" + fil2$ FOR INPUT AS #2
   INPUT "Enter modulation period :", period
```

```
INPUT " Enter data sampling interval :", sampint
INPUT " Enter name of output files :", out$
```

[PAGE 10]
```
OPEN "c:\rob\pars\tempar1.dat" FOR OUTPUT AS #3
WRITE #3, fil$, out$, sampint
FOR a = 1 TO 17
LINE INPUT #1, title$
LINE INPUT #2, title$
NEXT a
DIM t (500): DM Tm (500): DIM dmT(500): DIM Qm (500)
j = 1: k = 2: points = ((period * 1.5) / sampint) + 1: count = 1
LOCATE 18, 20: PRINT " Time (s) = "
'                *******Removing data delay*******
DO UNTIL EOF(1)
LINE INPUT #1, dat$
t1 = VAL (MID$ (dat$, 1, 12)): Tm(j) = VAL (MID$ (dat$, 13, 14)): Tav = VAL (MID$ (dat$, 28, 14)): dmT(j) = VAL (MID$ (dat$, 43, 14))
LINE INPUT #2, dat2$
t2 = VAL (MID$ (dat$, 1, 12)): dTav = VAL (MID$ (dat2$, 13, 14)): Qm(j) = VAL (MID$ (dat2$, 28)): Qav = VAL (MID$ (dat2$, 43, 14))
IF t1 <> t2 THEN PRINT " Files do not match in time!!!!!": END
t(j) = t1
LOCATE 18, 30: PRINT t(j)
If count >= points THEN
cymT = Tm(k) - Tav
cycQ = Qm(k) - Qav  'removing underlying heat flow to leave cyclic component
cydT = dmT(k) - dTav
WRITE #3, t(k), Tm(k), cymT, cydT, cycQ
END IF
count = count + 1
j = (j MOD points) + 1
k = (k MOD points) + 1
LOOP
CLOSE #1: CLOSE #2: CLOSE #3
ERASE t, Tm, Qm, dmT
CLS
SELECT CASE M$
CASE "1"
RUN "c:\rob\pars\TEMPAR2.BAS"
CASE "2"
RUN "C:\rob\pars\CMTPAR2.BAS"
CASE "3"
RUN "C:\rob\pars\CHFPAR2.BAS
CASE "4"
RUN "C:\rob\pars\CDTPAR2.BAS"
END SELECT
END
                *******TEMPAR2.BAS*******
'               *******Works on output from TEMPAR1.BAS*******
CLS
PRINT "             TEMPAR2 - Parsing data into three seperate files.."
OPEN "C:\rob\pars\TEMPAR1.dat" FOR INPUT AS #1
OPEN "C:\rob\pars\TEMPAR2.dat" FOR INPUT AS #2
OPEN "C:\rob\pars\TEMPAR3.dat" FOR INPUT AS #3
OPEN "C:\rob\pars\TEMPAR4.dat" FOR INPUT AS #4
IF name$ = "Q" OR name$ = "q" THEN END
'SOUND 250, 10: SOUND 210, 5: SOUND 170, 10: SOUND 210, 10: SOUND 250, 10: SOUND 340, 20
DIM Tm(2)
A = 2: mark = 100: B = 1
maxtemp = -200
INPUT #1, fil$, out$, sampint
PRINT
PRINT fil$, "sampint :"; sampint
WRITE #2, fil$, out$, sampint
WRITE #3, fil$, out$, sampint
```

```
WRITE #4, fil$, out$, sampint
LOCATE 12, 20: PRINT "Time (s) ="
DO UNTIL EDF (1)
```

```
[PAGE 11]
LOCATE 12, 30
INPUT #1, t, Tm(A), cymT, cydT, cycQ
PRINT t
IF Tm(A) >= maxtemp - .00001 OR Tm(A) = maxtemp AND h = 1 THEN
PRINT "heat", z$
h = 1
WRITE #2, t, cydT, Tm(A), cycQ
WRITE #3, t, cydT, mark, mark
WRITE #4, t, cydT, mark, mark
maxtemp = Tm(A)

ELSEIF Tm(A) < Tm(B) OR Tm(A) = Tm(B) AND h = 0 THEN
PRINT "cool", z$
h = 0
WRITE #3, t, cydT, Tm(A), cycQ
WRITE #2, t, cydT, mark, mark
WRITE #4, t, cydT, mark, mark
ELSE
PRINT "reheat", z$
h = 2
WRITE #4, t, cydT, Tm(A), cycQ
WRITE #2, t, cydT, mark, mark
WRITE #3, t, cydT, mark, mark
END IF
A = (A MOD 2) + 1
B = (B MOD 2) + 1
LOOP
CLOSE #1: CLOSE #2: CLOSE #3: CLOSE #4
ERASE Tm
CLS
'SOUND 420, 10: SOUND 380, 5: SOUND 330, 10: SOUND 210, 10: SOUND 230, 10: SOUND 250, 10
RUN "C:\rob\pars\TEMPAR3. BAS"
END

*******TEMPAR3.BAS*******

' *******A Linear Regression Program*******
'*******Works on output fron TEMPAR2.BAS*******
ON ERROR GOTO 100
a = 1
10 CLS
PRINT "              TEMPAR3 - Working out Heat Capacities of parsets of data"
PRINT                           using linear regression and a least square fit."
PRINT
SELECT CASE a
CASE 1
OPEN "C:\rob\pars\TEMPAR2.HT" FOR INPUT AS #1
INPUT #1, fil$, out$, sampint
OPEN "C:\rob\pars\" out$ + ".HT" FOR OUTPUT as #2
PRINT "Deconvoluting Cooling Data from : "; fil$, "sampint :"; sampint
CASE 2
OPEN "C:\rob\pars\TEMPAR2.CL" FOR INPUT AS #1
INPUT #1, fil$, out$, sampint
OPEN: "C:\rob\pars\" + out$ + ".CL" FOR OUTPUT AS #2
PRINT "Deconvoluting Cooling Data from : "; fil$' "sampint :"; sampint
CASE 3
OPEN "C:\rob\pars\TEMPAR2.RH" FOR INPUT AS #1
INPUT #1, fil$, out$, sampint
```

[PAGE 12]
OPEN "C:\rob\pars\" + out$ + ".RH" FOR OUTOUT AS #2
PRINT "Deconvoluting Reheating Data from :"; fil$, "sampint :"; sampint
END SELECT DIM x (500): DIM y (500): DIM m(50): DIM c(50): DIM avdif(50)
sectn = 0: y(0) = 0

DO UNTIL y = 100         '*Finding first data gap in file*
INPUT #1, t, cydT, Tm, cycQ '(to ensure first parset analysed is a complete one)
y - cycQ: x = -cydT
LOOP
GOTO 60

20 DO UNTIL EDF(1) '*****Main loop for each parset*****
30 inicount = count
DO UNTIL y(count) = 100          '*Loading in parset data*
count = count + 1
INPUT #1, t, cydT, Tm, cycQ
IF EDF(1) THEN GOTO 20
y(count) = cycQ: x(count) = -cydT
LOOP num = count - inicount
'******Calculation******
ERASE avdif, m, c: n = 0: b = 0: avdif(0) = 10000000
LOCATE 10, 12: PRINT "-dT/dt advanced by :"; b, "seconds."
GOTO 40

'This loop decides if the analysis gave a better fit than the previous one
'**The number on the end is a limit for the maximum error allowed between a..
'**line of best fit and the data points. This is to ensure that when the ....
'**errors are largest (before shifting a large amount) the loop will not
'**accept a slight worsening in the fit as the correct answer and proceed..
'**until the fit is better. The setting of the value varies from expt to..
'**expt and if the program crashes or gives false results then this value..
'probably needs to be altered. (But don't quote me on that)*****
DO WHILE avdif(n) < avdif (n - 1) OR m(n - 1) < 0 OR avdif (n) > .5
40 n = n + 1: xtot = 0: xsqtot = 0: ytot = 0: xytot = 0: totdif = 0
j = n - 1           '*****n=no of times through shifting process*
k = num - j
v = 1
'                   *****Line of best fit calculations*****
DO UNTIL v = k + 1
xtot = xtot + x(v)
xsq = x(v) ^ 2: xstot = xsqtot + xsq
v = v +1
LOOP
LOCATE 10, 32: PRINT b
xav# = xtot / k
yav# = xtot / k
Sxx = xsqtot - ((xtot ^ 2) / k)
Sxy = xytot - (xtot * ytot / k)
m(n) = Sxy / Sxx
c(n) = yav$ - m(n) * xav$
PRINT "slope", m(n): PRINT "const", c(n)
'                   *****Difference of the squares calculation*****
w = 1
DO UNTIL w = k + 1
dif = ABS((m(n) * x(w) + c(n)) - y(w + j)
totdif = totdif + dif
w = w + 1
LOOP

```
avdif(n) = totdif / k
PRINT "Average Sum of Differences Squared ", avdif(n)
b = b + sampint
LOOP
```

[PAGE 13]
PRINT "The Phase Difference has been resolved for section"; sectb
PRINT
PRINT "The Dq/dt signal had to be shifted forward in time by (s) :"; b - (2 * sampint)
PRINT "the line of best fit through the points has gradient : ", m(n - 1)
PRINT "and an offset of : ", c(n - 1)
PRINT "The average sum of the Differences is : ", avdif(in - 1)
PRINT #2, initime, sectn, m(n - 1), t(n - 1), b - (2 * sampint)

*****looking for start of parset of data*****
50 ERASE N: ERASE y
IF EDF(1) THEN GO TO 20
INPUT #1, t, cydT, Tm, cydQ
y = cycQ: x = -cydT
GO TO WHILE y = 100
IF EDF(1) THEN GOTO 20
INPUT #1, t, cydT, Tm, cycQ
y = cycQ: x = -cydT
LOOP
initime = t: count = 1: y(count) = cycQ: x(count) = -cydT
sectn = sectn +1
LOOP
ERASE x: ERASE
CLOSE #1: CLOSE #2
a = a + 1
IF a = 2 OR a = 3 THEN GO TO 10

*****Erasing "go between" files*****
KILL "c:\rob\pars\TEMPAR1.DAT"
KILL "c:\rob\pars\TEMPAR2.HT"
KILL "c:\rob\pars\TEMPAR2.CL"
KILL "c:\rob\pars\TEMPAR2.RH"
CLS : PRINT " Congratulations, your task is completed."
PRINT
PRINT "Output data is saved as : c:\rob\pars\"; out$; .HT .CL and .RH"
SLEEP 10
RUN "c:\rob\intro.bas"
END
100 PRINT #2, initime, sectn
GOTO 50

*****CDTPAR2.BAS*****
CLS
PRINT "CDTPAR2 - Parsing data into two files : +ye and -ye Cyclic Deriv Mod Temp."
OPEN "C:\rob\pars\TEMPAR1.dat" FOR INPUT AS #1
OPEN "c:\rob\PARS\CYCPAR2.HT" FOR OUTPUT AS #2
OPEN "C:\rob\PARS\CYCPAR2.CL" FOR OUTPUT AS #3
'SOUND 250, 10: SOUND 210, 5: SOUND 170, 10: SOUND 210, 10: SOUND 250, 10: SOUND 340, 20
mark = 100
INPUT #1, fil$, out$, sampint
WRITE #2, fil$, out$, sampint
WRITE #3, fil$, out$, sampint
LOCATE 12, 20: PRINT "Time (s) ="

DO UNTIL EDF(1)
LOCATE 12, 30
INPUT #1, t, Tm, cymT, cydT, tycQ
IF cydT >= ) THEN
PRINT "heat"
WRITE #2, t, cydT, Tm, cycQ
WRITE #3, t, cydT, mark, mark
ELSE
PRINT "cool"

[PAGE 14]
```
WRITE #3, t, cydT, Tm, cyc@
WRITE #2, t, cydT, mark, mark
END IF
LOOP
CLOSE #1: CLOSE #2: CLOSE #3
CLS
'SOUND 420, 10: SOUND 380, 5: SOUND 330, 10: SOUND 210, 10: SOUND 230, 10: SOUND 250, 10
RUN "C:\rob\pars\CYCPAR3.BAS"
END
```

*****CHFPAR2.BAS*****
```
CLS
PRINT "CHFPAR2 - Parsing data into two files : Positive and negative Cyclic Heat Flow."
OPEN"C:\rob\pars\TEMPAR1.dat" FOR INPUT AS #1
OPEN" "C:rob|pars|CYCPAR2.HT" FOR OUTPUT AS #2
OPEN "C:\rob\pars\CYCPAR2.CL" FOR OUTPUT AS #3
'SOUND 250, 10: SOUND 210, 5: SOUND 170, 10: SOUND 210, 10: SOUND 250, 10: SOUND 340, 20
mark = 100
INPUT #1, fil$, out$, sampint
WRITE #2, fil$, out$, sampint
WRITE #3, fil$, out$, sampint
LOCATE 12, 20: PRINT "Time (s) "

DO UNTIL EDF(1)
LOCATE 12, 30
INPUT #1, t, Tm, cymT, cydT, cycQ
PRINT t
IF cytQ = 0 THEN
PRINT "heat"
WRITE #2, t, cydT, Tm, cycQ
WRITE #3, t, cydT, mark, mark
ELSE
PRINT "cool"
WRITE #3, t, cydT, Tm, cycQ
WRITE #2, t, cydT, mark, mark
END IF
LOOP
CLOSE #1: CLOSE #2: CLOSE #3
CLS
'SOUND 420, 10: SOUND 380, 5: SOUND 330, 10: SOUND 210, 10: SOUND 230, 10: SOUND 250, 10
RUN "C:\rob\pars\CYCPAR3.BAS"
END
```

*****CMTPAR2.BAS*****
```
CLS
PRINT "CMTPAR2 - Parsing data into two files : Positive and negative Cyclic Mod Temp."
OPEN "C:\rob\pars\TEMPAR1.dat" FOR INPUT AS #1
OPEN "C:\rob|PARS\CYCPAR2.HT" FOR OUTPUT AS #2
OPEN "C:\rob\PARS\CYCPAR2.CL'" FOR OUTPUT AS #3
'SOUND 250, 10: SOUND 210, 5: SOUND 170, 10: SOUND 250, 10: SOUND 340, 20
mark = 100
INPUT #1, fil$, out$, sampint
WRITE #2, fil$, out$, sampint
WRITE #3, fil$, out$, sampint
LOCATE 12, 20: PRINT "(Time (s) ="

DO UNTIL EDF (1)
LOCATE 12, 30
```

[PAGE 15]
PRINT t
IF cymT )= THEN
PRINT "heat"
WRITE #2, t, cydT, Tm, cycQ
WRITE #3, t, cydT, mark, mark
ELSE
PRINT "cool"
WRITE #3, t, cydT, Tm, cycQ
WRITE #2, t, cydT, mark, mark
END IF
LOOP
CLOSE #1: CLOSE #2: CLOSE #3
CLE
'SOUND 420, 10: SOUND 380, 5: SOUND 330, 10: SOUND 210, SOUND 230,10: SOUND 250, 10
RUN "C:\rob\pars\CVCPAR3.BAS"
END

***CYCPAR3.BAS***
*****A Linear Regression Program*****
*****Works on output from C??PAR2.BAS*****

*****Program loop determining which files are analysed*****
ON ERROR GOTO 100
a = 1
10 CLS
PRINT " CYCPAR3 -      Working out Heat Capacities of Parsets of Data"
PRINT "                using linear regression and a least square fit."
PRINT
SELECT CASE a
CASE 1
OPEN "C:\rob\pars\CYCPAR2.HT: FOR INPUT AS #1
INPUT #1, fil$, out$, sampint
OPEN "C:\rob\pars\" + out$ + ".HT" FOR OUTPUT AS #2
PRINT "Deconvoluting Heating Data from : "; fil$, "sampint: "; sampint
CASE 2
OPEN "C:\rob\pars\CYCPAR2.CL" FOR INPUT AS #1
INPUT #1, fil$, out$, sampint
CASE 2
OPEN "C:\rob\pars\" + out$ + ".CL" FOR OUTPUT AS #2
PRING "Deconvoluting Cooling Data from : "; fil$, "sampint: "; sampint
END SELECT DIM x (500): DIM y (500): DIM m(50): DIM c(50): DIM avdif(50)
sectn = 0: y(0) = 0

DO UNTIL y = 100        *Finding first data gap in file*
INPUT #1, t, cydl, Tm, cyc@  '(to ensure first parset analysed is a complete one)
y = cyc@: x = -cydT
LOOP
GOTO 60

20 DO UNTIL EDF (1)    ***Main loop for each parset***
30 inicount = count
GO UNTIL y (count) = 100        '*Loading in parset data* count = count + 1
INPUT #1, t, sydT, Tm, cyc@
IF EDF (1) THEN GOTO 20
y (count) = cycQ = x(count) = -cydT
LOOP num = count - incount '******Calculation******

[PAGE 16]
ERASE avdif, m, c: n = 0: 0 = 0: avdif(0) = 10000000
LOCATE 10, 12: PRINT "-dT/dt advanced by :"; b, "seconds."
GOTO 40

'This loop decides if the analysis gave a better fit than the previous one
'**The number on the end is a limit for the maximum error allowed between a..
'**line of best fit and the data points. This is to ensure that when the ....
'**errors are largest (before shifting a large amount) the loop will not
'**accept a slight worsening in the fit as the correct answer and proceed..
'**until the fit is better. The setting of the value varies from expt to..
'**expt and if the program crashes or gives false results the this value..
'probably needs to be altered. (But don't quote me on that)********
DO WHILE avdif(n) < avdif (n - 1) OR m(n - 1) < 0 OR avdif (n) > .5
40 n = n +1: xtot = 0: xsqtot = 0: ytot = 0: xytot =0; totdif = 0
j = n - 1                '*****n=no of times through shifting process*
k = num - j
v = 1
'                    ***Line of best fit calculations*****
DO UNTIL v = k + 1
xtot = xtot + x(v)
xsq = x(v) ^ 2: xsqtot = xsqtot + xsq
ytot = ytot + y(v + j)
ytot = x(v) * y(v + j)
xytot = xytot +xy
v = v + 1
LOOP
LOCATE 10, 32: PRINT b
IF k = 0 THEN GOTO 100
xav# = xtot / k
yav# = ytot / k
Sxx = xsqtot - z((xtot ^ 2) / k)
Sxy = xytot - (xtot $ ytot / k)
m(n) = Sxy / Sxx
c(n) = yay# - m(n) * xay#
PRINT "slope", m(n): PRINT "const," c(n)
'                    *****Difference of the squares calculation*****
w = 1
DO UNTIL w = k + 1
dif = ABS ((m(n) * x(W) + c(n)) - y(w + j)
totdif = totdif + dif
w = w + 1
LOOP
avdif(n) = totdif / k
PRINT "Average Sum of Differences Squared ", avdif(n)
b = b + sampint
LOOP
    **parset has been analysed so results are shown and output*
LOCATE 16, 1
PRINT "The Phase Difference has been resolved for section"; sectn
PRINT
PRINT "The dQ/dt signal had to be shifted forward in time by (s) :"; b - (2 * sampint)
PRINT "The line of best fit through the points has gradient : ", m(n - 1)
PRINT "and an offset of : ", c(n - 1)
PRINT "The average sum of the Differences is : ", avdif (n - 1)
PRINT #2, initime, sectn, m(n - 1), c(n - 1), b - (2 * sampint)

*****looking for start of parset of data*****
50 ERASE x: ERASE y
IF EDF(1) THEN GOTO 20
INPUT #1, t, cydT, Tm, cycQ
y = cycQ: x = -cydT
60 DO WHILE y = 100

```
IF EDF (1) THEN GOTO 20
INPUT #1, t, cydT, Tm, cycQ
y = cycQ: w = -cydT
LOOP
initime = t: count = 1: y(count) = cycQ: x(count) = cydT
sectn = sectn +1
LOOP
ERASE x: ERASE y
```

[PAGE 16]

```
CLS " PRINT "          Congratulations, your task is complete!!"
PRINT
PRINT "Output data is saved as "c:\rob\pars\"; out$; ".HT and .CL "
SLEEP 10
RUN "C:\rob\intro.bas"
END
1000 " PRINT #2, initime, sectn
GOTO 50
```

What is claimed is:

1. A method for analyzing a material using a differential scanning calorimeter, said differential scanning calorimeter having a sample pan and a reference pan comprising the steps of:

(a) selecting an underlying heating rate;

(b) selecting a first modulation function characterized by a first modulation amplitude and a first modulation frequency;

(c) placing a sample of the material in the sample pan of the differential scanning calorimeter;

(d) varying the temperature of the sample pan of the differential scanning calorimeter according to the selected underlying heating rate and the first selected modulation function;

(e) recording a signal representative of differential changes in the heat flow to and from the sample pan with respect to the reference pan to obtain differential heat flow data;

(f) parsing the differential heat flow data according to the temperature conditions the sample was experiencing as the differential heat flow data was collected; and (g) storing the parsed differential heat flow data in separate files.

2. The method of claim 1, wherein the data is parsed according to whether the sample was being heated, cooled or re-heated while the heat flow data was being collected, further comprising (h) storing the differential heat flow data obtained while the sample was being heated in a first file, storing the differential heat flow data obtained while the sample was being cooled in a second file, and storing the differential heat flow data obtained while the sample was being re-heated in a third file.

3. The method of claim 2, further comprising calculating heat capacity data from the first file, the second file and from the third file.

4. The method of claim 3, further comprising calibrating the instrument by selecting a reference material, executing steps (a)–(i) with an empty sample pan to obtain empty sample pan heat capacity data, executing steps (a)–(i) with a sample of the reference material in the sample pan to produce reference heat capacity data, subtracting the empty pan heat capacity data from the reference heat capacity data to produce net reference heat capacity data, comparing the net reference heat capacity data to known values of the heat capacity of the reference material to obtain calibration data, executing steps (a)–(i) with a sample of the material to be analyzed in the sample pan to produce sample heat capacity data, and multiplying the sample heat capacity data to obtain calibrated heat capacity data.

5. The method of claim 4, further comprising the step of deconvoluting at least one of the first file, the second file and the third file to compute at least one deconvoluted data file.

6. The method of claim 4, further comprising the step of deconvoluting at least one of the first file, the second file and the third file into a file representing rapidly reversible and non-rapidly reversible components of the data.

7. The method of claim 2, further comprising the step of deconvoluting at least one of the first file, the second file and the third file to compute at least one deconvoluted data file.

8. The method of claim 2, further comprising the step of deconvoluting at least one of the first file, the second file and the third file into a file representing rapidly reversible and non-rapidly reversible components of the data.

9. The method of claim 2, further comprising correcting for the phase lag due to the finite instrument response time.

10. The method of claim 9, wherein the step of correcting for the phase lag comprises:

(i) fitting a straight line to a parset of heat flow data, (ii) advancing the heat flow data forward by one data sampling interval to obtain heat flow data offset by one data sampling interval, (iii) fitting a straight line to the heat flow data offset by one data sampling interval, (iv) determining whether the linearity of the plot is improved, (v) if the linearity of the plot is improved, advancing the heat flow data by another sampling interval, fitting a straight line to the offset heat flow data, and determining whether the linearity of the plot is improved, (vi) repeating step (v) until the offset which produces the best linearity is determined, and (vii) storing a corrected parset of data having the offset determined in step (vi).

11. The method of claim 2, further comprising comparing the differential heat flow data obtained while the sample is being heated to at least one of the differential heat flow data obtained while the sample is being cooled and the differential heat flow data obtained while the sample is being re-heated, to identify transitions which have significantly different differential heat flow data obtained during heating compared to the at least one of the differential heat flow data obtained during cooling and the differential heat flow data obtained during re-heating.

12. The method of claim 1, wherein the modulated heat flow comprises a cyclic component, and wherein the data is parsed according to whether the cyclic component of the modulated heat flow is positive or negative, further comprising storing the differential heat flow data obtained while the cyclic component of the modulated heat flow was positive in a first file, and storing the differential heat flow data obtained while the cyclic component of the modulated heat flow was negative in a second file.

13. The method of claim 1, wherein the temperature of the sample as the data was collected comprises a cyclic component, and wherein the data is parsed according to whether the cyclic component of the temperature is positive or negative, further comprising storing the differential heat flow data obtained while the cyclic component of the temperature was positive in a first file, and storing the differential heat flow data obtained while the cyclic component of the temperature was negative in a second file.

14. The method of claim 1, further comprising calculating the derivative of the modulated temperature, wherein the derivative of the modulated temperature comprises a cyclic component, and wherein the data is parsed according to whether the cyclic component of the derivative of the modulated temperature is positive or negative, still further comprising storing the differential heat flow data obtained while the cyclic component of the derivative of the modulated temperature was positive in a first file, and storing the differential heat flow data obtained while the cyclic component of the derivative of the modulated temperature was negative in a second file.

15. The method of claim 1, wherein step (b) further comprises selecting a second modulation function characterized by a second modulation amplitude and a second modulation frequency, and wherein step (d) comprises varying the temperature of the sample pan according to the selected second modulation function in addition to varying the temperature according to the selected underlying heating rate and the selected first modulation function.

16. The method of claim 15, wherein the data is parsed according to whether the sample was being heated, cooled or re-heated as the heat flow data was collected, further comprising storing the differential heat flow data obtained while the sample was being heated in a first file, storing the differential heat flow data obtained while the sample was being cooled in a second file, and storing the differential heat flow data obtained while the sample was being re-heated in a third file.

17. The method of claim 16, further comprising calculating heat capacity data from the first file, the second file and from the third file.

18. The method of claim 15, wherein the modulated heat flow comprises a cyclic component, and wherein the data is parsed according to whether the cyclic component of the modulated heat flow was positive or negative, further comprising storing the differential heat flow data obtained while the cyclic component of the modulated heat flow was positive in a first file, and storing the differential heat flow data obtained while the cyclic component of the modulated heat flow was negative in a second file.

19. The method of claim 15, further comprising calculating the derivative of the modulated temperature, wherein the derivative of the modulated temperature comprises a cyclic component, and wherein the data is parsed according to whether the cyclic component of the derivative of the modulated temperature is positive or negative, still further comprising storing the differential heat flow data obtained while the cyclic component of the derivative of the modulated temperature was positive in a first file, and storing the differential heat flow data obtained while the cyclic component of the derivative of the modulated temperature was negative in a second file.

20. The method of claim 15, wherein the temperature of the sample as the data was collected comprises a cyclic component, and wherein the data is parsed according to whether the cyclic component of the temperature is positive or negative, further comprising storing the differential heat flow data obtained while the cyclic component of the temperature was positive in a first file, and storing the differential heat flow data obtained while the cyclic component of the temperature was negative in a second file.

21. A differential scanning calorimeter comprising:
   (a) a sample position and a reference position;
   (b) means for varying the temperature of the sample position according to an underlying heating rate;
   (c) means for selecting a modulation function characterized by a modulation frequency and a modulation amplitude;
   (d) means for controlling the temperature of the sample position according to the selected underlying heating rate and modulation function;
   (e) means for detecting the heat flow to and from the sample position with respect to a reference as a function of temperature, as the temperature is varied according to the modulation function;
   (f) means for recording a signal representative of differential changes in the heat flow to and from the sample position with respect to the reference position; and
   (g) means for parsing the differential heat flow data according to the temperature conditions the sample was experiencing as the differential heat flow data was collected.

22. The differential scanning calorimeter of claim 21, wherein the means for parsing the differential heat flow data parses the data according to whether the sample was being heated, cooled or re-heated while the heat flow data was being collected, further comprising storing the differential heat flow data obtained while the sample was being heated in a first file, storing the differential heat flow data obtained while the sample was being cooled in a second file, and storing the differential heat flow data obtained while the sample was being re-heated in a third file.

23. The differential scanning calorimeter of claim 22, further comprising means for deconvoluting the differential heat flow data in at least one of the first file, the second file and the third file to compute at least one deconvoluted data file.

24. The differential scanning calorimeter of claim 23, further comprising means for controlling the underlying heating rate according to the at least one deconvoluted signal.

25. The differential scanning calorimeter of claim 22, further comprising means for deconvoluting the differential heat flow data in at least one of the first file, the second file and the third file into data files containing rapidly reversible and non-rapidly reversible differential heat flow data.

26. The differential scanning calorimeter of claim 22, further comprising means for calculating heat capacity data from the first file, the second file and from the third file.

27. The differential scanning calorimeter of claim 26, further comprising means for calculating a calibration factor for each heat capacity data point by comparing heat capacity data obtained with a reference material at the sample position to known values of the heat capacity of the reference material.

28. The differential scanning calorimeter of claim 27, further comprising means for deconvoluting at least one of the first file, the second file and the third file to compute at least one deconvoluted data file.

29. The differential scanning calorimeter of claim 22, further comprising means for correcting for the phase lag due to the finite response time of the instrument.

30. The differential scanning calorimeter of claim 29, wherein the means for correcting for the phase lag comprises:
   (i) means for fitting a straight line to a parset of heat flow data,
   (ii) means for advancing the heat flow data forward by one data sampling interval to obtain heat flow data offset by one data sampling interval,
   (iii) means for fitting a straight line to the heat flow data offset by one data sampling interval,
   (iv) means for determining whether the linearity of the plot is improved,
   (v) means for advancing the heat flow data by additional sampling intervals as long as the linearity of the plot is improved until a corrected parset of data is obtained, and
   (vi) means for storing the corrected parset of data.

31. The differential scanning calorimeter of claim 22, further comprising means for comparing the differential heat flow data obtained while the sample is being heated to at least one of the differential heat flow data obtained while the sample is being cooled and the differential heat flow data obtained while the sample is being re-heated, to identify transitions which have significantly different differential heat flow data obtained during heating compared to the at least one of the differential heat flow data obtained during cooling and the differential heat flow data obtained during re-heating.

32. The differential scanning calorimeter of claim 21, wherein the modulated heat flow comprises a cyclic component, and wherein the means for parsing data parses the data according to whether the cyclic component of the modulated heat flow is positive or negative, further comprising means for storing the differential heat flow data obtained while the cyclic component of the modulated heat flow was positive in a first file, and storing the differential heat flow data obtained while the cyclic component of the modulated heat flow was negative in a second file.

33. The differential scanning calorimeter of claim 21, wherein the temperature of the sample as the data was collected comprises a cyclic component, and wherein the means for parsing data parses the data according to whether the cyclic component of the temperature is positive or negative, further comprising means for storing the differential heat flow data obtained while the cyclic component of the temperature was positive in a first file, and storing the differential heat flow data obtained while the cyclic component of the temperature was negative in a second file.

34. The differential scanning calorimeter of claim 21, wherein the derivative of the modulated temperature comprises a cyclic component, and wherein the means for parsing data parses the data according to whether the cyclic component of the derivative of the modulated temperature is positive or negative, further comprising means for storing the differential heat flow data obtained while the cyclic component of the derivative of the modulated temperature was positive in a first file, and storing the differential heat flow data obtained while the cyclic component of the derivative of the modulated temperature was negative in a second file.

35. A differential scanning calorimeter comprising:
 (a) a sample position and a reference position;
 (b) means for varying the temperature of the sample position according to an underlying heating rate;
 (c) means for selecting a multiplex modulation function characterized by a first modulation frequency, a second modulation frequency, a first modulation amplitude and a second modulation frequency;
 (d) means for controlling the temperature of the sample position according to the selected underlying heating rate and multiplex modulation function;
 (e) means for detecting the heat flow to and from the sample position with respect to a reference as a function of temperature, as the temperature is varied according to the multiplex modulation function; and
 (f) means for recording a signal representative of differential changes in the heat flow to and from the sample position with respect to the reference position.

36. The differential scanning calorimeter of claim 35, further comprising means for parsing the differential heat flow data according to the temperature conditions the sample was experiencing as the differential heat flow data was collected wherein the means for parsing the differential heat flow data parses the data according to whether the sample was being heated, cooled or re-heated while the heat flow data was being collected, further comprising storing the differential heat flow data obtained while the sample was being heated in a first file, storing the differential heat flow data obtained while the sample was being cooled in a second file, and storing the differential heat flow data obtained while the sample was being re-heated in a third file.

37. The differential scanning calorimeter of claim 35, wherein the modulated heat flow comprises a cyclic component, further comprising means for parsing the differential heat flow data according to whether the cyclic component of the modulated heat flow is positive or negative, means for storing the differential heat flow data obtained while the cyclic component of the modulated heat flow was positive in a first file, and means for storing the differential heat flow data obtained while the cyclic component of the modulated heat flow was negative in a second file.

38. The differential scanning calorimeter of claim 35, wherein the temperature of the sample as the data was collected comprises a cyclic component, further comprising means for parsing the data according to whether the cyclic component of the temperature is positive or negative, means for storing the differential heat flow data obtained while the cyclic component of the temperature was positive in a first file, and means for storing the differential heat flow data obtained while the cyclic component of the temperature was negative in a second file.

39. The differential scanning calorimeter of claim 35, further comprising means for calculating the derivative of the modulated temperature, wherein the derivative of the modulated temperature comprises a cyclic component, means for parsing the data according to whether the cyclic component of the derivative of the modulated temperature is positive or negative, means for storing the differential heat flow data obtained while the cyclic component of the derivative of the modulated temperature was positive in a first file, and means for storing the differential heat flow data obtained while the cyclic component of the derivative of the modulated temperature was negative in a second file.

40. The differential scanning calorimeter of claim 35, further comprising means for correcting for the phase lag due to the finite instrument response time.

41. A method for analyzing a material comprising the steps of:
 (a) providing a heat flux differential scanning calorimeter having a sample position;
 (b) selecting an underlying heating rate;
 (c) selecting a modulation function characterized by a modulation frequency and a modulation amplitude;
 (d) placing a reference material at the sample position;
 (e) varying the temperature of the sample position at the selected underlying heating rate;
 (f) recording a reference signal representative of the heat flow to the sample position;
 (g) placing a sample of the material on the sample position of the differential scanning calorimeter;
 (h) varying the temperature of the sample position such that the average temperature of the sample position increases at the underlying heating rate, and applying an oscillating heat flow to the sample position, said heat flow oscillating according to the selected modulation function;
 (i) recording a differential signal representative of the average differential total heat flow to the sample position compared to the reference signal, and recording the average temperature of the sample position; and
 (j) parsing the differential signal according to whether the signal was obtained as the sample was being heated, cooled or re-heated;
 (k) storing the data obtained from the differential signal while the sample was being heated in a first file, storing the data obtained from the differential signal while the sample was being cooled in a second file, and storing the data obtained from the differential signal while the sample was being re-heated in a third file.

42. The method of claim 41, further comprising (l) calculating heat capacity data from the first file, the second file and from the third file.

43. The method of claim 42, further comprising (m) calibrating the instrument by selecting a reference material, executing steps (a) through (l) with an empty sample pan to obtain empty sample pan heat capacity data, executing steps (a) through (l) with a sample of the reference material in the sample pan to produce reference heat capacity data, subtracting the empty pan heat capacity data from the reference heat capacity data to produce net reference heat capacity data, comparing the net reference heat capacity data to known values of the heat capacity of the reference material to obtain calibration data, executing steps (a) through (l) with a sample of the material to be analyzed in the sample pan to produce sample heat capacity data, and multiplying the sample heat capacity data to obtain calibrated heat capacity data.

44. The method of claim 43, further comprising the step of deconvoluting at least one of the first file, the second file and the third file to compute at least one deconvoluted data file.

45. The method of claim 43, further comprising the step of deconvoluting at least one of the first file, the second file and the third file into a file representing rapidly reversible and non-rapidly reversible components of the data.

46. The method of claim 41, further comprising the step of deconvoluting at least one of the first file, the second file and the third file to compute at least one deconvoluted data file.

47. The method of claim 41, further comprising the step of deconvoluting at least one of the first file, the second file and the third file into a file representing rapidly reversible and non-rapidly reversible components of the data.

48. The method of claim 41, further comprising correcting for the phase lag due to the finite instrument response time.

49. The method of claim 48, wherein the step of correcting for the phase lag comprises:

(i) fitting a straight line to a parset of heat flow data, (ii) advancing the heat flow data forward by one data sampling interval to obtain heat flow data offset by one data sampling interval, (iii) fitting a straight line to the heat flow data offset by one data sampling interval, (iv) determining whether the linearity of the plot is improved, (v) if the linearity of the plot is improved, advancing the heat flow data by another sampling interval, fitting a straight line to the offset heat flow data, and determining whether the linearity of the plot is improved, (vi) repeating step (v) until the offset which produces the best linearity is determined, and (vii) storing a corrected parset of data having the offset determined in step (vi).

50. The method of claim 41, further comprising comparing the differential heat flow data obtained while the sample is being heated to at least one of the differential heat flow data obtained while the sample is being cooled and the differential heat flow data obtained while the sample is being re-heated, to identify transitions which have significantly different differential heat flow data obtained during heating compared to the at least one of the differential heat flow data obtained during cooling and the differential heat flow data obtained during re-heating.

51. A heat flux differential scanning calorimeter comprising:

(a) a sample position;

(b) means for selecting an underlying heating rate;

(c) means for selecting a modulation function characterized by a modulation frequency and a modulation amplitude;

(d) means for varying the temperature of the sample position at the selected underlying heating rate;

(e) means for recording a reference signal representative of the heat flow to the sample position;

(f) means for varying the temperature of the sample position such that the average temperature of the sample position increases at the underlying heating rate, and applying an oscillating heat flow to the sample position, said heat flow oscillating according to the selected modulation function;

(g) means for recording a differential signal representative of the average differential total heat flow to the sample position compared to the reference signal, and recording the average temperature of the sample position; and (h) means for parsing the differential signal according to whether the signal was obtained as the sample was being heated, cooled or re-heated; and (i) means for storing the data obtained from the differential signal while the sample was being heated in a first file, storing the data obtained from the differential signal while the sample was being cooled in a second file, and storing the data obtained from the differential signal while the sample was being re-heated in a third file.

52. The differential scanning calorimeter of claim 51, further (j) comprising means for calculating heat capacity data from the first file, the second file and from the third file.

53. The differential scanning calorimeter of claim 52, further comprising (k) means for calibrating the instrument by selecting a reference material, executing steps (a) through (j) with an empty sample pan to obtain empty sample pan heat capacity data, executing steps (a) through (j) with a sample of the reference material in the sample pan to produce reference heat capacity data, subtracting the empty pan heat capacity data from the reference heat capacity data to produce net reference heat capacity data, comparing the net reference heat capacity data to known values of the heat capacity of the reference material to obtain calibration data, executing steps (a) through (j) with a sample of the material to be analyzed in the sample pan to produce sample heat capacity data, and multiplying the sample heat capacity data to obtain calibrated heat capacity data.

54. The differential scanning calorimeter of claim 53, further comprising means for deconvoluting at least one of the first file, the second file and the third file to compute at least one deconvoluted data file.

55. The differential scanning calorimeter of claim 53, further comprising means for deconvoluting at least one of the first file, the second file and the third file into a file representing rapidly reversible and non-rapidly reversible components of the data.

56. The differential scanning calorimeter of claim 51, further comprising means for deconvoluting at least one of the first file, the second file and the third file to compute at least one deconvoluted data file.

57. The differential scanning calorimeter of claim 51, further comprising means for deconvoluting at least one of the first file, the second file and the third file into a file representing rapidly reversible and non-rapidly reversible components of the data.

58. The differential scanning calorimeter of claim 1, further comprising means for correcting for the phase lag due to the finite instrument response time.

59. The diffential scanning calorimeter of claim 8, further comprising:
  (i) means for fitting a straight line to a parset of heat flow data,
  (ii) means for advancing the heat flow data forward by one data sampling interval to obtain heat flow data offset by one data sampling interval,
  (iii) means for fitting a straight line to the heat flow data offset by one data sampling interval,
  (iv) means for determining whether the linearity of the plot is improved,
  (v) means for advancing the heat flow data by additional sampling intervals as long as the linearity of the plot is improved, until a corrected parset of data is obtained, and
  (vi) means for storing the corrected parset of data.

60. The differential scanning calorimeter of claim 51, further comprising means for comparing the differential heat flow data obtained while the sample is being heated to at least one of the differential heat flow data obtained while the sample is being cooled and the differential heat flow data obtained while the sample is being re-heated, to identify transitions which have significantly different differential heat flow data obtained during heating compared to the at least one of the differential heat flow data obtained during cooling and the differential heat flow data obtained during re-heating.

61. A method for analyzing a material using a differential scanning calorimeter, said differential scanning calorimeter having a sample pan and a reference pan comprising the steps of:
  (a) selecting an underlying heating rate;
  (b) selecting a multiplex modulation function characterized by at least two different modulation frequencies;
  (c) placing a sample of the material in the sample pan of the differential scanning calorimeter;
  (d) varying the temperature of the sample pan of the differential scanning calorimeter according to the selected underlying heating rate and the selected multiplex modulation function; and
  (e) recording a signal representative of differential changes in the heat flow to and from the sample pan with respect to the reference pan to obtain multiplexed differential heat flow data.

62. The method of claim 31, further comprising parsing the multiplexed differential heat flow data according to the temperature conditions the sample was experiencing as the differential heat flow data was collected and storing the parsed multiplexed differential heat flow data in separate files.

63. The method of claim 62, wherein the data is parsed according to whether the sample was being heated, cooled or re-heated while the heat flow data was being collected, further comprising storing the differential heat flow data obtained while the sample was being heated in a first file, storing the differential heat flow data obtained while the sample was being cooled in a second file, and storing the differential heat flow data obtained while the sample was being re-heated in a third file.

64. The method of claim 62, wherein the modulated heat flow comprises a cyclic component, and wherein the data is parsed according to whether the cyclic component of the modulated heat flow is positive or negative, further comprising storing the differential heat flow data obtained while the cyclic component of the modulated heat flow was positive in a first file, and storing the differential heat flow data obtained while the cyclic component of the modulated heat flow was negative in a second file.

65. The method of claim 62, wherein the temperature of the sample as the data was collected comprises a cyclic component, and wherein the data is parsed according to whether the cyclic component of the temperature is positive or negative, further comprising storing the differential heat flow data obtained while the cyclic component of the temperature was positive in a first file, and storing the differential heat flow data obtained while the cyclic component of the temperature was negative in a second file.

66. The method of claim 62, further comprising calculating the derivative of the modulated temperature, wherein the derivative of the modulated temperature comprises a cyclic component, and wherein the data is parsed according to whether the cyclic component of the derivative of the modulated temperature is positive or negative, further comprising storing the differential heat flow data obtained while the cyclic component of the derivative of the modulated temperature was positive in a first file, and storing the differential heat flow data obtained while the cyclic component of the derivative of the modulated temperature was negative in a second file.

67. The method of claim 61, wherein the first frequency is an integral multiple of the second frequency.

68. The method of claim 61, further comprising deconvoluting the multiplexed differential heat flow data to obtain differential heat flow data modulated at the first frequency.

69. The method of claim 68, further comprising deconvoluting the multiplexed differential heat flow data a second time to obtain the underlying heat capacity.

* * * * *